United States Patent
Kamenecka et al.

(10) Patent No.: US 10,221,170 B2
(45) Date of Patent: Mar. 5, 2019

(54) DIFLUOROPYRROLIDINES AS OREXIN RECEPTOR MODULATORS

(71) Applicant: Eolas Therapeutics, Inc., Carlsbad, CA (US)

(72) Inventors: Theodore M. Kamenecka, Palm Beach Gardens, FL (US); Yuanjun He, Palm Beach Gardens, FL (US)

(73) Assignee: Eolas Therapeutics, Inc., Carlsbad, CA (US)

( * ) Notice: Subject to any disclaimer, the term of this patent is extended or adjusted under 35 U.S.C. 154(b) by 1 day.

(21) Appl. No.: 15/503,131

(22) PCT Filed: Aug. 13, 2015

(86) PCT No.: PCT/US2015/044974
§ 371 (c)(1),
(2) Date: Feb. 10, 2017

(87) PCT Pub. No.: WO2016/025669
PCT Pub. Date: Feb. 18, 2016

(65) Prior Publication Data
US 2017/0226103 A1    Aug. 10, 2017

Related U.S. Application Data

(60) Provisional application No. 62/037,024, filed on Aug. 13, 2014.

(51) Int. Cl.
| | | |
|---|---|---|
| C07D 417/14 | (2006.01) | |
| C07D 401/14 | (2006.01) | |
| C07D 403/14 | (2006.01) | |

(52) U.S. Cl.
CPC ......... *C07D 417/14* (2013.01); *C07D 401/14* (2013.01); *C07D 403/14* (2013.01)

(58) Field of Classification Search
CPC .................................................. C07D 417/14
See application file for complete search history.

(56) References Cited

U.S. PATENT DOCUMENTS

| | | | |
|---|---|---|---|
| 5,049,578 | A | 9/1991 | Varma et al. |
| 9,896,452 | B2 | 2/2018 | Kamenecka et al. |
| 2008/0132490 | A1 | 6/2008 | Bergman et al. |
| 2009/0012073 | A1 | 1/2009 | Branch et al. |
| 2009/0203736 | A1 | 8/2009 | Knust et al. |
| 2010/0168134 | A1 | 7/2010 | Breslin et al. |
| 2010/0184808 | A1 | 7/2010 | Aissaoui et al. |
| 2011/0003835 | A1 | 1/2011 | Mueller et al. |
| 2011/0263643 | A1 | 10/2011 | Cox et al. |
| 2012/0165339 | A1 | 6/2012 | Terauchi et al. |
| 2012/0295921 | A1 | 11/2012 | Breslin et al. |
| 2014/0364432 | A1 | 12/2014 | Kamenecka et al. |
| 2014/0364433 | A1 | 12/2014 | Kamenecka et al. |

FOREIGN PATENT DOCUMENTS

| | | |
|---|---|---|
| CN | 1633433 | 6/2005 |
| CN | 101679366 A | 3/2010 |
| CN | 101730696 A | 6/2010 |
| EP | 2161266 A1 | 3/2010 |
| JP | 2010-155827 A | 7/2010 |
| WO | WO-1999/058533 A1 | 11/1999 |
| WO | WO-2000047576 A1 | 8/2000 |
| WO | WO-2000047577 A1 | 8/2000 |
| WO | WO-2000047580 A2 | 8/2000 |
| WO | WO-00/71508 A2 | 11/2000 |
| WO | WO-2001085693 A1 | 11/2001 |
| WO | WO-2001096302 A1 | 12/2001 |
| WO | WO-2002044172 A1 | 6/2002 |
| WO | WO-2002051232 A2 | 7/2002 |
| WO | WO-2002051838 A1 | 7/2002 |
| WO | WO-2002089800 A2 | 11/2002 |
| WO | WO-2002090355 A1 | 11/2002 |
| WO | WO-2003002559 A2 | 1/2003 |
| WO | WO-2003032991 A1 | 4/2003 |
| WO | WO-2003037847 A1 | 5/2003 |
| WO | WO-2003041711 A1 | 5/2003 |
| WO | WO-2003051368 A1 | 6/2003 |
| WO | WO-2003051872 A1 | 6/2003 |
| WO | WO-2003051873 A1 | 6/2003 |
| WO | WO-2004004733 A1 | 1/2004 |
| WO | WO-2004026866 A1 | 4/2004 |
| WO | WO-2004033418 A2 | 4/2004 |
| WO | WO-2004041791 A1 | 5/2004 |
| WO | WO-2004041807 A1 | 5/2004 |
| WO | WO-2004041816 A1 | 5/2004 |
| WO | WO-2004052876 A1 | 6/2004 |
| WO | WO-2004085403 A1 | 10/2004 |

(Continued)

OTHER PUBLICATIONS

Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*
Di Fabio, et al. "Discovery process and pharmacological characterization of a novel dual orexin 1 and orexin 2 receptor antagonist useful for treatment of sleep disorders", Bioorganic & Medicinal Chemistry Letters, Elsevier Ltd., 21 (18):5562-5567 (2011).
Gatfield, et al., "Orexin Receptor Antagonists: A New Concept in CNS Disorders?", ChemMedChem 5(8):1197-1214 (2010).

(Continued)

*Primary Examiner* — Shawquia Jackson
(74) *Attorney, Agent, or Firm* — White & Case LLP

(57) ABSTRACT

The present application relates to certain difluoropyrrolidine compounds, pharmaceutical compositions containing them, and methods of using them, including methods for treating substance addiction, panic disorder, anxiety, post-traumatic stress disorder, pain, depression, seasonal affective disorder, an eating disorder, or hypertension.

28 Claims, No Drawings

(56) References Cited

FOREIGN PATENT DOCUMENTS

| | | |
|---|---|---|
| WO | WO-2004096780 A1 | 11/2004 |
| WO | WO-2005060959 A1 | 7/2005 |
| WO | WO-2005075458 A1 | 8/2005 |
| WO | WO-2005118548 A1 | 12/2005 |
| WO | WO-2006067224 A2 | 6/2006 |
| WO | WO-2006110626 A1 | 10/2006 |
| WO | WO-2006127550 A1 | 11/2006 |
| WO | WO-2007008276 A2 | 1/2007 |
| WO | WO-2007019234 A2 | 2/2007 |
| WO | WO-2007025069 A2 | 3/2007 |
| WO | WO-2007061763 A2 | 5/2007 |
| WO | WO-2007/085718 A1 | 8/2007 |
| WO | WO-2007/088276 A2 | 8/2007 |
| WO | WO-2007085178 A1 | 8/2007 |
| WO | WO-2007085565 A1 | 8/2007 |
| WO | WO-2007116374 A1 | 10/2007 |
| WO | WO-2007122591 A2 | 11/2007 |
| WO | WO-2007126934 A2 | 11/2007 |
| WO | WO-2007143856 A1 | 12/2007 |
| WO | WO-2008008517 A2 | 1/2008 |
| WO | WO-2008008518 A1 | 1/2008 |
| WO | WO-2008008551 A2 | 1/2008 |
| WO | WO-2008020405 A2 | 2/2008 |
| WO | WO-2008026149 A1 | 3/2008 |
| WO | WO-2008038251 A2 | 4/2008 |
| WO | WO-2008065626 A2 | 6/2008 |
| WO | WO-2008078291 A1 | 7/2008 |
| WO | WO-2008081399 A2 | 7/2008 |
| WO | WO-2008087611 A2 | 7/2008 |
| WO | WO-2008107335 A1 | 9/2008 |
| WO | WO-2008108991 A1 | 9/2008 |
| WO | WO-2008110488 A1 | 9/2008 |
| WO | WO-2008117241 A2 | 10/2008 |
| WO | WO-2008122513 A1 | 10/2008 |
| WO | WO-2008/143856 A1 | 11/2008 |
| WO | WO-2008139416 A1 | 11/2008 |
| WO | WO-2008147518 A1 | 12/2008 |
| WO | WO-2008150364 A1 | 12/2008 |
| WO | WO-2009/004584 A1 | 1/2009 |
| WO | WO-2009/023126 A2 | 2/2009 |
| WO | WO-2009016087 A1 | 2/2009 |
| WO | WO-2009016560 A2 | 2/2009 |
| WO | WO-2009016564 A2 | 2/2009 |
| WO | WO-2009020642 A1 | 2/2009 |
| WO | WO-2009022311 A2 | 2/2009 |
| WO | WO-2009040730 A2 | 4/2009 |
| WO | WO-2009058238 A1 | 5/2009 |
| WO | WO-2009079637 A1 | 6/2009 |
| WO | WO-2009080533 A1 | 7/2009 |
| WO | WO-2009092642 A1 | 7/2009 |
| WO | WO-2009104155 A1 | 8/2009 |
| WO | WO-2009124956 A1 | 10/2009 |
| WO | WO-2009150614 A1 | 12/2009 |
| WO | WO-2009153180 A1 | 12/2009 |
| WO | WO-2009156951 A2 | 12/2009 |
| WO | WO-2010004507 A1 | 1/2010 |
| WO | WO-2010012620 A1 | 2/2010 |
| WO | WO-2010017260 A1 | 2/2010 |
| WO | WO-2010044054 A1 | 4/2010 |
| WO | WO-2010048010 A1 | 4/2010 |
| WO | WO-2010048012 A1 | 4/2010 |
| WO | WO-2010048013 A1 | 4/2010 |
| WO | WO-2010048014 A1 | 4/2010 |
| WO | WO-2010048016 A1 | 4/2010 |
| WO | WO-2010048017 A1 | 4/2010 |
| WO | WO-2010/051238 A1 | 5/2010 |
| WO | WO-2010051236 A1 | 5/2010 |
| WO | WO-2010051237 A1 | 5/2010 |
| WO | WO-2010051238 A1 | 5/2010 |
| WO | WO-2010060470 A1 | 6/2010 |
| WO | WO-2010060471 A1 | 6/2010 |
| WO | WO-2010060472 A1 | 6/2010 |
| WO | WO-2010063662 A1 | 6/2010 |
| WO | WO-2010063663 A1 | 6/2010 |
| WO | WO-2010072722 A1 | 7/2010 |
| WO | WO-2010086366 A1 | 8/2010 |
| WO | WO-2010122151 A1 | 10/2010 |
| WO | WO-2011005636 A1 | 1/2011 |
| WO | WO-2011006960 A1 | 1/2011 |
| WO | WO-2011016234 A1 | 2/2011 |
| WO | WO-2011023578 A1 | 3/2011 |
| WO | WO-2011023585 A1 | 3/2011 |
| WO | WO-2011050198 A1 | 4/2011 |
| WO | WO-2011050200 A1 | 4/2011 |
| WO | WO-2011050202 A1 | 4/2011 |
| WO | WO-2011053522 A1 | 5/2011 |
| WO | WO-2011061318 A1 | 5/2011 |
| WO | WO-2011073316 A1 | 6/2011 |
| WO | WO-2011076744 A1 | 6/2011 |
| WO | WO-2011076747 A1 | 6/2011 |
| WO | WO-2011138265 A2 | 11/2011 |
| WO | WO-2011138266 A1 | 11/2011 |
| WO | WO-2012081692 A1 | 6/2012 |
| WO | WO-2012085852 A1 | 6/2012 |
| WO | WO-2012085857 A1 | 6/2012 |
| WO | WO-2012089606 A1 | 7/2012 |
| WO | WO-2012089607 A1 | 7/2012 |
| WO | WO-2012101487 A1 | 8/2012 |
| WO | WO-2012110986 A1 | 8/2012 |
| WO | WO-2012114252 A1 | 8/2012 |
| WO | WO-2012145581 A1 | 10/2012 |
| WO | WO-2012153729 A1 | 11/2012 |
| WO | WO-2013005755 A1 | 1/2013 |
| WO | WO-2013050938 A1 | 4/2013 |
| WO | WO-2013059163 A1 | 4/2013 |
| WO | WO-2013059222 A1 | 4/2013 |
| WO | WO-2013062857 A1 | 5/2013 |
| WO | WO-2013062858 A1 | 5/2013 |
| WO | WO-2013068935 A1 | 5/2013 |
| WO | WO-2013092893 A1 | 6/2013 |
| WO | WO-2013/119639 A1 | 8/2013 |
| WO | WO-2013123240 A1 | 8/2013 |
| WO | WO-2013127913 A1 | 9/2013 |
| WO | WO-2013139730 A1 | 9/2013 |
| WO | WO-2015/123355 A1 | 8/2015 |

OTHER PUBLICATIONS

Heifetz et al, Study of Human Orexin-1 and -2 G-Protein_Coupled Receptors with Novel and Published Antagonists by Modeling, Molecular Dynamics Simulations, and Site-Directed Mutagenesis; Biochemistry, ( 2012), pp. 3178-3197.

Hirose et al, N-Acyl 6,7-Dimethoxy-1,2,3,4-tetrahydroisoquinolin: The First Orexin-2 Receptor Selective Non-peptidic Antagonist, Bioorganic and Medicinal Chemistry Letters, (2003) 4497-4499; Elsevier Ltd.

Jiang et al, Disubstituted piperidines as potent orexin (hypocretin) receptor antagonists; Bioorganic & Medicinal Chemistry Letters 22 (2012) 3890-3894.

Whitman et al, Discovery of a Potent, CNS-Penetrant Orexin Receptor Antagonist Based on and N,N-Disubstituted-1,4-diazepane Scaffold that Promotes Sleep in Rats, ChemMedChem 2009, 1069-1074.

\* cited by examiner

DIFLUOROPYRROLIDINES AS OREXIN RECEPTOR MODULATORS

CROSS-REFERENCE TO RELATED APPLICATIONS

This application is a national stage application under 35 U.S.C. § 371 of International Application No. PCT/US2015/044974, filed Aug. 13, 2015, which claims priority to U.S. provisional Application Serial No. 62/037,024, filed Aug. 13, 2014, which application is incorporated herein by reference in its entirety. International Application PCT/US2015/044974 was published under PCT Article 21(2) in English.

STATEMENT OF GOVERNMENT SUPPORT

This invention was made with government support under Grant Numbers 1 P01 DA033622 and 1 U01 NS083614 awarded by the National Institutes of Health. The government has certain rights in this invention.

BACKGROUND

Orexins are a family of homologous peptides including species orexin A, or OR-A, and orexin B, or OR-B. Orexin A is a 33 amino acid peptide and orexin B is a 28 amino acid peptide (Sakurai T. et al., Cell (1998), 92, 573-585). Orexins are produced in neurons of the lateral hypothalamus and bind to at least two distinct G-protein-coupled receptors, termed $OX_1$ and $OX_2$ receptors. The $OX_1$ receptor is selective for OR-A, while the $OX_2$ receptor can bind both OR-A and OR-B. Orexins are found to stimulate food consumption, regulate states of sleep and wakefulness, and may be involved in neural mechanisms of drug abuse and addiction.

There remains a need for small molecule modulators of orexin receptors, including $OX_1$ and $OX_2$, with desirable pharmaceutical properties. Certain difluoropyrrolidine compounds have been found in the context of this application to have this advantageous activity profile.

SUMMARY OF THE APPLICATION

In one aspect, the application provides a compound of Formula (I):

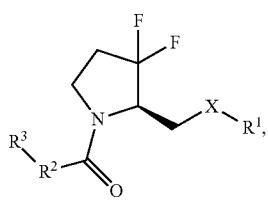

(I)

wherein
X is $NR^4$ or O;
$R^1$ is a monocyclic or bicyclic heteroaryl group, wherein $R^1$ is unsubstituted or substituted with one or more substituents independently selected from the group consisting of alkyl, haloalkyl, halo, —OH, —O-alkyl, —CN, —$NR^aR^b$, —$N(R^a)C(O)$ alkyl, —$N(R^a)CO_2$alkyl, —$N(R^a)SO_2$alkyl, —C(O)alkyl, —$CO_2H$, —$CO_2$alkyl, —$CONR^aR^b$, —$SO_2$alkyl, and —$SO_2NR^aR^b$;
where $R^a$ and $R^b$ are each independently H or alkyl;

$R^2$ is phenyl or a monocyclic heteroaryl, wherein $R^2$ is unsubstituted or substituted with one or more substituents independently selected from the group consisting of alkyl, haloalkyl, cycloalkyl, halo, —OH, —O-alkyl, —CN, —$NR^cR^d$, —$N(R^a)C(O)$ alkyl, —$N(R^c)CO_2$alkyl, —$N(R^c)SO_2$alkyl, —C(O)alkyl, —$CO_2H$, —$CO_2$alkyl, —$CONR^cR^d$, —$SO_2$alkyl, and —$SO_2NR^cR^d$;
where $R^c$ and $R^d$ are each independently H or alkyl;
$R^3$ is phenyl or a monocyclic heteroaryl, wherein $R^3$ is unsubstituted or substituted with one or more substituents independently selected from the group consisting of alkyl, haloalkyl, halo, —OH, —O-alkyl, —CN, —$NR^eR^f$, —$N(R^e)C(O)$ alkyl, —$N(R^e)CO_2$alkyl, —$N(R^e)SO_2$alkyl, —C(O)alkyl, —$CO_2H$, —$CO_2$alkyl, —$CONR^eR^f$, —$SO_2$alkyl, and —$SO_2NR^eR^f$;
where $R^e$ and $R^f$ are each independently H or alkyl; and
$R^4$ is H or alkyl;
or a pharmaceutically acceptable salt thereof.

In certain embodiments, the compound of Formula (I) can be represented by Formula (II):

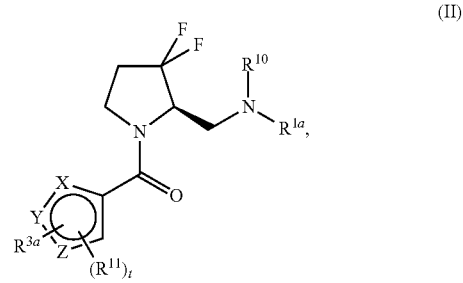

(II)

wherein
$R^{10}$ is H or alkyl;
$R^{1a}$ is a 6-membered heteroaryl, unsubstituted or substituted with alkyl, haloalkyl, or halo;
the ring system

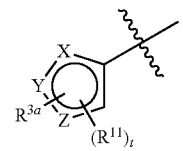

is defined as in (a), (b), or (c):

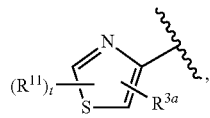

(a)

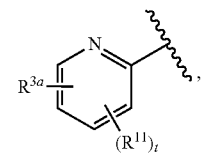

(b)

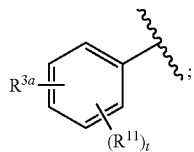

each R¹¹ is independently selected from the group consisting of alkyl, cycloalkyl, —CN, halo, and alkoxy;
t is 0, 1, or 2; and
R³ᵃ is phenyl or a monocyclic heteroaryl, unsubstituted or substituted with one or two substituents independently selected from the group consisting of alkyl, alkoxy, halo, —CN, and —CF₃;
or a pharmaceutically acceptable salt thereof.

In certain embodiments, the compound of Formula (I) or (II) is a compound selected from those species described or exemplified in the detailed description below.

In a further aspect, described herein is a pharmaceutical composition, comprising at least one compound of Formula (I) or (II) or a pharmaceutically acceptable salt thereof. Pharmaceutical compositions as described herein may further comprise a pharmaceutically acceptable excipient. Also described herein is a compound of Formula (I) or (II) or a pharmaceutically acceptable salt thereof for use as a medicament.

In another aspect, described herein are methods of treating a disease, disorder, or medical condition mediated by orexin receptor activity, such as those described herein, comprising administering to a subject in need of such treatment, such as a patient, an effective amount of at least one compound described herein or a pharmaceutically acceptable salt thereof in a dose, at a frequency, and for a duration to provide a beneficial effect to the subject. The orexin receptor can be OX₁, or can be OX₂.

In another aspect, described herein is the use of a compound described herein, or a pharmaceutically acceptable salt thereof, in the preparation of a medicament for the treatment of diseases, disorders, and medical conditions regulated by orexin receptor activity, and the use of such compounds and salts for treatment of such diseases and medical conditions.

In another aspect, described herein provides a method of treating a disease, disorder, or medial condition in a patient, comprising modulating an orexin receptor, wherein the modulating an orexin receptor comprises administering to the patient at least one compound of Formula (I) or (II), or a pharmaceutically acceptable salt thereof, in a dose, at a frequency, and for a duration to provide a beneficial effect to the patient. In various embodiments, the disease, disorder, or medical condition is an eating disorder, obesity, alcoholism or an alcohol-related disorder, drug abuse or addiction, a sleep disorder, a cognitive dysfunction in a psychiatric or neurologic disorder, depression, anxiety, panic disorder, post-traumatic stress disorder, seasonal affective disorder, schizophrenia, Alzheimer's disease, Parkinson's disease, Huntington's chorea, headache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease. Drug abuse and addiction can include abuse of or addiction to cocaine, opiates, amphetamines, ethanol, cannabis/marijuana, or nicotine.

In yet another aspect, described herein provides a method of modulating the activity of an orexin receptor, such as one or both of OX₁ or OX₂, comprising contacting a cell comprising the orexin receptor with an effective amount of at least one compound described herein, or a pharmaceutically acceptable salt thereof. In yet another aspect, described herein is a method of modulating the activity of an orexin receptor, such as one or both of OX₁ or OX₂, comprising contacting a cell comprising the orexin receptor with an effective amount of at least one compound of Formula (I) or (II), or a pharmaceutically acceptable salt thereof, and/or with at least one compound or pharmaceutical composition as described herein. In certain embodiments of the foregoing, the contacting is in vitro, ex vivo, or in vivo.

Additional embodiments, features, and advantages of the invention will be apparent from the following detailed description and through practice of the embodiments described in this application.

DETAILED DESCRIPTION

In one aspect, the application provides a compound of Formula (I):

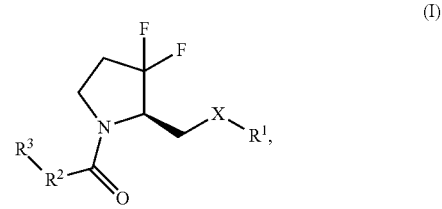

wherein
X is NR⁴, or O;
R¹ is a monocyclic or bicyclic heteroaryl, wherein R¹ is unsubstituted or substituted with one or more substituents independently selected from the group consisting of alkyl, such as C₁₋₄alkyl, haloalkyl, such as C₁₋₄ haloalkyl, halo, —OH, —O-alkyl, such as —OC₁₋₄alkyl, —CN, —NRᵃRᵇ, —N(Rᵃ)C(O)alkyl, such as —N(Rᵃ)C(O)C₁₋₄alkyl, —N(Rᵃ)CO₂alkyl, such as —N(Rᵃ)CO₂C₁₋₄alkyl, —N(Rᵃ)SO₂C₁₋₄alkyl, —C(O)alkyl, such as —C(O)C₁₋₄alkyl, —CO₂H, —CO₂alkyl, such as —CO₂C₁₋₄alkyl, —CONRᵃRᵇ, —SO₂alkyl, such as —SO₂C₁₋₄alkyl, and —SO₂NRᵃRᵇ; wherein Rᵃ and Rᵇ are each independently H or alkyl, such as C₁₋₄alkyl;

R² is phenyl or a monocyclic heteroaryl, wherein R² is unsubstituted or substituted with one or more substituents independently selected from the group consisting of alkyl, such as C₁₋₄alkyl, cycloalkyl, such as cyclopropyl, haloalkyl, such as C₁₋₄ haloalkyl, halo, —OH, —O-alkyl, such as —OC₁₋₄alkyl, —CN, —NRᶜRᵈ, —N(Rᶜ)C(O) alkyl, such as —N(Rᶜ)C(O)C₁₋₄alkyl, —N(Rᶜ)CO₂alkyl, such as —N(Rᶜ)CO₂C₁₋₄alkyl, —N(Rᶜ)SO₂alkyl, such as —N(Rᶜ)SO₂C₁₋₄alkyl, —C(O)alkyl, such as —C(O)C₁₋₄alkyl, —CO₂H, —CO₂alkyl, such as —CO₂C₁₋₄alkyl, —CONRᶜRᵈ, —SO₂alkyl, such as —SO₂C₁₋₄alkyl, and —SO₂NRᶜRᵈ; wherein Rᶜ and Rᵈ are each independently H or alkyl, such as C₁₋₄alkyl;

R³ is phenyl or a monocyclic heteroaryl, wherein R³ is unsubstituted or substituted with one or more substituents independently selected from the group consisting of alkyl, such as $C_{1-4}$alkyl, haloalkyl, such as $C_{1-4}$ haloalkyl, halo, —OH, —O-alkyl, such as —OC$_{1-4}$alkyl, —CN, —NR$^e$R$^f$, —N(R$^e$)C(O) alkyl, such as —N(R$^e$)C(O)C$_{1-4}$alkyl, —N(R$^e$)CO$_2$alkyl, such as —N(R$^e$)CO$_2$C$_{1-4}$alkyl, —N(R$^e$)SO$_2$C$_{1-4}$alkyl, —C(O)alkyl, such as —C(O)C$_{1-4}$alkyl, —CO$_2$H, —CO$_2$alkyl, such as —CO$_2$C$_{1-4}$alkyl, —CONR$^e$R$^f$, —SO$_2$alkyl, such as —SO$_2$C$_{1-4}$alkyl, and —SO$_2$NR$^e$R$^f$; wherein R$^e$ and R$^f$ are each independently H or alkyl, such as C$_{1-4}$alkyl; and $R^4$ is H or alkyl, such as $C_{1-4}$alkyl.

or a pharmaceutically acceptable salt thereof.

In certain embodiments, when one of $R^2$ and $R^3$ is phenyl, the other is not phenyl, and when one of $R^2$ and $R^3$ is heteroaryl, the other is not heteroaryl;

In some embodiments, X is NR$^4$. In certain such embodiments, $R^4$ is H. In other embodiments, X is NR$^4$ and $R^4$ is alkyl, such as $C_{1-4}$ alkyl.

In certain embodiments, X is O.

In some embodiments, $R^1$ is a monocyclic heteroaryl, such as pyrazinyl, pyrimidinyl, thiadiazolyl, or pyridinyl. In certain such embodiments, $R^1$ is pyrazinyl, pyrimidinyl, or pyridinyl, i.e., 2-pyrimidinyl or 2-pyridinyl. In certain such embodiments, $R^1$ is a 6-membered heteroaryl, such as pyrazinyl, pyrimidinyl or pyridinyl. In other embodiments, $R^1$ is a bicyclic heteroaryl, such as benzoxazolyl, i.e., 2-benzoxazolyl.

In some embodiments, $R^1$ is unsubstituted. In other embodiments, $R^1$ is substituted with one or more substituents independently selected from the group consisting of methyl, ethyl, propyl, isopropyl, butyl, —CF$_3$, —CHF$_2$, —CH$_2$F, —F, —Br, —Cl, —OH, methoxy, ethoxy, propoxy, —CN, —NH$_2$, —NHCH$_3$, —N(CH$_3$)$_2$, —NH-acetyl, —NHCO$_2$CH$_3$, —NHSO$_2$CH$_3$, acetyl, —CO$_2$H, —CO$_2$CH$_3$, —CONH$_2$, —SO$_2$CH$_3$, and —SO$_2$NHCH$_3$. In certain embodiments, $R^1$ is substituted with one or more substituents independently selected from the group consisting of alkyl, such as methyl, haloalkyl, such as —CF$_3$, and halo, such as —F, or —Cl.

In certain embodiments, $R^1$ is pyrimidinyl substituted with haloalkyl, such as —CF$_3$, or halo, such as —Cl. In certain such embodiments, $R^1$ is pyrimidinyl substituted with —CF$_3$, e.g.,

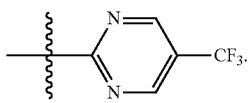

In certain such embodiments, $R^1$ is pyrimidinyl substituted with —Cl, e.g.,

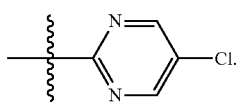

In other embodiments, $R^1$ is pyridinyl, substituted with haloalkyl, such as —CF$_3$, e.g.,

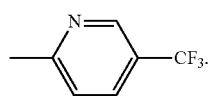

In yet other embodiments, $R^1$ is benzoxazolyl, unsubstituted or substituted with halo, such as —Cl or —F.

In certain embodiments, $R^2$ is phenyl or a monocyclic heteroaryl, wherein $R^2$ is unsubstituted or substituted with one or more substituents independently selected from the group consisting of alkyl, such as $C_{1-4}$alkyl, haloalkyl, such as $C_{1-4}$ haloalkyl, halo, —OH, —O-alkyl, such as —OC$_{1-4}$ alkyl, —CN, —NR$^c$R$^d$, —N(R$^c$)C(O) alkyl, such as —N(R$^c$)C(O)C$_{1-4}$alkyl, —N(R$^c$)CO$_2$alkyl, such as —N(R$^c$)CO$_2$C$_{1-4}$alkyl, —N(R$^c$)SO$_2$alkyl, such as —N(R$^c$)SO$_2$C$_{1-4}$ alkyl, —C(O)alkyl, such as —C(O)C$_{1-4}$alkyl, —CO$_2$H, —CO$_2$alkyl, such as —CO$_2$C$_{1-4}$alkyl, —CONR$^c$R$^d$, —SO$_2$alkyl, such as —SO$_2$C$_{1-4}$alkyl, and —SO$_2$NR$^c$R$^d$; wherein R$^c$ and R$^d$ are each independently H or alkyl, such as C$_{1-4}$alkyl.

In some embodiments, $R^2$ is phenyl. In other embodiments, $R^2$ is a monocyclic heteroaryl, such as pyridinyl or thiazolyl. In certain such embodiments, $R^2$ is a 5-membered heteroaryl, such as thiazolyl.

In some embodiments, $R^2$ is unsubstituted. In other embodiments, $R^2$ is substituted with one or more substituents independently selected from the group consisting of methyl, ethyl, propyl, isopropyl, cyclopropyl, butyl, —CF$_3$, —CHF$_2$, —CH$_2$F, —F, —Br, —Cl, —OH, methoxy, ethoxy, propoxy, —CN, —NH$_2$, —NHCH$_3$, —N(CH$_3$)$_2$, —NH-acetyl, —NHCO$_2$CH$_3$, —NHSO$_2$CH$_3$, acetyl, —CO$_2$H, —CO$_2$CH$_3$, —CONH$_2$, —SO$_2$CH$_3$, and —SO$_2$NHCH$_3$. In other embodiments, $R^2$ is substituted with one or more substituents independently selected from the group consisting of alkyl, such as methyl, haloalkyl, such as —CF$_3$, —CN, and halo, such as —F, and —Cl. In certain such embodiments, $R^2$ is substituted with one or two methyl or fluoro groups, such as two methyl groups, two fluoro groups, or one fluoro group and one methyl group.

In certain embodiments, $R^2$ is phenyl substituted with one or two alkyl, such as methyl, or halo, such as fluoro, groups. For example, $R^2$ is phenyl substituted with two methyl groups, two fluoro groups, or one fluoro group and one methyl group.

In certain embodiments, $R^2$ is thiazolyl substituted with alkyl, such as methyl.

In some embodiments, $R^3$ is phenyl. In other embodiments, $R^3$ is a monocyclic heteroaryl, such as triazolyl, pyrimidinyl, or pyrazolyl. In other embodiments, $R^3$ is a monocyclic heteroaryl, such as triazolyl, or pyrimidinyl. In certain embodiments, $R^3$ is a 5-membered heteroaryl, such as triazolyl. In other such embodiments, $R^3$ is a 6-membered heteroaryl such as pyrimidinyl.

In some embodiments, $R^3$ is unsubstituted. In other embodiments, $R^3$ is substituted with one or more substituents independently selected from the group consisting of methyl, ethyl, propyl, isopropyl, butyl, —CF$_3$, —CHF$_2$, —CH$_2$F, —F, —Br, —Cl, —OH, methoxy, ethoxy, propoxy, —CN, —NH$_2$, —NHCH$_3$, —N(CH$_3$)$_2$, —NH-acetyl, —NHCO$_2$CH$_3$, —NHSO$_2$CH$_3$, acetyl, —CO$_2$H, —CO$_2$CH$_3$, —CONH$_2$, —SO$_2$CH$_3$, and —SO$_2$NHCH$_3$. In other embodiments, $R^3$ is substituted with one or more substituents independently selected from the group consisting of alkyl, such as methyl, haloalkyl, such as —CF$_3$, and halo, such as —F, or —Cl. In certain such embodiments, $R^3$ is substituted with fluoro.

In certain embodiments, $R^3$ is phenyl substituted with fluoro, such as

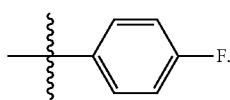

In certain embodiments, $R^3$ is unsubstituted triazolyl or pyrimidinyl.

In certain embodiments, when one of $R^2$ and $R^3$ is phenyl, the other is not phenyl.

In certain embodiments, when one of $R^2$ and $R^3$ is heteroaryl, the other is not heteroaryl.

In some embodiments, compounds of Formula (I) are compounds and pharmaceutically acceptable salts thereof, in which:

a) X is O or $NR^4$, wherein $R^4$ is H;

b) $R^1$ is pyridinyl, pyrimidinyl, or benzoxazolyl, each unsubstituted or substituted with haloalkyl, such as —$CF_3$, or halo, such as —Cl, or —F;

c) $R^2$ is phenyl or thiazolyl, each unsubstituted or substituted with one or two groups independently selected from alkyl, such as methyl, and halo, such as —F (e.g., two methyl groups, two fluoro groups, or one fluoro group and one methyl group); and d) $R^3$ is phenyl, unsubstituted or substituted with halo, such as —F; or $R^3$ is unsubstituted triazolyl, pyrimidinyl, or pyrazolyl, such as triazolyl or pyrimidinyl.

In some embodiments, compounds of Formula (I) are compounds and pharmaceutically acceptable salts thereof, in which:

a) X is O or NH;

b) $R^1$ is pyridinyl, pyrimidinyl, benzoxazolyl, pyrazinyl, or thiadiazolyl, such as pyridinyl, pyrimidinyl, benzoxazolyl, or pyrazinyl, each unsubstituted or substituted with haloalkyl, such as —$CF_3$, or halo, such as —Cl, or —F;

c) $R^2$ is phenyl, pyridinyl, or thiazolyl, each unsubstituted or substituted with one or two groups independently selected from alkyl, such as methyl, halo, such as —F or —Cl, haloalkyl, such as $CF_3$, and CN; and d) $R^3$ is phenyl, unsubstituted or substituted with halo, such as —F; or $R^3$ is a unsubstituted triazolyl, pyrimidinyl, or pyrazolyl, such as triazolyl or pyrimidinyl.

In some embodiments, compounds of Formula (I) can be represented by Formula (II):

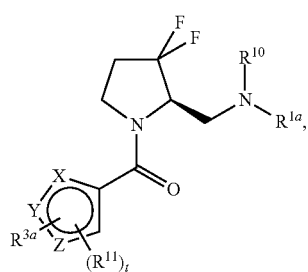

(II)

wherein $R^{10}$ is H or alkyl, such as $C_{1-4}$alkyl (e.g., methyl);

$R^{1a}$ is a 6-membered heteroaryl, unsubstituted or substituted with alkyl, such as $C_{1-4}$alkyl, haloalkyl, such as $C_{1-4}$ haloalkyl, or halo, such as —Cl, or —F;

wherein the ring system

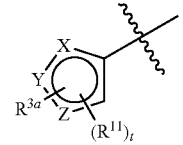

is selected from the group consisting of (a), (b), and (c):

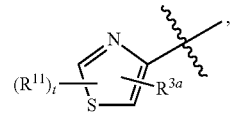
(a)

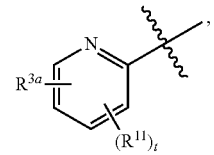
(b)

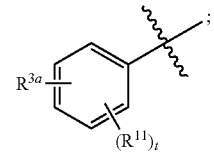
(c)

wherein each $R^{11}$ is independently selected from the group consisting of alkyl, such as $C_{1-4}$alkyl (e.g., methyl), cycloalkyl, such as cyclopropyl, —CN, halo, such as —Cl or —F, and alkoxy, such as $C_{1-4}$alkoxy (e.g., —$OCH_3$);

t is 0, 1, or 2; and $R^{3a}$ is phenyl or a monocyclic heteroaryl, unsubstituted or substituted with one or two substituents independently selected from the group consisting of alkyl, such as $C_{1-4}$alkyl, alkoxy, such as $C_{1-4}$alkoxy, halo, —CN, and haloalkyl, such as —$CF_3$;

or a pharmaceutically acceptable salt thereof.

In certain embodiments $R^{10}$ is H. In other embodiments, $R^{10}$ is alkyl, such as $C_{1-4}$alkyl (e.g., methyl).

In some embodiments, $R^{1a}$ is a pyrimidinyl or pyridinyl. In certain embodiments, $R^{1a}$ is unsubstituted or substituted with alkyl, such as $C_{1-4}$alkyl, haloalkyl, such as $C_{1-4}$ haloalkyl, or halo, such as chloro or fluoro. In certain embodiments $R^{1a}$ is a pyrimidinyl or pyridinyl substituted with haloalkyl, such as —$CF_3$, e.g.,

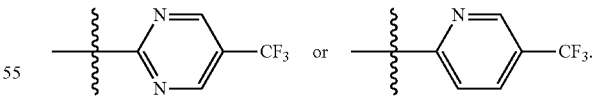

In some embodiments, the ring system

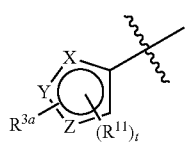

is represented by

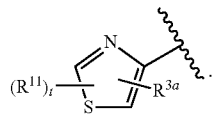

In other embodiments, the ring system

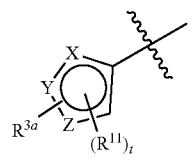

is represented by

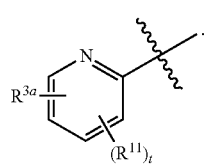

In yet other embodiments, the ring system

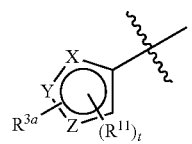

is represented by

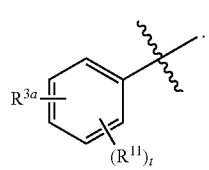

In certain embodiments, the ring system

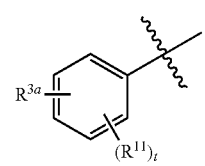

is represented by Formula (Xa) or (Xb)

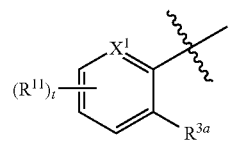
(Xa)

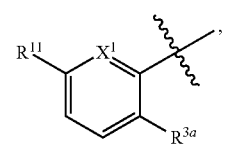
(Xb), wherein $X^1$ is CH or $CR^{11}$.

In certain embodiments, the ring system

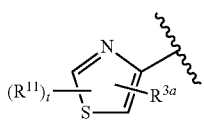
(a)

is represented by Formula (Xc)

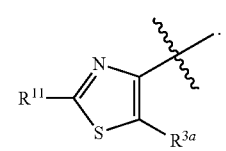
(Xc)

In certain embodiments, the ring system

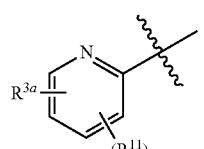
(b)

is represented by Formula (Xa) or (Xb):

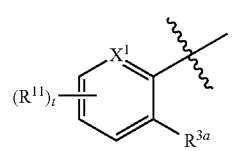
(Xa)

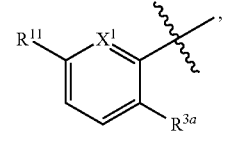
(Xb), wherein $X^1$ is N.

In certain embodiments, each $R^{11}$ is independently selected from the group consisting of alkyl, such as $C_{1-4}$alkyl (e.g., methyl), —CN, halo, such as —Cl or —F, and alkoxy, such as $C_{1-4}$alkoxy (e.g., —OCH$_3$). In some embodiments, each $R^{11}$ is independently selected from the group consisting of alkyl, such as methyl, halo, such as chloro or fluoro, and —CN. In certain such embodiments, $R^{11}$ is independently selected from the group consisting of chloro and fluoro.

In some embodiments, t is 0. In other embodiments, t is 1. In yet other embodiments, t is 2.

In some embodiments, $R^{3a}$ is optionally substituted phenyl. In other embodiments, $R^{3a}$ is optionally substituted monocyclic heteroaryl. In some embodiments, $R^{3a}$ is unsubstituted. In other embodiments, each $R^{3a}$ is independently selected from the group consisting of alkyl, such as methyl, ethyl, or isopropyl, alkoxy, such as methoxy, halo, such as —F, and haloalkyl, such as —CF$_3$.

In some embodiments, the ring system

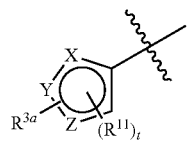

is selected from the group consisting of Formula (Xa), Formula (Xb), and Formula

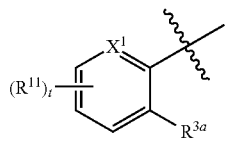 (Xa)

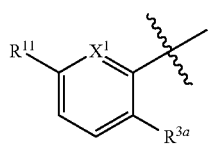 (Xb)

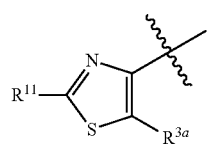 (Xc)

wherein $X^1$ is CH, $CR^{11}$, or N and $R^{3a}$ is as defined above. In some embodiments, $X^1$ is CH or $CR^{11}$. In other embodiments, $X^1$ is N. In other embodiments, the ring system

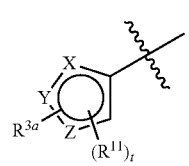

is represented by Formula (Xd):

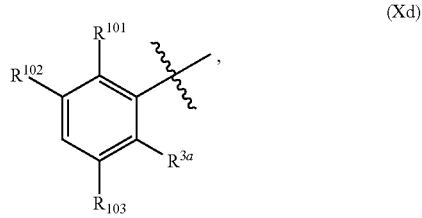 (Xd)

wherein (a) one of $R^{101}$ and $R^{103}$ is alkyl, such as methyl, or halo, such as chloro, or fluoro; the other of $R^{101}$ and $R^{103}$ is H; $R^{102}$ is H, and $R^{3a}$ is as defined above; or (b) $R^{102}$ is H or alkyl, such as chloro, or fluoro; and $R^{101}$ and $R^{103}$ are both H; and $R^{3a}$ is as defined above.

In some embodiments, the compound of Formula (I) or (II) is represented by a compound in Table 1.

TABLE 1

Compounds of Formulae I and II

| Ex. | Structure |
|---|---|
| 1 | 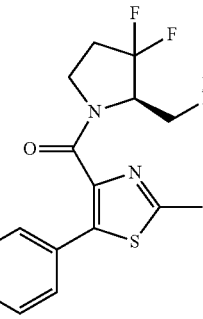 |
| 2 | 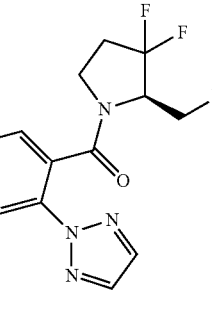 |
| 3 | 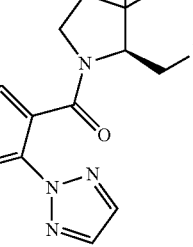 |

TABLE 1-continued

Compounds of Formulae I and II

| Ex. | Structure |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |

TABLE 1-continued

Compounds of Formulae I and II

| Ex. | Structure |
|---|---|
| 14 | 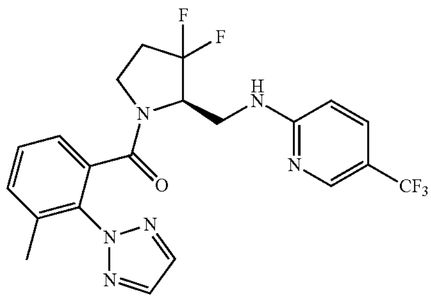 [SMILES: Cc1cccc(C(=O)N2CCC(F)(F)[C@H]2CNc2ccc(C(F)(F)F)cn2)c1-n1nccn1] |
| 15 | 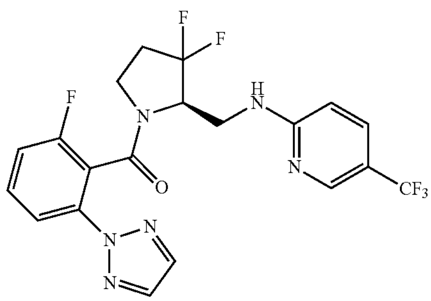 [SMILES: O=C(c1c(F)cccc1-n1nccn1)N1CCC(F)(F)[C@H]1CNc1ccc(C(F)(F)F)cn1] |
| 16 | 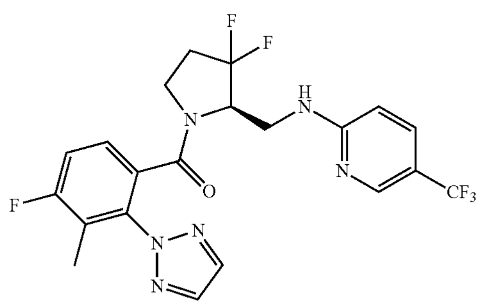 |
| 17 | 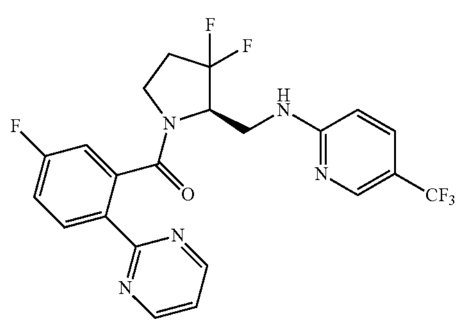 [SMILES: O=C(c1cc(F)ccc1-c1ncccn1)N1CCC(F)(F)[C@H]1CNc1ccc(C(F)(F)F)cn1] |
| 18 | 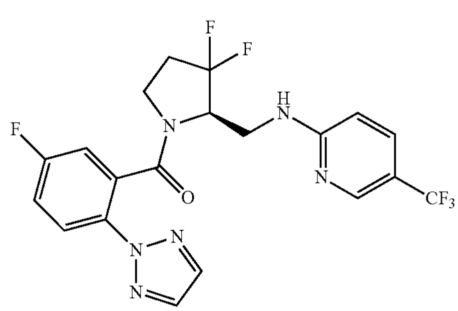 [SMILES: O=C(c1cc(F)ccc1-n1nccn1)N1CCC(F)(F)[C@H]1CNc1ccc(C(F)(F)F)cn1] |
| 19 | |
| 20 | |
| 21 | |
| 22 | |
| 23 | |

TABLE 1-continued

Compounds of Formulae I and II

| Ex. | Structure |
|---|---|
| 24 | 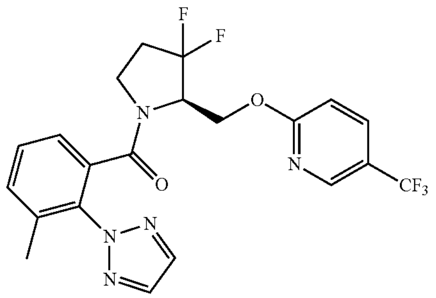 [SMILES: Cc1cccc(C(=O)N2CCC(F)(F)[C@H]2COc2ccc(C(F)(F)F)cn2)c1-n1nccn1] |
| 25 | 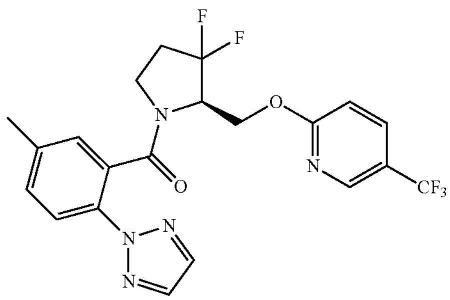 [SMILES: Cc1ccc(-n2nccn2)c(C(=O)N2CCC(F)(F)[C@H]2COc2ccc(C(F)(F)F)cn2)c1] |
| 26 | 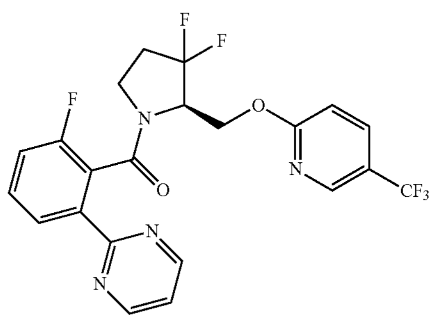 [SMILES: O=C(c1c(F)cccc1-c1ncccn1)N1CCC(F)(F)[C@H]1COc1ccc(C(F)(F)F)cn1] |
| 27 | 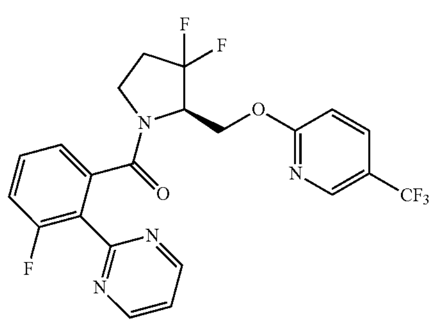 [SMILES: O=C(c1cccc(F)c1-c1ncccn1)N1CCC(F)(F)[C@H]1COc1ccc(C(F)(F)F)cn1] |
| 28 | 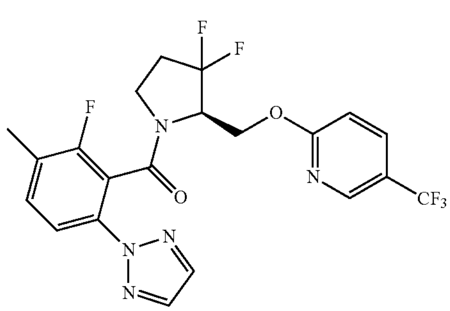 [SMILES: Cc1ccc(-n2nccn2)c(C(=O)N2CCC(F)(F)[C@H]2COc2ccc(C(F)(F)F)cn2)c1F] |
| 29 | |
| 30 | |
| 31 | |
| 32 | |
| 33 | |

TABLE 1-continued

Compounds of Formulae I and II

| Ex. | Structure |
|---|---|
| 34 | 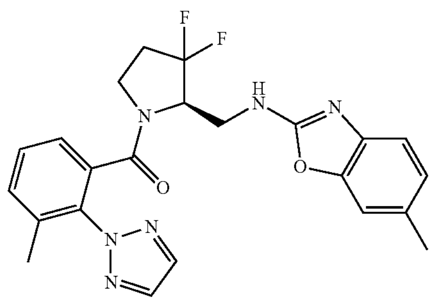 [SMILES: Cc1ccc2nc(NC[C@H]3N(C(=O)c4cccc(C)c4-n4nccn4)CCC3(F)F)oc2c1] |
| 35 | 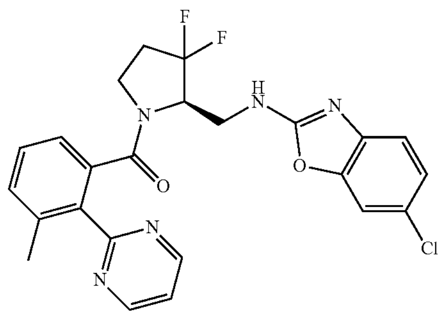 [SMILES: Cc1cccc(C(=O)N2CCC(F)(F)[C@H]2CNc2nc3ccc(Cl)cc3o2)c1-c1ncccn1] |
| 36 | 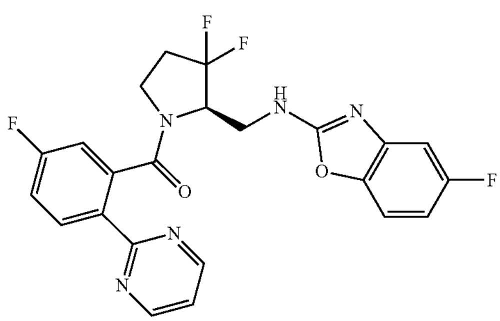 [SMILES: O=C(c1cc(F)ccc1-c1ncccn1)N1CCC(F)(F)[C@H]1CNc1nc2cc(F)ccc2o1] |
| 37 | 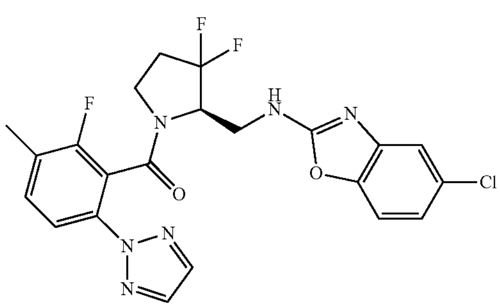 [SMILES: Cc1ccc(-n2nccn2)c(C(=O)N2CCC(F)(F)[C@H]2CNc2nc3cc(Cl)ccc3o2)c1F] |
| 38 | 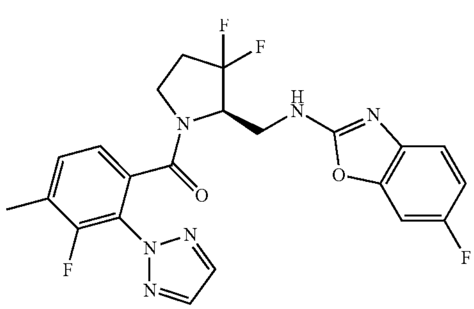 [SMILES: Cc1ccc(C(=O)N2CCC(F)(F)[C@H]2CNc2nc3ccc(F)cc3o2)c(-n2nccn2)c1F] |
| 39 | 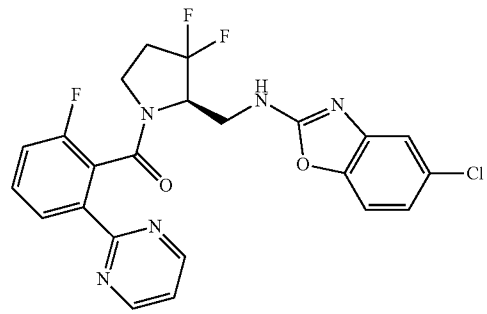 [SMILES: O=C(c1c(F)cccc1-c1ncccn1)N1CCC(F)(F)[C@H]1CNc1nc2cc(Cl)ccc2o1] |
| 40 | 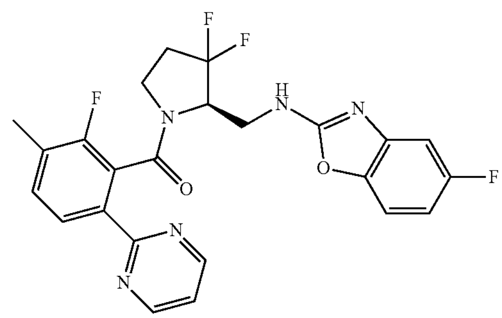 [SMILES: Cc1ccc(-c2ncccn2)c(C(=O)N2CCC(F)(F)[C@H]2CNc2nc3cc(F)ccc3o2)c1F] |
| 41 | 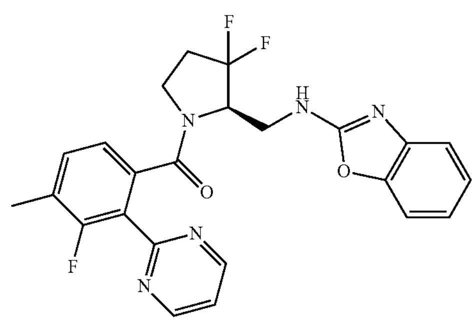 [SMILES: Cc1ccc(C(=O)N2CCC(F)(F)[C@H]2CNc2nc3ccccc3o2)c(-c2ncccn2)c1F] |
| 42 | 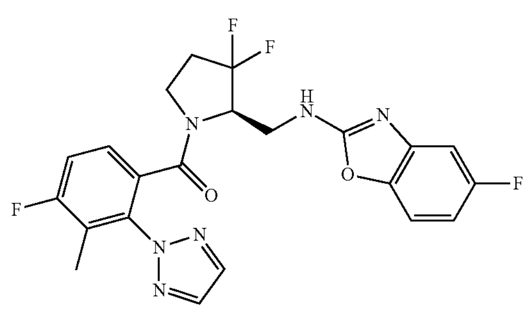 [SMILES: Cc1c(F)ccc(C(=O)N2CCC(F)(F)[C@H]2CNc2nc3cc(F)ccc3o2)c1-n1nccn1] |
| 43 | 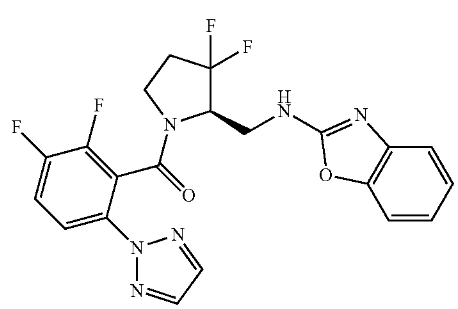 [SMILES: O=C(c1c(-n2nccn2)ccc(F)c1F)N1CCC(F)(F)[C@H]1CNc1nc2ccccc2o1] |

TABLE 1-continued

Compounds of Formulae I and II

| Ex. | Structure |
|---|---|
| 44 | 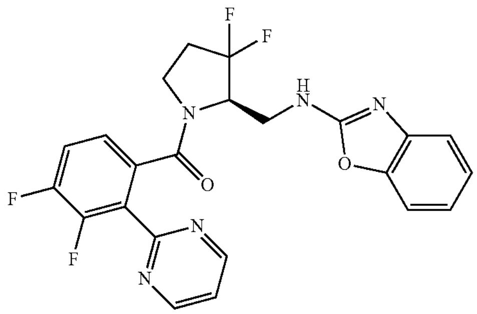 [SMILES: O=C(c1ccc(F)c(F)c1-c1ncccn1)N1CCC(F)(F)[C@H]1CNc1nc2ccccc2o1] |
| 45 | 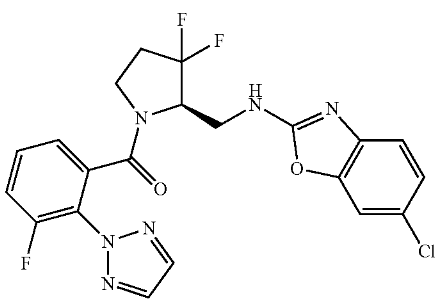 [SMILES: O=C(c1cccc(F)c1-n1nccn1)N1CCC(F)(F)[C@H]1CNc1nc2ccc(Cl)cc2o1] |
| 46 | 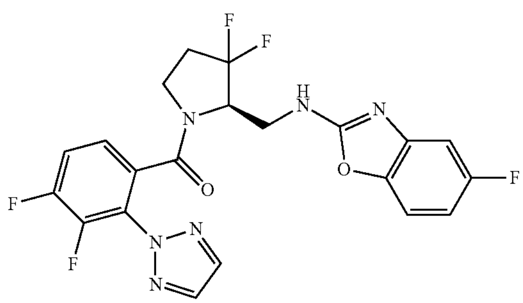 |
| 47 | 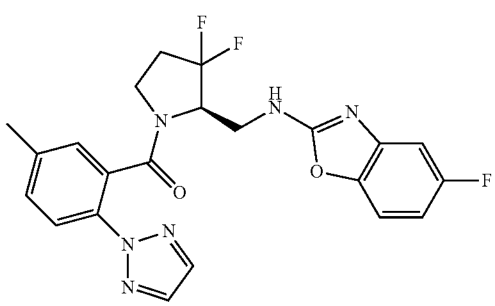 [SMILES: Cc1ccc(-n2nccn2)c(C(=O)N2CCC(F)(F)[C@H]2CNc2nc3cc(F)ccc3o2)c1] |
| 48 | 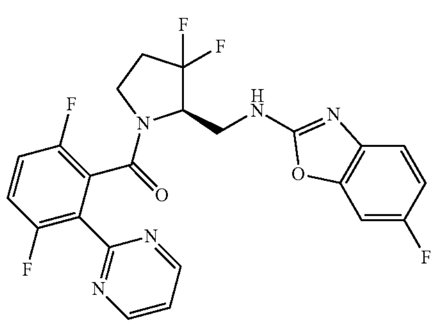 [SMILES: O=C(c1c(F)ccc(F)c1-c1ncccn1)N1CCC(F)(F)[C@H]1CNc1nc2ccc(F)cc2o1] |
| 49 | 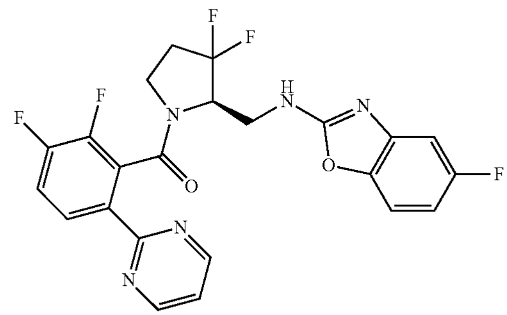 [SMILES: O=C(c1c(-c2ncccn2)ccc(F)c1F)N1CCC(F)(F)[C@H]1CNc1nc2cc(F)ccc2o1] |
| 50 | 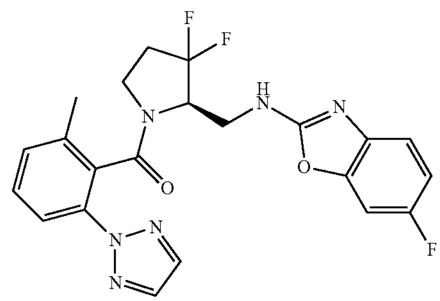 [SMILES: Cc1cccc(-n2nccn2)c1C(=O)N1CCC(F)(F)[C@H]1CNc1nc2ccc(F)cc2o1] |
| 51 | 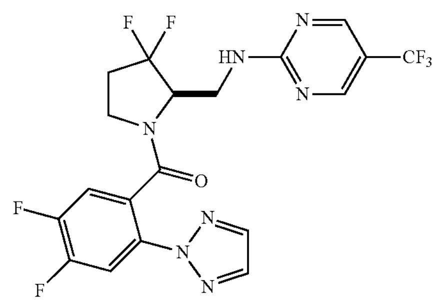 [SMILES: O=C(c1cc(F)c(F)cc1-n1nccn1)N1CCC(F)(F)[C@H]1CNc1ncc(C(F)(F)F)cn1] |
| 52 | 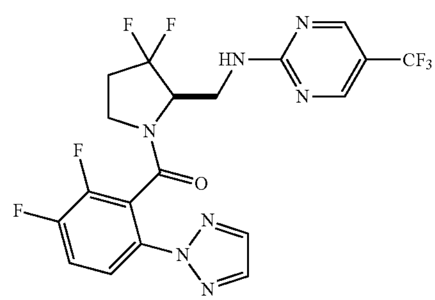 [SMILES: O=C(c1c(-n2nccn2)ccc(F)c1F)N1CCC(F)(F)[C@H]1CNc1ncc(C(F)(F)F)cn1] |
| 53 | 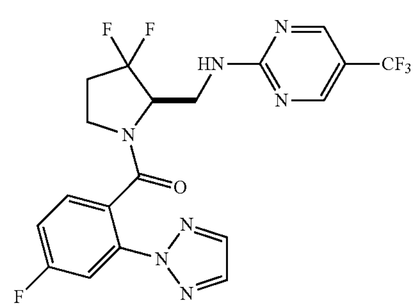 [SMILES: O=C(c1ccc(F)cc1-n1nccn1)N1CCC(F)(F)[C@H]1CNc1ncc(C(F)(F)F)cn1] |

TABLE 1-continued
Compounds of Formulae I and II
| Ex. | Structure |
|---|---|
| 54 | 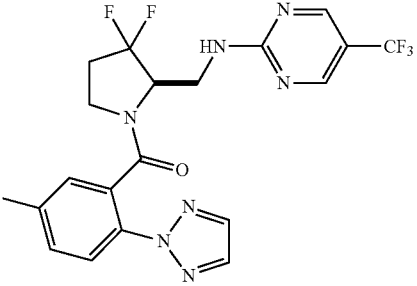 |
| 55 | 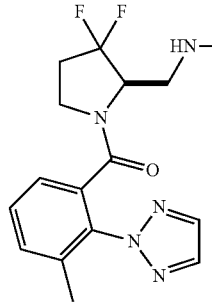 |
| 56 | 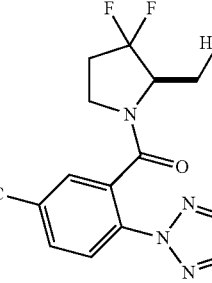 |
| 57 | 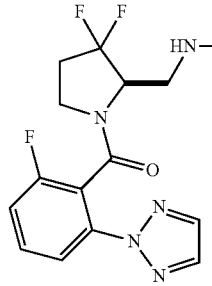 |
| 58 | 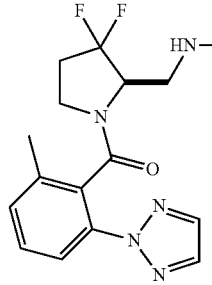 |
| 59 | 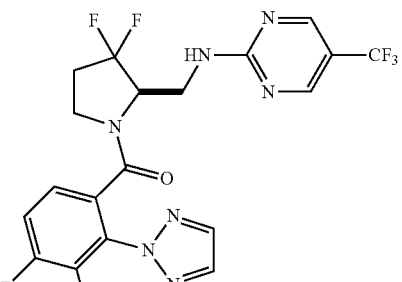 |
| 60 | 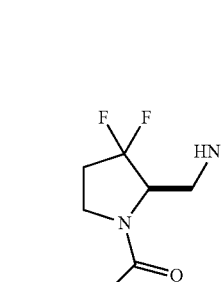 |
| 61 | 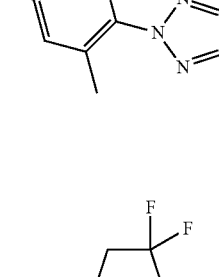 |
| 62 |  |

TABLE 1-continued

Compounds of Formulae I and II

| Ex. | Structure |
|---|---|
| 63 | (structure) |
| 64 | (structure) |
| 65 | (structure) |
| 66 | (structure) |
| 67 | (structure) |
| 68 | (structure) |
| 69 | (structure) |
| 70 | (structure) |
| 71 | (structure) |
| 72 | (structure) |

TABLE 1-continued

Compounds of Formulae I and II

| Ex. | Structure |
|---|---|
| 73 | (structure) |
| 74 | (structure) |
| 75 | (structure) |
| 76 | (structure) |
| 77 | (structure) |
| 78 | (structure) |
| 79 | (structure) |
| 80 | (structure) |
| 81 | (structure) |
| 82 | (structure) |

TABLE 1-continued

Compounds of Formulae I and II

| Ex. | Structure |
|---|---|
| 83 | (structure) |
| 84 | (structure) |
| 85 | (structure) |
| 86 | (structure) |
| 87 | (structure) |
| 88 | (structure) |
| 89 | (structure) |
| 90 | (structure) |
| 91 | (structure) | and pharmaceutically acceptable salts thereof.

Those skilled in the art will recognize that the species listed or illustrated herein are not exhaustive, and that additional species within the scope of these defined terms may also be selected.

Definitions

It is to be understood that the present description is not limited to particular embodiments described, as such may, of course, vary. It is also to be understood that the terminology used herein is for the purpose of describing particular embodiments only, and is not intended to be limiting, since the scope of the present application will be limited only by the appended claims. The definitions set forth in this application are intended to clarify terms used throughout this application.

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the embodiments in present application, the preferred methods and materials are now described. All publications, including patents, cited herein are incorporated by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

The nomenclature used herein to name the subject compounds is illustrated in the Examples herein. This nomenclature has generally been derived using the commercially-available ChemBioDraw Ultra software (Cambridgesoft/Perkin Elmer), Version 12.0.

It is appreciated that certain features of the application, which are, for clarity, described in the context of separate embodiments, may also be provided in combination in a single embodiment. Conversely, various features of the application, which are, for brevity, described in the context of a single embodiment, may also be provided separately or in any suitable subcombination. All combinations of the embodiments pertaining to the chemical groups represented by the variables are specifically embraced by the present application and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present application and are disclosed herein just as if each and every such sub-combination of chemical groups was individually and explicitly disclosed herein.

Any formula depicted herein is intended to represent a compound of that structural formula as well as certain variations or forms. For example, a formula given herein is intended to include a racemic form, or one or more enantiomeric, diastereomeric, or geometric isomers, or tautomeric forms, or a mixture thereof. Additionally, any formula given herein is intended to refer also to a solvate, such as a hydrate, solvate, or polymorph of such a compound, or a mixture thereof. Any formula given herein is intended to refer to amorphous and/or crystalline physical forms of the compound. The compounds described herein may be analytically pure, or a mixture in which the compound comprises at least 50%, at least 70%, at least 80%, at least 90%, at least 95%, or at least 98% by weight of the mixture.

In addition, where features or aspects of the embodiments of this application are described in terms of Markush groups, those skilled in the art will recognize that embodiments described herein is also thereby described in terms of any individual member or subgroup of members of the Markush group. For example, if X is described as selected from the group consisting of bromine, chlorine, and iodine, claims for X being bromine and claims for X being bromine and chlorine are fully described.

The term "herein" refers to the entire application.

As used herein, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

As used herein, "subject" (as in the subject of the treatment) refers to both mammals and non-mammals. Mammals include, for example, humans; non-human primates, e.g. apes and monkeys; and non-primates, e.g. mice, rats, rabbits, dogs, cats, cattle, horses, sheep, and goats. Non-mammals include, for example, worms, fish and birds. In some embodiments, the subject is a human.

"Substantially" as the term is used herein refers to being completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

The term "alkynyl", as used herein, refers to an aliphatic group containing at least one triple bond and is intended to include both "unsubstituted alkynyls" and "substituted alkynyls", the latter of which refers to alkynyl moieties having substituents replacing one or more hydrogens on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, such as from 1 to 12 carbon atoms, preferably from 1 to about 10, more preferably from 1 to 4, unless otherwise defined. Examples of straight chained and branched alkyl groups include methyl, ethyl, n-propyl, isopropyl, n-butyl, isobutyl, sec-butyl, tert-butyl, pentyl, isopentyl, tert-pentyl, hexyl, isohexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen or more hydrogens on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like. Exemplary substituted alkyls are described below. Cycloalkyls can be further substituted with alkyls, alkenyls, alkoxys, alkylthios, aminoalkyls, carbonyl-substituted alkyls, —CF3, —CN, and the like.

The term "(ATOM)$_{i-j}$" with j>i, when used in conjunction with a chemical moiety, such as, acyl, acyloxy, alkyl, alkenyl, alkynyl, or alkoxy is meant to include groups that contain from i to j (including i and j) atoms. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl refers to a hydrogen where the group is in a terminal position, a bond if internal. Similarly, for example, $C_{3-6}$cycloalkyl refers to a cycloalkyl as defined herein that has 3 to 6 carbon ring atoms. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The terms "amine" and "amino" are art-recognized and refer to both unsubstituted and substituted amines and salts thereof, e.g., a moiety that can be represented by

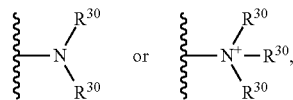

wherein each $R^{30}$ independently represents a hydrogen or a hydrocarbyl group, or two $R^{30}$ are taken together with the N atom to which they are attached complete a heterocycle having from 4 to 8 atoms in the ring structure.

The term "aminoalkyl", as used herein, refers to an alkyl group substituted with an amino group.

The term "amide", as used herein, refers to a group:

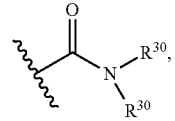

wherein each $R^{30}$ independently represent a hydrogen or hydrocarbyl group, or two $R^{30}$ are taken together with the N atom to which they are attached complete a heterocycle having from 4 to 8 atoms in the ring structure.

The term "halogen," or "halide" represents chlorine, fluorine, bromine, or iodine. The term "halo" represents chloro, fluoro, bromo, or iodo.

The term "haloalkyl" refers to an alkyl group with one or more halo substituents, or one, two, or three halo substituents. Examples of haloalkyl groups include —CF$_3$, —(CH$_2$)F, —CHF$_2$, —CH$_2$Br, —CH$_2$CF$_3$, and —CH$_2$CH$_2$F.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. The term "aralkyl", as used herein, refers to an alkyl group substituted with an aryl group.

The term "heteroaryl" refers to a monocyclic, fused bicyclic, or fused polycyclic aromatic heterocycle, having from 3 to 12 ring atoms per heterocycle, in which the ring atoms or members are selected from carbon atoms and up to four heteroatoms selected from nitrogen, oxygen, and sulfur. Illustrative examples of heteroaryl groups include the following entities, in the form of properly bonded moieties:

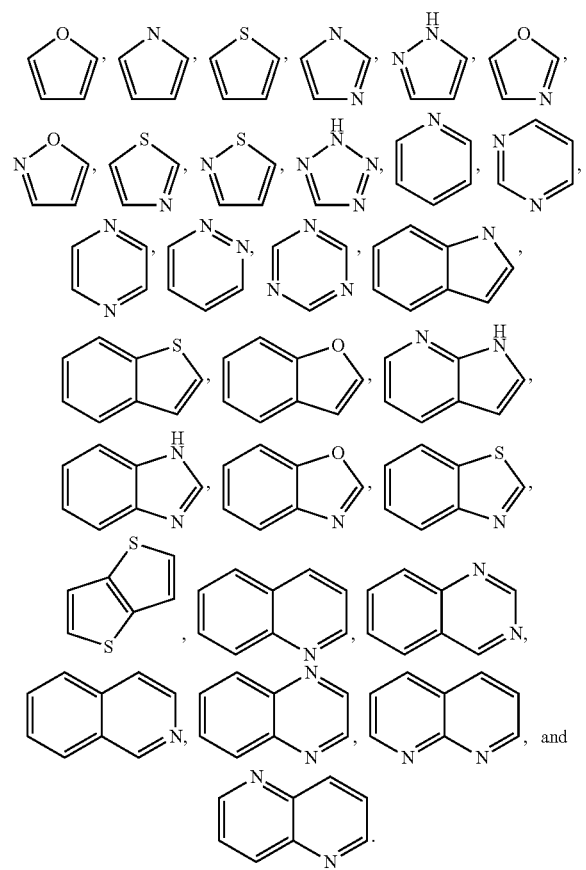

A "monocyclic" heteroaryl is an aromatic five- or six-membered heterocycle. A five-membered heteroaryl contains up to four heteroatom ring atoms, where (a) one ring atom is oxygen or sulfur and zero, one, or two ring atoms are nitrogen, or (b) zero ring atoms are oxygen or sulfur and up to four ring atoms are nitrogen. In some embodiments, a five-membered heteroaryl is furan, thiophene, pyrrole, oxazole, isoxazole, thiazole, isothiazole, pyrazole, imidazole, oxadiazole, thiadiazole, triazole, or tetrazole. A six-membered heteroaryl contains one, two, or three nitrogen ring atoms. In some embodiments, a six-membered heteroaryl is pyridine, pyrazine, pyrimidine, pyridazine, or triazine.

The term "heteroatom" as used herein refers to an atom of any element other than carbon or hydrogen. Exemplary heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "carbamate" is art-recognized and refers to a group

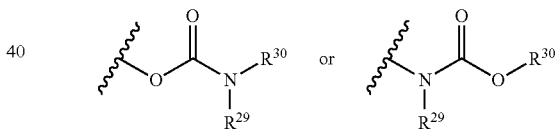

wherein $R^{29}$ and $R^{30}$ independently represent hydrogen or a hydrocarbyl group, such as an alkyl
group, or $R^{29}$ and $R^{30}$ taken together with the intervening atom(s) complete a heterocycle having
from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be susbstituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "carbocyclylalkyl", as used herein, refers to an alkyl group substituted with a carbocycle group.

The term "carbonate" is art-recognized and refers to a group —OCO$_2$—R$^{30}$, wherein R$^{30}$ represents a hydrocarbyl group.

The term "carboxy", as used herein, refers to a group represented by the formula —CO$_2$H.

The term "ester", as used herein, refers to a group —C(O)OR$^{30}$ wherein R$^{30}$ represents a hydrocarbyl group.

The term "ether," as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The term "substituted" refers to moieties having substituents replacing one or more hydrogens on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this application, the heteroatoms such as nitrogen may have hydrogen substituents and/or any permissible substituents of organic compounds described herein which satisfy the valences of the heteroatoms. In some embodiments, "substituted" means that the specified group or moiety bears one, two, or three substituents. In other embodiments, "substituted" means that the specified group or moiety bears one or two substituents. In still other embodiments, "substituted" refers to the specified group or moiety bears one substituent.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants. The term "unsubstituted" refers to that the specified group bears no substituents.

The term "sulfate" is art-recognized and refers to the group —OSO$_3$H, or a pharmaceutically acceptable salt thereof.

The term "sulfonamide" is art-recognized and refers to the group represented by the general formulae

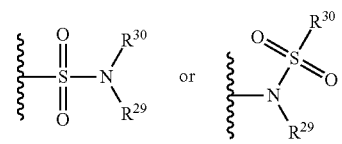

wherein R$^{29}$ and R$^{30}$ independently represents hydrogen or hydrocarbyl, such as alkyl, or R$^{29}$ and R$^{30}$ taken together with the intervening atom(s) complete a heterocycle having from 4 to 8 atoms in the ring structure.

The term "sulfoxide" is art-recognized and refers to the group —S(O)—R$^{30}$, wherein R$^{30}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{30}$, wherein R$^{30}$ represents a hydrocarbyl.

The term "thioalkyl", as used herein, refers to an alkyl group substituted with a thiol group.

The term "thioester", as used herein, refers to a group —C(O)SR$^{30}$ or —SC(O)R$^{30}$ wherein R$^{30}$ represents a hydrocarbyl.

The term "thioether", as used herein, is equivalent to an ether, wherein the oxygen is replaced with a sulfur.

The term "urea" is art-recognized and may be represented by the general formula

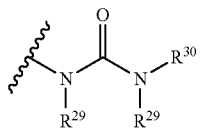

wherein R$^{29}$ and R$^{30}$ independently represent hydrogen or a hydrocarbyl, such as alkyl, or either occurrence of R$^{29}$ taken together with R$^{30}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The application also includes pharmaceutically acceptable salts of the compounds represented by Formula (I) or (II), preferably of those described above and of the specific compounds exemplified herein, and pharmaceutical compositions comprising such salts, and methods of using such salts.

A "pharmaceutically acceptable salt" is intended to mean a salt of a free acid or base of a compound represented herein that is non-toxic, biologically tolerable, or otherwise biologically suitable for administration to the subject. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound described herein that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The application also relates to pharmaceutically acceptable prodrugs of the compounds of described herein, or a pharmaceutically acceptable salt of the compound described herein, and treatment methods employing such pharmaceutically acceptable prodrugs.

The term "prodrug" is intended to encompass compounds which, under physiologic conditions, are converted into the therapeutically active agents of the present application, e.g., a compound of described herein. A common method for making a prodrug is to include one or more selected moieties which are hydrolyzed under physiologic conditions to yield the desired molecule. In certain embodiments, the prodrug is converted by an enzymatic activity of the host animal. For example, a prodrug with a nitro group on an aromatic ring could be reduced by reductase to generate the desired amino group of the corresponding active compound in vivo. In another example, functional groups such as a hydroxyl, carbonate, or carboxylic acid in the parent compound are presented as an ester, which could be cleaved by esterases. Additionally, amine groups in the parent compounds are presented in, but not limited to, carbamate, N-alkylated or N-acylated forms (Simplicio et al, "Prodrugs for Amines," Molecules, (2008), 13:519-547). In certain embodiments, some or all of the compounds of described herein in a formulation represented above can be replaced with the corresponding suitable prodrug.

A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present application also relates to pharmaceutically active metabolites of compounds described herein, and uses of such metabolites in the methods of the application. A "pharmaceutically active metabolite" refers to a pharmacologically active product of metabolism/biochemical modification of a compound described herein, e.g., a compound of of Formula (I) or (II) or salt thereof, under physiological conditions. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Compounds of formulae (I) and (II), as disclosed herein, can also exist as various "solvates" or "hydrates." A "hydrate" is a compound that exists in a composition with water molecules. The composition can include water in stoichiometic quantities, such as a monohydrate or a dihydrate, or can include water in random amounts. A "solvate" is a similar composition except that a solvent other that water, such as with methanol, ethanol, dimethylformamide, and the like replaces the water. For example, methanol or ethanol can form an "alcoholate," which can again be stoichiometic or non-stoichiometic. Mixtures of such solvates or hydrates can also be prepared. The source of such solvate or hydrate can be from the solvent of crystallization, inherent in the solvent of preparation or crystallization, or adventitious to such solvent The present application further embraces isolated compounds according to formula (I) or (II). The expression "isolated compound" refers to a preparation of a compound of formula (I) or (II), or a mixture of compounds according to formula (I) or (II), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or (II) or a mixture of compounds according to formula (I) or (II), which contains the named compound or mixture of compounds according to formula (I) or (II) in an amount of at least 10 percent by weight of the total weight. Preferably the preparation contains the named compound or mixture of compounds in an amount of at least 50% by weight of the total weight; more preferably at least 80% by weight of the total weight; and most preferably at least 90%, at least 95% or at least 98% by weight of the total weight of the preparation.

The compounds of the application and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Described Compounds

Tautomerism

Within the present application it is to be understood that a compound described herein or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the application encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

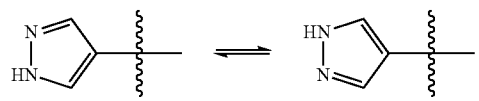 [SMILES: *c1cn[nH]c1 ; *c1cn[nH]c1]

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

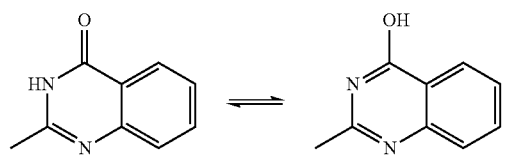

is an example of tautomerism. Accordingly, a structure depicted herein as one tautomer is intended to also include the other tautomer.

Optical Isomerism

It will be understood that when compounds of the present application contain one or more chiral centers, the compounds may exist in, and may be isolated as pure enantiomeric or diastereomeric forms or as racemic mixtures. The present application therefore includes any possible enantiomers, diastereomers, racemates or mixtures thereof of the compounds of the application.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

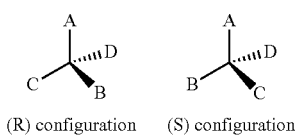

(R) configuration    (S) configuration

The present application is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

In certain embodiments, the therapeutic preparation may be enriched to provide predominantly one enantiomer of a compound (e.g., of formula (I) or (II)). An enantiomerically enriched mixture may comprise, for example, at least 60 mol percent of one enantiomer, or more preferably at least 75, 90, 95, or even 99 mol percent. In certain embodiments, a compound of the invention may have greater than 30% ee, 40% ee, 50% ee, 60% ee, 70% ee, 80% ee, 90% ee, or even 95% or greater ee. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, compounds of the application may have more than one stereocenter. In certain such embodiments, compounds of the application may be enriched in one or more diastereomer. For example, a compound of the application may have greater than 30% de, 40% de, 50% de, 60% de, 70% de, 80% de, 90% de, or even 95% or greater de.

Isolated optical isomers may be purified from racemic mixtures by well-known chiral separation techniques. According to one such method, a racemic mixture of a compound of the application, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Isolated optical isomers (enantiomerically pure compounds) can also be prepared by the use of chiral intermediates or catalysts in synthesis. When a chiral synthetic intermediate is used, the optical center (chiral center) can be preserved without racemization throughout the remainder of the preparative procedure, as is well known in the art. Chiral catalyst can be used to impart at least some degree of enantiomeric purity to products of reactions catalyzed by the chiral catalyst. And, in some cases, compounds having at least some degree of enantiomeric enrichment can be obtained by physical processes such as selective crystallization of salts or complexes formed with chiral adjuvants.

A variety of compounds in the present application may exist in particular geometric or stereoisomeric forms. The present application takes into account all such compounds, including tautomers, cis- and trans-isomers, R- and S-enantiomers, diastereomers, (D)-isomers, (L)-isomers, the racemic mixtures thereof, and other mixtures thereof, as being covered within the scope of this application. All tautomeric forms are encompassed in the present application. Additional asymmetric carbon atoms may be present in a substituent such as an alkyl group. All such isomers, as well as mixtures thereof, are intended to be included in this application, unless the stereochemistry or isomeric form is specifically indicated.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present application therefore includes any possible stable rotamers of formula (I) which are biologically active in the treatment of cancer or other proliferative disease states.

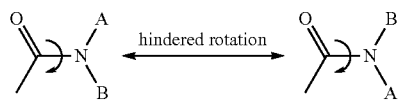

Regioisomerism

The preferred compounds of the present application have a particular spatial arrangement of substituents on the aromatic rings, which are related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

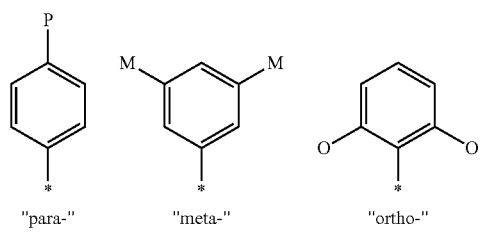

"para-"    "meta-"    "ortho-"

The present application further includes all pharmaceutically acceptable isotopically labeled compound (e.g., of formula (I) or (II)). An "isotopically" or "radio-labelled" compound is a compound where one or more atoms are replaced or substituted by an atom having an atomic mass or mass number different from the atomic mass or mass number typically found in nature (i.e., naturally occurring). For example, in certain embodiments, in compounds (e.g., of formula (I) or (II)), hydrogen atoms are replaced or substituted by one or more deuterium or tritium (e.g., hydrogen atoms on a $C_{1-6}$ alkyl or a $C_{1-6}$ alkoxy are replaced with deuterium, such as $d_3$-methoxy or 1,1,2,2-$d_4$-3-methylbutyl).

Certain isotopically labeled compounds (e.g., compounds of formula (I) or (II)), for example, those incorporating a radioactive isotope, are useful in drug and/or substrate tissue distribution studies. The radioactive isotopes tritium, i.e. $^3$H, and carbon 14, i.e., $^{14}$C, are particularly useful for this purpose in view of their ease of incorporation and ready means of detection.

Such isotopically labelled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^2$H) may afford certain therapeutic advantages resulting from greater metabolic stability, for example increased in vivo half-life or reduced dosage requirements.

Substitution with positron emitting isotopes, such as $^{11}$C, $^{18}$F, $^{15}$O, and $^{13}$N, can be useful in Positron Emission Topography (PET) studies for examining substrate receptor occupancy.

Isotopically labelled compounds (e.g., of formula (I) or (II)) or their corresponding prodrugs can generally be prepared by conventional techniques known to those skilled in the art or by processes analogous to those described in the accompanying examples using an appropriate isotopically labelled reagent in place of the non-labelled reagent previously employed. Suitable isotopes that may be incorporated in compounds of the present application include but are not limited to isotopes of hydrogen, carbon, nitrogen, oxygen, phosphorous, fluorine, chlorine, and iodine, such as $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, $^{131}$I, $^{31}$P, and $^{32}$P.

Isotopically labeled compounds of this application and prodrugs thereof can generally be prepared by carrying out the procedures disclosed in the schemes or in the examples and preparations described below by substituting a readily available isotopically labeled reagent for a non-isotopically labeled reagent.

Provisos may apply to any of the disclosed categories or embodiments such that specific embodiments or species may be excluded from such categories or embodiments.

In various embodiments, the compound or set of compounds, such as are used in the inventive methods, can be any one of any of the combinations and/or sub-combinations of the above-listed embodiments.

Pharmaceutical Compositions

The compositions and methods of the present application may be utilized to treat a subject, such as a mammal, e.g., human, or a non-human mammal, in need thereof. When administered to an animal, such as a human, the composition or the compound is preferably administered as a pharmaceutical composition comprising, for example, a compound of the application and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the application. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the application. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein refers to a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate;

(13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The compounds of the application, including their pharmaceutically acceptable salts and prodrugs, can also exist as various polymorphs, pseudo-polymorphs, or in amorphous state. As used herein, the term "polymorph" refers to different crystalline forms of the same compound and other solid state molecular forms including pseudo-polymorphs, such as hydrates, solvates, or salts of the same compound. Different crystalline polymorphs have different crystal structures due to a different packing of molecules in the lattice, as a result of changes in temperature, pressure, or variations in the crystallization process. Polymorphs differ from each other in their physical properties, such as x-ray diffraction characteristics, stability, melting points, solubility, or rates of dissolution in certain solvents. Thus crystalline polymorphic forms are important aspects in the development of suitable dosage forms in pharmaceutical industry.

Sterile compositions are also contemplated by the application, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the application may be administered by a suitable route of delivery, such as oral, parenteral, rectal, nasal, topical, or ocular routes, or by inhalation. Preferably, the compositions are formulated for intravenous or oral administration.

For oral administration, the compounds the application may be provided in a solid form, such as a tablet or capsule, or as a solution, emulsion, or suspension. To prepare the oral compositions, the compounds of the application may be formulated to yield a dosage of, e.g., from about 0.1 mg to about 2 g daily, or about 1 mg to about 1 g daily, or about 1 mg to about 50 mg daily, or about 10 mg to about 50 mg daily, or about 50 to about 250 mg daily, or about 250 mg to about 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. In addition, formulations of the pharmaceutical compositions for administration to the mouth may be presented as a mouthwash, or an oral spray, or an oral ointment. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

For parenteral use, including intravenous, intramuscular, intraperitoneal, intranasal, or subcutaneous routes, the agents of the application may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

Formulations which are suitable for vaginal administration also include pessaries, tampons, creams, gels, pastes, foams or spray formulations containing such carriers as are known in the art to be appropriate.

Alternatively or additionally, compositions can be formulated for delivery via a catheter, stent, wire, or other intraluminal device. Delivery via such devices may be especially useful for delivery to the bladder, urethra, ureter, rectum, or intestine.

For topical applications, the compounds of the present application are preferably formulated as creams or ointments or a similar vehicle suitable for topical administration. The inventive compounds may be mixed with a pharmaceutical carrier at a concentration of about 0.1% to about 10% of drug to vehicle. Another mode of administering the agents of the application may utilize a patch formulation to effect transdermal delivery. Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required. The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present application to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this application. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids. A preferred route of administration is local administration (e.g., topical administration, such as eye drops, or administration via an implant).

The compounds of the application are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day, or 25 to 200 mg per day, or 50 to 100 mg per day, or less than 100 mg per day. In choosing a regimen for a subject, such as a patient, it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the application are dispensed in unit dosage form including from about 0.05 mg to about 1000 mg of active ingredient together with a pharmaceutically acceptable carrier per unit dosage. In other embodiments, a unit dosage form includes from about 10 to about 200 mg of active ingredient.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent.

Dosage forms can be administered daily or more than once a day, such as twice or thrice daily. Alternatively dosage forms can be administered less frequently than daily, such as every other day, or weekly, if found to be advisable by a prescribing physician. In some embodiments, dosage forms are administered once or twice daily. Once improvement of the patient's disease has occurred, the dose may be adjusted for maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

As used herein, the terms "treat" or "treatment" includes "curative" treatment. "Curative" treatment is meant to include reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

In treatment methods according to the application, an "effective amount" refers to an amount or dose sufficient to generally bring about the desired therapeutic benefit or an amount sufficient to modulate the biological activity of the target receptor in subjects needing such treatment. Effective amounts or doses of the compounds of the application may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about from about 0.1 mg to about 2 g daily, or about 1 mg to about 1 g daily, or about 1 mg to about 50 mg daily, or about 10 mg to about 50 mg daily, or about 50 to about 250 mg daily, or about 250 mg to about 1 g daily. The total dosage may be given in single or divided dosage units (e.g., BID, TID, QID).

Methods

In various embodiments, compounds of the application can be used to modulate, such as to activate (agonist), or to block activation of (antagonist), an orexin receptor. Accordingly, in various embodiments, the application provides a method of modulating an orexin receptor comprising contacting the receptor with an effective amount or concentration of a compound of the application. The orexin receptor can be $OX_1$ or $OX_2$. In various embodiments, the compound of the application is an antagonist of an orexin receptor such as $OX_1$ or $OX_2$, or both, and can be a selective inhibitor of one or the other. In various embodiments, contacting can take place in vivo within tissues of a patient, such as a human patient. In various embodiments, modulation of an orexin receptor, for example, antagonism of orexin-1, by a compound of the application can be used to treat a disease, disorder, or medical condition in a patient, as described herein.

In various embodiments, the application provides a method of treating a disease, disorder, or medical condition in a patient wherein modulation of an orexin receptor is medically indicating, comprising administering to the subject, such as a patient, a compound of the application in a dose, at a frequency, and for duration to provide a beneficial effect to the subject. Modulation, such as agonism or antagonism, of an orexin receptor can be medically indicated in treatment of a disease, disorder, or medical condition wherein the orexin receptor plays a metabolic or regulatory role. Certain such conditions can be treated by selective modulation of a single class of orexin receptor, such as modulation of $OX_1$ while $OX_2$ is not influenced by administration of the compound of the application at the dose provided. In various embodiments, compounds of the application can be orexin-1 antagonists, and some of those are selective orexin-1 antagonists with respect to orexin-2. By "selective" is meant that one receptor is modulated at concentrations of the compound at least 10 times lower than the concentrations at which the comparative receptor is modulated by that compound. Accordingly, in various embodiments, the compound of the application can be a selective modulator, e.g., an antagonist, of orexin receptor $OX_1$. In other embodiments, the compound of the application can be a selective modulator (e.g., antagonist) of an orexin receptor $OX_2$. In further embodiments, the compound of the application can further modulate other types or classes of receptors having affinity for one of more forms of the orexin class of natural peptidic ligands.

In various embodiments, the application provides a use of a compound of the application for treatment of a disease, disorder, or medical condition in a patient. For example, a compound of the application can be used in the preparation of a medicament for administration to a patient suffering from a disease, disorder, or medical condition. More specifically, the disease, disorder, or medical condition can comprise an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, headache, migraine, pain, gastrointestinal diseases, epilepsy, inflammations, immune-related diseases, endocrine-related diseases, cancer, hypertension, behavior disorder, mood disorder, manic depression, dementia, sex disorder, psychosexual disorder, and renal disease. Drug or substance abuse or addiction includes relapse. These may include abuse of or addiction to cocaine, opiates, amphetamines, nicotine, alcohol, cannabis, heroin, and/or any other drug of abuse.

In other embodiments, the disease, disorder, or medical condition is narcolepsy, insomnia, learning disorders, memory disorders, depression, anxiety, addiction, obsessive compulsive disorder, affective neurosis, depressive neurosis, anxiety neurosis, dysthymic disorder, behavior disorder, mood disorder, sexual dysfunction, psychosexual dysfunction, sex disorder, schizophrenia, manic depression, delirium, dementia, severe mental retardation or dyskinesias (such as Huntington's Disease or Tourette Syndrome), eating disorders (such as anorexia, bulimia, cachexia, or obesity), addictive feeding behaviors, binge/purge feeding behaviors, cardiovascular diseases, diabetes, appetite/taste disorders, emesis, vomiting, nausea, asthma, cancer, Parkinson's Disease, Cushing's Syndrome/Disease, basophile adenoma, prolactinoma, hyperprolactinemia, hypophysis tumor/adenoma, hypothalamic diseases, inflammatory bowel disease, gastric dyskinesia, gastric ulcers, Froehlich's Syndrome, adrenohypophysis disease, hypophysis diseases, adrenohypophysis hypofunction, adrenohypophysis hyperfunction, hypothalamic hypogonadism, Kallman's syndrome (anosmia, hyposmia), functional or psychogenic amenorrhea, hypopituitarism, hypothalamic hypothyroidism, hypothalamic-adrenal dysfunction, idiopathic hyperprolactinemia, hypothalamic disorders of growth hormone deficiency, idiopathic growth deficiency, dwarfism, gigantism, acromegaly, disturbed biological and circadian rhythms, sleep disturbances associated with disease such as neurological disorders, neuropathic pain, diabetic neuropathy, and restless leg syndrome, heart and lung diseases, acute and congestive heart failure, hypotension, hypertension, urinary retention, osteoporosis, angina pectoris, myocardial infarction, ischemic or hemorrhagic stroke, subsrachnoic hemorrhage, ulcers, allergies, benign prostatic hypertrophy, chronic renal failure, renal disease, impaired glucose tolerance, migraine, episodic migraine, headache disorders (such as tension-type headache, cluster headache, other trigeminal autonomic cephalalgias, other primary headaches such as hemicranias continua, secondary headaches, cranial neuralgia, or central or primary facial pain), hyperalgesia, pain, enhanced or exaggerated sensitivity to pain such as hyperalgesia, causalgia, or allodynia, acute pain, burn pain, atypical facial pain, neuropathic pain, back pain, complex regional pain syndrome I or II, arthritic pain, sports injury pain, pain related to infection (e.g., HIV), post-chemotherapy pain, post-stroke pain, post-operative pain, neuralgia, emesis, nausea, vomiting, conditions associated with visceral pain (such as irritable bowel syndrome or angina), urinary bladder incontinence (e.g., urge incontinence), tolerance to narcotics or withdrawal from narcotics, sleep disorders, sleep apnea, parasomnia, jet lag syndrome, neurodegenerative disorders, disinhibition-dementia-parkinsonism-amyotrophy complex, pallido-ponto-nigral degeneration, epilepsy, seizure disorders, or other diseases related to general orexin system dysfunction.

In still other embodiments, the compounds described herein are useful in a method of treating disorders including, but not limited to, sleep disorders, sleep disturbances, including enhancing sleep quality, improving sleep quality, increasing sleep efficiency, augmenting sleep maintenance; increasing the ratio of the time that a subject sleeps relative to the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency, or duration of REM sleep bouts; altering the timing, frequency, or duration of slow wave (such as stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease, or cognitive impairment, as well as sleep walking and enuresis, and sleep disorders that accompany aging; Alzheimer's sundowning; conditions associated with circadian rhythmicity as well as mental and physical disorders associated with travel across time zones and with rotating shift-work schedules, conditions due to drugs that cause reductions in REM sleep as a side effect; fibromyalgia; syndromes that are manifested by non-restorative sleep and muscle pain; sleep apnea that is associated with respiratory disturbances during sleep; conditions that result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders including overeating and bulimia nervosa, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g., children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, such as obesity-related gastro-esophageal reflux, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis, or schizophrenia, as well as diseases or disorders where there is abnormal coupling of activity, particularly through the thalamus; enhancing cognitive function; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder, and cyclothymic disorder, mood disorders due to a general medical condition, and substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced mood disorders; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; substance-related disorders and addictive behaviors (including substance-induced delirium, persisting dementia, persisting amnestic disorder, psychotic disorder or anxiety disorder; tolerance, addictive feeding, dependence or withdrawal from substances including alcohol, amphetamines, cannabis, cocaine, hallucinogens, inhalants, nicotine, opioids, phencyclidine, sedatives, hypnotics, or anxiolytics); movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalized dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); attention deficit/hyperactivity disorder (ADHD); conduct disorder; migraine (including migraine headache); urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache.

In other embodiments, the disease, disorder, or medical condition is an eating disorder, obesity, alcoholism or an alcohol-related disorder, drug abuse or addiction, a sleep disorder, a cognitive dysfunction in a psychiatric or neurologic disorder, depression, anxiety, panic disorder, schizophrenia, Alzheimer's disease, Parkinson's disease, Huntington's chorea, headache, migraine, pain, gastrointestinal diseases, epilepsy, inflammations, immune-related diseases, ulcers, irritable bowel syndrome, diarrhea, gastroesophageal reflux, endocrine-related diseases, cancer, hypertension, behavior disorder, mood disorder, manic depression, dementia, sex disorder, psychosexual disorder, and renal disease.

In still other embodiments, the disease, disorder, or medical condition is substance addiction (including relapse), panic disorder, anxiety, post-traumatic stress disorder, pain, depression, seasonal affective disorder, an eating disorder, or hypertension.

Thus, in specific embodiments the present application provides methods for: enhancing the quality of sleep; augmenting sleep maintenance; increasing REM sleep; increasing stage 2 sleep; decreasing fragmentation of sleep patterns; treating insomnia; enhancing cognition; increasing memory retention; treating or controlling obesity; treating or controlling depression; treating, controlling, ameliorating or reducing the risk of epilepsy, including absence epilepsy; treating or controlling pain, including neuropathic pain; treating or controlling Parkinson's disease; treating or controlling psychosis; or treating, controlling, ameliorating or reducing the risk of schizophrenia, in a subject in need thereof which comprises administering to the patient a therapeutically effective amount of a compound of the present application.

It is believed that antagonism of orexin-1, in particular, is medically indicated for the treatment of the above-listed conditions. By antagonism is meant blocking a receptor, in this case an orexin receptor, without causing it to transduce a signal. That is, antagonism results in blocking an endogenous or exogenous ligand from activating, or causing antagonism, of the receptor.

It is within ordinary skill to evaluate any compound disclosed and claimed herein for effectiveness in modulation of an orexin receptor and in the various cellular assays using the procedures described above or found in the scientific literature. Accordingly, the person of ordinary skill can prepare and evaluate any of the claimed compounds without undue experimentation.

Any compound found to be an effective modulator, agonist or antagonist, can likewise be tested in animal models and in human clinical studies using the skill and experience of the investigator to guide the selection of dosages and treatment regimens.

In certain embodiments, the application comprises a method for conducting a pharmaceutical business, by determining an appropriate formulation and dosage of a compound of the application for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the application relates to a method for conducting a pharmaceutical business by determining an appropriate formulation and dosage of a compound of the application for treating or preventing any of the disease or conditions as described herein, and licensing, to a third party, the rights for further development and sale of the formulation.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

Drug Combinations

The inventive compounds described herein may be used in pharmaceutical compositions or methods in combination with one or more additional active ingredients in the treatment of the diseases and disorders described herein. Further additional active ingredients include other therapeutics or agents that mitigate adverse effects of therapies for the intended disease targets. Such combinations may serve to increase efficacy, ameliorate other disease symptoms, decrease one or more side effects, or decrease the required dose of an inventive compound. The additional active ingredients may be administered in a separate pharmaceutical composition from a compound of the present application or may be included with a compound of the present application in a single pharmaceutical composition. The additional active ingredients may be administered simultaneously with, prior to, or after administration of a compound of the present application. Actual dosage levels of the active ingredients in the pharmaceutical compositions may be varied so as to obtain an amount of the active ingredient that is effective to achieve the desired therapeutic response for a particular subject, such as a patient, composition, and mode of administration, without being toxic to the subject.

Combination agents include additional active ingredients are those that are known or discovered to be effective in treating the diseases and disorders described herein, including those active against another target associated with the disease. For example, compositions and formulations of the application, as well as methods of treatment, can further comprise other drugs or pharmaceuticals, e.g., other active agents useful for treating or palliative for the target diseases or related symptoms or conditions. For example, additional active ingredients include those that are known to be useful for enhancing sleep quality and preventing and treating sleep disorders and sleep disturbances, anti-diabetic agents, cardiovascular therapies, anti-obesity agents, other orexin receptor antagonists, pain medications, anti-depressants, anti-anxiety agents, cognition-enhancing agents, anti-Alzheimer's Disease therapies, and other active ingredients. Exemplary active pharmaceutical ingredients and other therapies that are suitable for combination with the presently described compounds include those listed in PCT Publ. No. WO2008/147518 at pages 23-29, which is hereby incorporated by reference. The pharmaceutical compositions of the any compound described herein may additional comprise one or more of such active agents, and methods of treatment may additionally comprise administering an effective amount of one or more of such active agents.

EXAMPLES

The following examples are offered to illustrate but not to limit the application. One of skill in the art will recognize that the following synthetic reactions and schemes may be modified by choice of suitable starting materials and reagents in order to access other compounds of Formula (I) or (II). Additional suitable methods and synthetic intermediates are described in PCT Publication No. WO2013/119639.

Example 1

Synthetic Protocols

Exemplary chemical entities useful in methods of the application will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I) or (II). Isotopically labeled compounds as described herein are prepared according to the methods described below, using suitably labeled starting materials. Such materials are generally available from commercial suppliers of radiolabeled chemical reagents.

Terms and Abbreviations:
ACN acetonitrile;
aq aqueous;
Atm atmospheric pressure;
Boc t-butoxycarbonyl;
Borax di-sodium tetraborate or sodium borate or sodium tetraborate;
Cbz benzyloxycarbonyl;
CDI 1,1'-carbonyldiimidazole;
dba dibenzylideneacetone;
DCM dichloromethane;
DEA diethylamine;
DIBAL-H diisobutylaluminium hydride;
DIPEA diisopropylethylamine;
DME 1,2-dimethoxyethane;
DMF N,N-dimethyl formamide;
DMSO dimethyl sulfoxide;
$Et_2O$ diethyl ether;
EtOAc ethyl acetate;
EtOH ethanol;
eq. or equiv. equivalent;
h hour(s);
HATU 2-(7-aza-1H-benzotriazole-1-yl)-1,1,3,3-tetramethyluronium hexafluorophosphate;
HBTU O-benzotriazole-N,N,N',N'-tetramethyluronium hexafluorophosphate
HPLC high performance liquid chromatography;
LCMS liquid chromatography mass spectrometry;
LDA lithium diisopropylamide;
LiHMDS lithium bis(trimethylsilyl)amide;
MeOH methanol;
min minute(s);
MS mass spectrometry;
MW microwave(s);
$NH_4OAc$ ammonium acetate;
NMR nuclear magnetic resonance;
ox oxidation;
Psi pounds per square inch;
quant. quantitative;
RCM ring closing metathesis;
r.t. room temperature;
sat. saturated;
SFC supercritical fluid chromatography;
T3P propylphosphonic anhydride;
TFA trifluoroacetic acid;
THF tetrahydrofuran;
TLC thin layer chromatography;
TMEDA tetramethylethylenediamine;
UPLC ultra performance liquid chromatography.

Synthesis of Compounds (a)-(z) and (aa)-(aj)

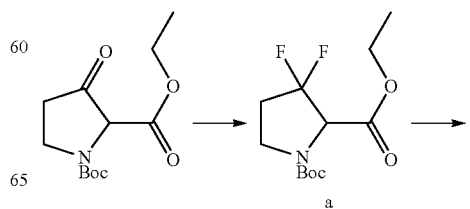

Scheme 1

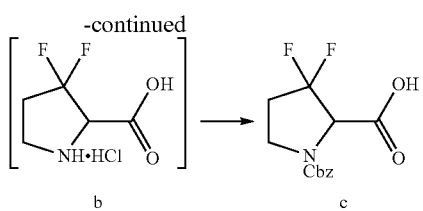

Compound (a): 1-(tert-butyl) 2-ethyl 3,3-difluoropyrrolidine-1,2-dicarboxylate. To ethyl N-Boc-3-oxopyrrolidine-2-carboxylate (6.5 g, 25.26 mmol, 1 equiv) under argon at 0° C. was added DAST (10.0 mL, 75.79 mmol, 3 equiv). The resulting solution was allowed to warm to 25° C. overnight. The reaction was cooled to 0° C. and DCM was added followed by the dropwise addition of a saturated aqueous solution of NaHCO$_3$. After allowing the mixture to stir for several minutes, the resulting biphasic solution was separated. The aqueous layer was extracted with DCM (2×). The combined organic layers were washed with brine, dried (Na$_2$SO$_4$) and concentrated. The resulting oil was purified by flash chromatography on silica gel (hexane/EtOAc) to afford the title compound as colorless oil (4.51 g, 16.16 mmol, 64% yield). $^1$HNMR (400 MHz, CDCl$_3$) δ=4.53-4.36 (m, 1H), 4.34-4.16 (m, 2H), 3.81-3.68 (m, 1H), 3.58-3.47 (m, 1H), 2.56-2.27 (m, 2H), 1.45-1.40 (2×s, 9H), 1.35-1.24 (m, 3H); $^{13}$C NMR (101 MHz, CDCl$_3$) δ=167.3, 167.2, 153.6, 153.1, 129.1, 126.5, 125.9, 124.0, 123.4, 81.0, 80.9, 65.4, 65.1, 65.1, 64.9, 64.8, 64.6, 64.2, 61.9, 61.8, 43.3, 43.3, 42.8, 42.7, 33.5, 33.3, 33.1, 32.9, 32.7, 32.4, 28.2, 28.1, 14.1, 14.0; $^{19}$F NMR (376 MHz, CDCl$_3$-d) δ=(−94.06)–(−95.08) (m, 1F), (−106.16)–(−108.24) (m, 1F). IR: 1750, 1705, 1391, 1368, 1208, 1159, 1132, 1092 cm$^{-1}$; HRMS (ESI) m/z [M+Na$^+$] calcd for C$_{12}$H$_{19}$F$_2$NNaO$_4$, 302.1180; found, 302.1180.

Compound (c): 1-((benzyloxy)carbonyl)-3,3-difluoropyrrolidine-2-carboxylic acid. A solution of 1-(tert-butyl) 2-ethyl 3,3-difluoropyrrolidine-1,2-dicarboxylate, Compound (a), (2.45 g, 8.76 mmol, 1 equiv) in 6 N HCl (90 mL) was stirred for 5 h at 60° C. Concentration of the solution give a light brown residue corresponding to 3,3-difluoro-DL-proline (Compound (b)) which was used without purification. The $^1$H NMR of the obtained compound (Compound (b)) corresponded to the $^1$H NMR of the 3,3-difluoro-DL-proline (Compound (b)) previously described by Shi, G.-Q.; Cai, W.-L. J. Org. Chem. 1995, 60, 6289. The obtained residue was solubilized in THF (30 mL) and H$_2$O (30 mL) and cooled with an ice-bath followed by the addition of NaHCO$_3$ (2.95 g, 35.06 mmol, 4 equiv) and benzyl chloroformate (2.75 mL, 19.28 mmol, 2.2 equiv). The resulting solution was stirred 24 h at rt and then concentrated in vacuo to remove the THF. The aqueous layer was washed with EtOAc (which was discarded) and then acidified to pH=1 with 1 N HCl and extracted with EtOAc (2×). The organic layers were washed with brine, dried over Na$_2$SO$_4$ and concentrated to afford a light yellow solid (2.03 g, 7.12 mmol, 81% yield overall). $^1$H NMR (400 MHz, CDCl$_3$) δ=8.65 (br. s., 1H), 7.42-7.28 (m, 5H), 5.24-5.12 (m, 2H), 4.61 (t, J=17.1 Hz, 1H), 3.89-3.78 (m, 1H), 3.73-3.61 (m, 1H), 2.62-2.33 (m, 2H); $^{13}$C NMR (101 MHz, CDCl$_3$) δ=171.4, 170.6, 154.6, 154.0, 135.7, 135.5, 128.5, 128.5, 128.3, 128.1, 128.0, 127.9, 127.8, 126.2, 125.5, 123.7, 123.0, 68.0, 67.9, 65.0, 64.9, 64.6, 64.3, 43.4, 43.3, 33.3, 33.1, 32.8, 32.6, 32.4; $^{19}$F NMR (376 MHz,CDCl$_3$) δ=(−93.99)–(−95.09) (m, 1F), (−105.45)–(−107.54) (m, 1F). IR: 2948, 1770, 1667, 1438, 1366, 1351, 1185, 1102 cm$^{-1}$; mp 110-112° C.; HRMS (ESI) m/z [M+H$^+$] calcd for C$_{13}$H$_{14}$F$_2$NO$_4$, 286.0885; found, 286.0694.

Scheme 2

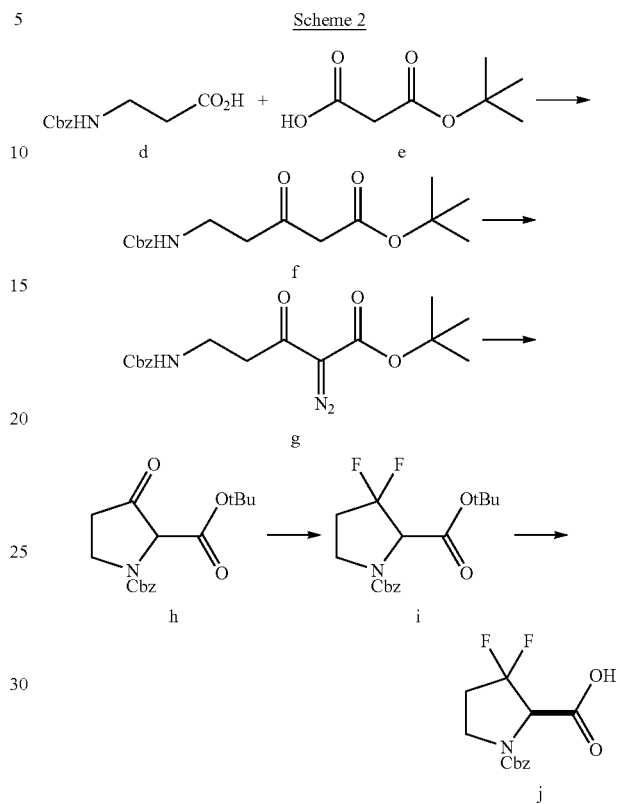

Compound (f): tert-butyl 5-(((benzyloxy)carbonyl)amino)-3-oxopentanoate. To a solution of commercially available Cbz-β-Ala-OH, Compound (d), (15.0 g, 67.24 mmol, 1 equiv) in 180 mL of THF was added CDI (13.08 g, 80.69 mmol, 1.2 equiv) and the resulting solution was stirred for 18 h at 25° C. In a separate flask, 3-(tert-butoxy)-3-oxopropanoic acid, Compound (e), (1.61 g, 100.86 mmol, 1.5 equiv) was treated with isopropylmagnesium chloride (2 M in THF, 202 mL, 3 equiv) at 0° C. for 30 min, then 30 min at rt and 30 min at 40° C. to generate the dianion. The activated acid of Compound (d) (the first solution) was then added dropwise to a 0° C. solution of the dianion. A precipitated start to form, and after warming to 25° C., the mixture was stirred for 4 h. The resulting mixture was quenched with an ice cooled aqueous 1 M H$_3$PO$_4$ solution and then extracted three times with EtOAc. The combined organics were washed with saturated NaHCO$_3$, brine, dried (Na$_2$SO$_4$) and concentrated to afford a colorless oil (20.62 g, 64.20 mmol, 95% yield) which was used without further purification in the next step. $^1$H NMR (400 MHz, CDCl$_3$) δ=7.34-7.23 (m, 5H), 5.21 (br. s., 1H), 5.00 (s, 2H), 3.40-3.35 (m, 2H), 3.27 (s, 2H), 2.71 (t, J=5.6 Hz, 2H), 1.38 (s, 9H); $^{13}$C NMR (101 MHz, CDCl$_3$) δ=202.7, 166.0, 156.3, 136.4, 128.5, 128.5, 128.1, 128.0, 82.2, 66.6, 50.6, 42.7, 35.4, 27.9 IR: 3350, 2979, 1706, 1515, 1248, 1144; HRMS (ESI) m/z [M+Na$^+$] calcd for C$_{17}$H$_{23}$NNaO$_5$, 344.1474; found, 344.1470.

Compound (g): tert-butyl 5-(((benzyloxy)carbonyl)amino)-2-diazo-3-oxopentanoate. 3-carboxybenzenesulfonyl azide (13.50 g, 59.45 mmol, 1.1 equiv) is added to a solution of β-keto ester Compound (f) (17.36 g, 54.05 mmol, 1 equiv) in CH₃CN (250 mL) under argon at 25° C. $^{13}$Triethylamine (23 mL, 162.15 mmol, 3 equiv) is added dropwise and the resulting solution is stirred for 2 h at 25° C. and then concentrated in vacuo. The crude residue was extracted with diethyl ether, washed with water, saturated NaHCO₃, saturated NH₄Cl, dried over Na₂SO₄ and concentrated in vacuo to give the diazo β-keto ester, Compound (g), as a colorless oil (17.83 g, 51.36 mmol, 95%) which was used without further purification. $^1$H NMR (400 MHz, CDCl₃) δ=7.37-7.28 (m, 5H), 5.36 (br. s., 1H), 5.07 (s, 2H), 3.53-3.478 (m, 2H), 3.04 (t, J=5.7 Hz, 2H), 1.52 (s, 9H); $^{13}$C NMR (101 MHz, CDCl₃) δ=191.9, 160.2, 156.2, 136.5, 128.4, 127.9, 127.9, 83.3, 66.5, 40.4, 35.9, 28.2 IR: 3351, 2978, 2130, 1706, 1645, 1513, 1312, 1247, 1213, 1130; HRMS (ESI) m/z [M+Na⁺] calcd for $C_{17}H_{21}N_3NaO_5$, 370.1379; found, 370.1375.

Compound (h):1-benzyl 2-(tert-butyl) 3-oxopyrrolidine-1,2-dicarboxylate. To a solution of the crude diazo β-keto ester, Compound (g) (17.5 g, 50.41 mmol, 1 equiv) in toluene (500 mL) was added Rh₂(OAc)₄ (111 mg, 0.252 mmol, 0.005 equiv). The mixture was stirred for 1 h at 90° C. under argon and then concentrated in vacuo. The crude residue was diluted with diethyl ether and filtered trough Celite®. The resulting filtrate was concentrated to afford 1-benzyl 2-(tert-butyl) 3-oxopyrrolidine-1,2-dicarboxylate, Compound (h), as a yellow solid (14.65 g, 45.87 mmol, 91%). Compound (h) could be used without further purification. $^1$H NMR (400 MHz, CHLOROFORM-d) δ=7.44-7.28 (m, 5H), 5.30-5.09 (m, 2H), 4.53-4.43 (m, 1H), 4.06-3.91 (m, 1H), 3.91-3.79 (m, 1H), 2.72-2.65 (m, 2H), 1.48-1.37 (m, 9H); $^{13}$C NMR (101 MHz, CDCl₃) δ=204.4, 203.9, 164.9, 164.8, 154.6, 154.6, 136.1, 135.8, 128.5, 128.4, 128.2, 128.1, 128.0, 127.9, 83.3, 83.2, 67.5, 66.2, 66.0, 42.1, 36.8, 36.1, 27.8, 27.7; IR: 1766, 1735, 1701, 1402, 1152, 1100; mp 54-56° C.; HRMS (ESI) m/z [M+Na⁺] calcd for $C_{17}H_{21}NNaO_5$, 342.1317; found, 342.1320.

Compound (i):1-benzyl 2-(tert-butyl) 3,3-difluoropyrrolidine-1,2-dicarboxylate. To a 0° C. solution of 1-benzyl 2-(tert-butyl) 3-oxopyrrolidine-1,2-dicarboxylate Compound (h) (22.5 g, 70.45 mmol, 1 equiv) in dry DCM (70 mL) was added DAST (28 mL, 211.35 mmol, 3 equiv). The solution was allowed to warm to 25° C. overnight. The reaction was carefully quenched by the addition of a saturated aqueous solution of NaHCO₃ at 0° C. After allowing the mixture to stir for several minutes, the resulting biphasic solution is separated. The aqueous layer was extracted with DCM (2×). The combined organic layers were washed with brine, dried (Na₂SO₄) and concentrated. The resulting oil was purified by flash chromatography on silica gel (hexane/EtOAc): 97/3 to afford the title compound as a colorless oil (17.08 g, 50.06 mmol, 71% yield). $^1$H NMR (400 MHz, CDCl₃) δ=7.41-7.28 (m, 5H), 5.24-5.05 (m, 2H), 4.51-4.38 (m, 1H), 3.88-3.76 (m, 1H), 3.69-3.56 (m, 1H), 2.59-2.29 (m, 2H), 1.50-1.37 (2s, 9H); $^{13}$C NMR (101 MHz, CDCl₃) δ=166.0, 165.9, 154.2, 153.9, 136.1, 135.9, 128.5, 128.4, 128.2, 128.1, 128.0, 127.8, 127.7, 126.6, 124.1, 83.1, 83.0, 67.5, 65.7, 65.5, 65.4, 65.2, 64.9, 43.3, 43.3, 33.2, 32.7, 32.5, 32.2, 27.8, 27.6 $^{19}$F NMR (376 MHz, CDCl₃) δ=(−93.64)−(−94.68) (m, 1F), (−106.55)−(−108.42) (m, 1F). IR: 1743, 1712, 1412, 1348, 1156, 1125, 1089; HRMS (ESI) m/z [M+Na⁻] calcd for $C_{17}H_{21}F_2NNaO_4$, 364.1336; found, 364.1337.

Compound (j): (R)-1-((benzyloxy)carbonyl)-3,3-difluoropyrrolidine-2-carboxylic acid. To a solution of 1-benzyl 2-(tert-butyl) 3,3-difluoropyrrolidine-1,2-dicarboxylate (Compound (i)) in CH₂Cl₂ was added TFA (1:1 v/v). The solution was aged at room temperature until starting material was consumed as judged by reverse-phase analytical HPLC analysis. The reaction was then concentrated in vacuo to give a dark oil. The crude acid was azeotroped with toluene, and used without further purification. To a solution of the crude acid (4.45 g, 15.6 mmol, 1 equiv) in iPrOH (120 mL) was added D-Tyrosine hydrazide (1.83 g, 9.36 mmol, 0.6 equiv) (See, Kudelko, A.; Zielinski, W.; Ejsmont, K. *Tetrahedron*, 2011, 67, 7838). This mixture was warmed to ~95° C. Enough MeOH (250 mL) was added until the reaction became homogeneous. The resulting solution was maintained at 95° C. boiling off the MeOH until the reaction solution just starts to become cloudy, upon which heating is turned off, and the reaction is allowed to slowly cool to 25° C. overnight. The precipitate is filtrated and washed with cold iPrOH. The solid is dissolved in EtOAc and washed with 1N HCl, brine, dried (Na₂SO₄) and concentrated to afford Compound (j) as a colorless solid (1.78 g, 6.24 mmol, 80%, 99% ee). $^1$HNMR (400 MHz,CDCl₃) δ=10.24 (br. s., 1H), 7.44-7.28 (m, 5H), 5.26-5.12 (m, 2H), 4.70-4.54 (m, 1H), 3.89-3.77 (m, 1H), 3.76-3.61 (m, 1H), 2.65-2.35 (m, 2H); $[α]_D^{26}$=−18.9 (c 0.97, CHCl₃). Enantiomeric excess was determined by chiral HPLC by integration of spectra recorded at 210 nm on an Agilent 1100 series HPLC on a Chiralcel® OD column (particle size: 10 μm, internal diameter: 4.6 mm, length: 250 mm) and using the following parameters: Flow rate: 1 mL/min, column temperature: 22° C., solvent system: hexanes/iPrOH (0.01% TFA): 60/40 over 10 min. (R)-enantiomer retention time=4.04 min; (S)-enantiomer retention time=6.38 min.

Scheme 3

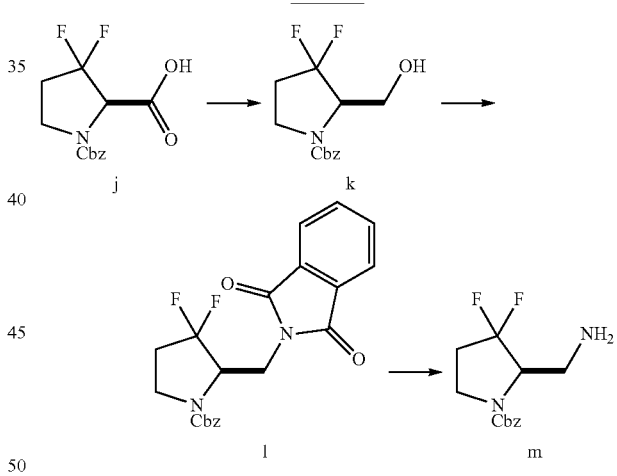

Compound (k): (R)-benzyl 3,3-difluoro-2-(hydroxymethyl)pyrrolidine-1-carboxylate. To a solution of (R)-1-((benzyloxy)carbonyl)-3,3-difluoropyrrolidine-2-carboxylic acid (8.4 g, 29.5 mmol) (Compound (j)) in THF (120 mL) at 0° C. was added a solution of BH₃.THF (1.0M in THF, 1.5 eq) dropwise. Once the addition was complete, the reaction was allowed to warm to 25° C. overnight. The reaction was monitored by reverse-phase analytical HPLC for disappearance of starting acid. If necessary, additional BH₃.THF was added until starting material was consumed. The reaction was quenched by the addition of MeOH, and then concentrated in vacuo. The crude residue was dissolved in EtOAc and washed with 1M HCl (2×), brine (2×), dried (MgSO₄) and concentrated in vacuo, to afford the title compound (7.4 g, 93%) as a colorless oil which was used without further purification. $^1$H NMR (400 MHz, CDCl₃) δ=7.3-7.5 (br. s., 5H), 5.0-5.3 (m, 2H), 4.0-4.2 (m, 1H), 3.70-3.8 (m, 1H), 3.6-3.8 (m, 2H), 2.2-2.5 (m, 2H).

Compound (l): (R)-benzyl 2-((1,3-dioxoisoindolin-2-yl)methyl)-3,3-difluoropyrrolidine-1-carboxylate. To a solution of (R)-benzyl 3,3-difluoro-2-(hydroxymethyl)pyrrolidine-1-carboxylate (Compound (k)) (7.4 g, 27.3 mmol) in toluene (150 mL) was added ADDP (2 eq) followed by PBu$_3$ (3 eq). The reaction turned from dark orange to light yellow and was stirred for 30 min at 25° C. Phthalimide (1.5 eq) was added, and the reaction mixture was warmed to 80° C. overnight. After 12 h, starting material was consumed as judged by HPLC. The reaction was cooled to 25° C., filtered, washing with hexanes, and then concentrated in vacuo. The crude mixture was dissolved in toluene and washed with 1M NaOH (2×), 1M HCl (2×), brine (1×), dried (MgSO$_4$), and concentrated. Purification on SiO$_2$ (EtOAc/hexanes) afforded the title compound as a colorless oil. LC-MS (M+H)$^+$ 401.1.

Compound (m): (R)-Benzyl 2-(aminomethyl)-3,3-difluoropyrrolidine-1-carboxylate. To the solution of benzyl (R)-2-((1,3-dioxoisoindolin-2-yl)methyl)-3,3-difluoropyrrolidine-1-carboxylate (Compound (l)) (200 mg, 0.5 mmol) in MeOH (10 mL) was added hydrazine (85%, 147 mg, 2.5 mmol). After heating for 1.5 h at 80° C., the starting material was consumed and the reaction was cooled to room temperature. After removal of solvent under reduced pressure, the residue was dissolved in ethyl acetate (10 mL); the mixture was washed with saturated NaHCO$_3$ (10 mL) and brine (10 mL), dried over Na$_2$SO$_4$. The solvent was removed under reduced pressure, and then the crude product was used for next step without further purification. $^1$H NMR (300 MHz, CDCl$_3$): δ=1.86-2.06 (m, 2H), 2.36-2.40 (m, 2H), 3.00-3.05 (m, 2H), 3.33-3.34 (m, 2H), 3.61-3.65 (m, 1H), 5.16 (s, 2H), 7.38 (m, 5H); ESI(+ve) MS (M+H)$^+$ 271.3, mass=270.1.

Compound (n): (R)-benzyl 3,3-difluoro-2-((5-(trifluoromethyl)pyrazin-2-ylamino)methyl)pyrrolidine-1-carboxylate.

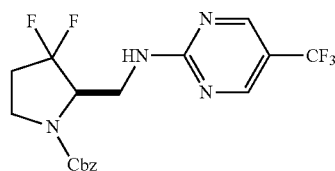

The compound was prepared by General Method A using Compound (m) (68 mg, 0.25 mmol) and 2-chloro-5-(trifluoromethyl)pyrimidine (68 mg, 0.38 mmol). The crude was purified by column chromatography (silica gel, petroleum ether/ethyl acetate: 5/1) to give the product Compound (n) (45 mg, 0.11 mmol, 44%) as a yellow oil. $^1$H NMR (400 MHz, CDCl$_3$): δ=2.33-2.48 (m, 2H), 3.51-3.70 (m, 2H), 3.77-3.97 (m, 2H), 4.19-4.33 (m, 1H), 5.20 (s, 2H), 5.80-6.60 (m, 1H), 7.39 (m, 5H), 8.46 (m, 2H); ESI(+ve) MS (M+H)$^+$ 417.3, mass=416.1.

Compound (o): (R)-Benzyl 2-((5-chloropyrimidin-2-ylamino)methyl)-3,3-difluoropyrrolidine-1-carboxylate.

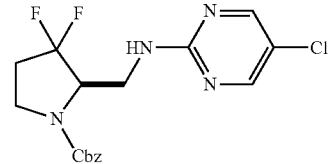

The compound was prepared by General Method A using Compound (m) (140 mg, 0.52 mmol) and 2,5-dichloropyrimidine (114 mg, 0.78 mmol). The crude was purified by column chromatography (silica gel, petroleum ether/ethyl acetate: 10/1) to give the product Compound (o) (50 mg, 0.13 mmol, 25% yield over two steps) as a yellow oil. $^1$H NMR (300 MHz, CDCl$_3$): δ=1.76-1.86 (m, 2H), 2.38-2.48 (m, 2H), 3.47-3.64 (m, 2H), 3.85-3.92 (m, 1H), 4.20-4.30 (m, 1H), 5.21 (s, 2H), 7.38 (m, 5H), 8.08-8.18 (m, 2H); ESI(+ve) MS (M+H)$^+$ 383.3, mass=382.1.

Compound (p): (R)-benzyl 3,3-difluoro-2-((5-(trifluoromethyl)pyrazin-2-ylamino)methyl)pyrrolidine-1-carboxylate.

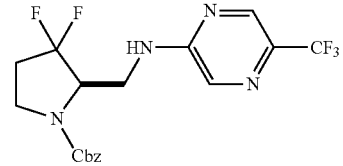

The compound was prepared by General Method A using Compound (m) (250 mg, 0.93 mmol) and 2-chloro-5-(trifluoromethyl)pyrazine (253 mg, 1.39 mmol). The crude was purified by column chromatography (silica gel, petroleum ether/ethyl acetate: 10/1) to give the product Compound (p) (60 mg, 0.14 mmol, 16%) as a yellow oil. $^1$H NMR (400 MHz, CDCl$_3$): δ=2.38-2.44 (m, 2H), 3.55-3.58 (m, 2H), 3.62-3.90 (m, 2H), 4.28-4.31 (m, 1H), 5.17 (s, 2H), 7.37 (m, 5H), 7.94-8.01 (m, 1H), 8.29-8.34 (m, 1H); ESI(+ve) MS (M+H)$^+$ 417.4, mass=416.1.

Compound (q):_(R)-N-((3,3-Difluoropyrrolidin-2-yl)methyl)-5-(trifluoromethyl)pyrazin-2-amine.

The compound was prepared by General Method B using Compound (n) (50 mg, 0.13 mmol). Product Compound (q) (29 mg, 0.10 mmol, 95%) was isolated as a yellow oil. ESI(+ve) MS (M+H)$^+$ 283.3, mass=282.1.

Compound (r): (R)-5-Chloro-N-((3,3-difluoropyrrolidin-2-yl)methyl)pyrimidin-2-amine.

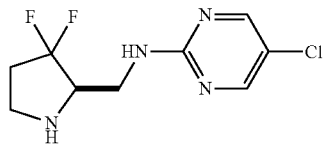 [SMILES: FC1(F)CCN[C@@H]1CNc1ncc(Cl)cn1]

The compound was prepared by General Method B using compound Compound (o) (50 mg, 0.13 mmol). Product Compound (r) (25 mg, 0.10 mmol, 77%) was isolated as a yellow oil. $^1$H NMR (300 MHz, CDCl$_3$): δ=2.19-2.37 (m, 2H), 3.06-3.22 (m, 2H), 3.41-3.61 (m, 2H), 3.68-3.75 (m, 1H), 5.56 (s, 1H), 8.24 (s, 2H); ESI(+ve) MS (M+H)$^+$ 249.6, mass=248.1.

Compound (s): (R)-N-((3,3-Difluoropyrrolidin-2-yl)methyl)-5-(trifluoromethyl)pyrazin-2-amine.

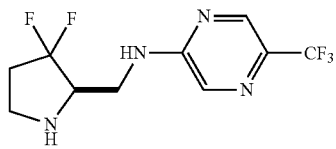 [SMILES: FC(F)(F)c1cnc(NC[C@H]2NCCC2(F)F)cn1]

The compound was prepared by General Method B using compound Compound (p) (60 mg, 0.14 mmol). Product Compound (s) (25 mg, 0.09 mmol, 63%) was isolated as a yellow oil. $^1$H NMR (400 MHz, CDCl$_3$): δ=2.17-2.28 (m, 2H), 2.68 (m, 2H), 3.05-3.15 (m, 2H), 3.45-3.50 (m, 1H), 3.63-3.68 (m, 1H), 5.58 (s, 1H), 7.87 (s, 1H), 8.26 (s, 1H); ESI(+ve) MS (M+H)$^+$ 283.3, mass=282.1.

Compound (t): 5-Fluoro-2-(2H-1,2,3-triazol-2-yl)benzoic acid

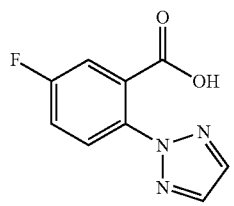

A mixture of 2-bromo-5-methylbenzoic acid (1 eq.), 1,2,3-triazole (2 eq.), (1S,2S)-N1,N2-dimethylcyclohexane-1,2-diamine (1.5 eq.), Cs$_2$CO$_3$ (1.5 eq.), and CuI (0.07 eq.) in DMF (0.775 M) was degassed and heated at 120° C. for 1 h in a microwave reactor. The reaction was cooled to RT, diluted with MeOH, and acidified with AcOH to pH 4-5. The solvent was removed in vacuo to obtain the crude which was purified by silica gel chromatography (0~100% DCM/EtOAc) to yield the title compound as a yellow oil. MS (ESI) 208 (M+H).

Compound (u): 3,4-Difluoro-2-(2H-1,2,3-triazol-2-yl)benzoic acid

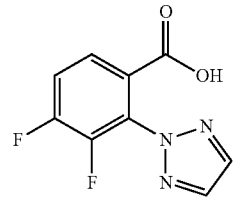

The title compound was prepared from 2,3-difluoroaniline as described for Compound (t). MS (ESI) 226 (M+H).

Compound (v): 5-Fluoro-2-iodo-3-methylbenzoic acid

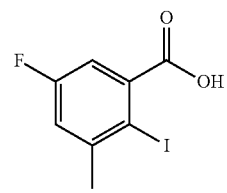

Step 1. 5-Fluoro-3-methyl-2-nitrobenzoic acid. 3-Fluoro-5-methylbenzoic acid (4 g, 25.96 mmol) and KNO$_3$ (2.884 g, 28.556 mmol) were dissolved in conc. H$_2$SO$_4$ (32 mL) at 0° C. The mixture was stirred at rt for 1 h. Water (60 mL) was added, and the resulting precipitate was filtered and dried to provide the title compound, which was used without further purification.

Step 2. 2-Amino-5-fluoro-3-methylbenzoic acid. A mixture of 5-fluoro-3-methyl-2-nitrobenzoic acid (4.86 g, 24.42 mmol) and SnCl$_2$ (16.5 g, 72.36 mmol) in EtOAc was heated at 70° C. overnight. After cooling at rt, the pH was adjusted to 7-8 with satd. aq. NaHCO$_3$. The mixture was extracted with EtOAc, and the organic layer was washed with brine, filtered through diatomaceous earth, and dried over Na$_2$SO$_4$ to provide the title compound, which was used without further purification. ESI-MS (m/z): 170 [M+1]$^+$.

Step 3. A 0° C. solution of 2-amino-5-fluoro-3-methylbenzoic acid (1.5 g, 6.118 mmol) in conc. H$_2$SO$_4$ (4 mL) and water (10 mL) was stirred for 10 min, and then a solution of NaNO$_2$ (0.55 g, 7.95 mmol) in water (1 mL) was added slowly. After 1 h, a solution of KI (5.1 g, 30.6 mmol) in water (6 mL) was added. After 16 h at rt, the reaction mixture was extracted with EtOAc, and the combined organic layers were washed with satd. aq. Na$_2$S$_2$O$_3$ (aq) and brine, dried over MgSO$_4$, and concentrated to provide the title compound. ESI-MS (m/z): 281 [M+1]$^+$.

Compound (w): 3,5-Difluoro-2-(2H-1,2,3-triazol-2-yl)benzoic acid

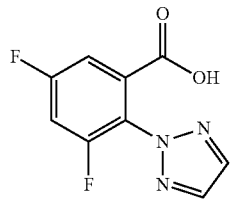 [SMILES: O=C(O)c1cc(F)cc(F)c1-n1nccn1]

Step 1. 3,5-Difluoro-2-iodobenzoic acid. The title compound was prepared from 3,5-difluorobenzoic acid as described for Compound (v). ESI-MS (m/z): 285 [M+1]$^+$.

Step 2. The title compound was prepared from 3,5-difluoro-2-iodobenzoic acid and 1,2,3-triazole as described for Compound (t). ESI-MS (m/z): 226 [M+1]$^+$.

Compound (x): 3,6-Difluoro-2-(2H-1,2,3-triazol-2-yl)benzoic acid

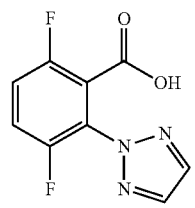

Step 1. 3,6-Difluoro-2-iodobenzoic acid. To freshly distilled diisopropylamine (14 mL, 0.1 mol) in THF (200 mL) at 0° C. was slowly added BuLi (40 mL, 2.5 M, 0.1 mol) under argon. After 30 min at rt, the mixture was cooled to −78° C. and treated with 1,4-difluoro-2-iodobenzene (24 g, 0.1 mol). After 1 h at −78° C., the reaction was quenched with solid $CO_2$. The reaction was allowed to warm to rt and was concentrated. The resulting residue was partitioned between 4 N NaOH (aq) and diethyl ether. The aqueous phase was adjusted to pH 2 with 2 N HCl and extracted with EtOAc (3×). The combined extracts were washed with water and brine, dried ($MgSO_4$), filtered, and concentrated to provide the title compound.

Step 2. The title compound was prepared from 3,6-difluoro-2-iodobenzoic acid using the methods described herein. MS (ESI) 226 (M+H).

Compound (y): 2,3-Difluoro-6-(pyrimidin-2-yl)benzoic acid

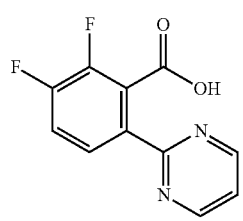 [SMILES: O=C(O)c1c(-c2ncccn2)ccc(F)c1F]

Step 1. Methyl 6-bromo-2,3-difluorobenzoate. A stirred solution of 6-bromo-2,3-difluorobenzoic acid and concentrated $H_2SO_4$ in MeOH was heated at reflux for 18 h. After this time, the reaction mixture was cooled to rt and concentrated under reduced pressure. The residue was diluted carefully added satd. aq. $NaHCO_3$ and extracted with $CH_2Cl_2$. The combined extracts were dried over anhydrous $Na_2SO_4$, filtered, and concentrated under reduced pressure. The residue was dried under high vacuum to afford the title compound. ESI MS (M+H) 251.

Step 2. Methyl 2,3-difluoro-6-(4,4,5,5-tetramethyl-1,3,2-dioxaborolan-2-yl)benzoate. A stirred suspension of methyl 6-bromo-2,3-difluorobenzoate, 4,4,4',4',5,5,5',5'-octamethyl-2,2'-bis(1,3,2-dioxaborolane), $PdCl_2(dppf)$, and KOAc in anhydrous 1,4-dioxane was heated at 100° C. under nitrogen for 20 h. After this time, the reaction mixture was cooled to rt and concentrated under reduced pressure. The resulting residue was directly purified by flash column chromatography on silica gel eluting with 0% to 15% EtOAc/hexanes to give the title compound. ESI MS (M+H) 299.

Step 3. Methyl 2,3-difluoro-6-(pyrimidin-2-yl)benzoate. A stirred suspension of methyl 2,3-difluoro-6-(4,4,5,5-tetramethyl-1,3,2-dioxaborolan-2-yl)benzoate, 2-chloropyrimidine, $PdCl_2(dppf)$, and $K_2CO_3$ in 1,4-dioxane and water (3:1, v/v) was heated at 90° C. under nitrogen for 18 h. The reaction mixture was cooled to rt and concentrated under reduced pressure. The resulting residue was directly purified by flash column chromatography on silica gel eluting with 0% to 50% EtOAc/hexanes to give the title compound. ESI MS (M+H) 251.

Step 4. A solution of methyl 2,3-difluoro-6-(pyrimidin-2-yl)benzoate in 2 N NaOH and water was heated at reflux for 4 h. The reaction mixture was cooled to rt and concentrated to half volume under reduced pressure. The resulting mixture was acidified to pH 4 with 1 N HCl and extracted with EtOAc. The combined extracts were dried over anhydrous $Na_2SO_4$, filtered, and concentrated under reduced pressure. The residue was dried under high vacuum to give the title compound. ESI MS (M+H) 237.

Compound (z): 4-Methyl-2-(pyrimidin-2-yl)benzoic acid

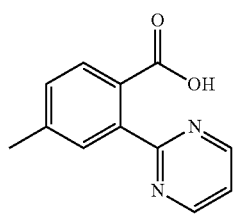 [SMILES: Cc1ccc(C(=O)O)c(-c2ncccn2)c1]

The title compound was prepared following the same general protocol as described for Compound (y) using 2-bromo-4-methylbenzoic acid. ESI MS (M+H) 215.

Compound (aa): 6-Fluoro-3-methyl-2-(2H-1,2,3-triazol-2-yl)benzoic acid

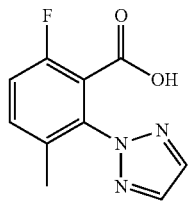 [SMILES: Cc1ccc(F)c(C(=O)O)c1-n1nccn1]

Step 1. (Z)-N-(5-Fluoro-2-methylphenyl)-2-(hydroxyimino)acetamide. A −10° C. mixture of 5-fluoro-2-methylaniline (10 g, 80 mmol) and NaHCO$_3$ (67 g, 800 mmol) in CH$_2$Cl$_2$ (200 mL) was treated dropwise with a solution of freshly distilled 2,2-diacetoxyacetyl chloride (20 g, 103 mmol). The mixture was allowed to warm to rt. When TLC indicated consumption of the aniline, the solid was removed by filtration, washed with CH$_2$Cl$_2$, and the filtrate was concentrated. Hydroxylamine hydrochloride (28 g, 400 mmol) was dissolved in a mixture of ethanol (200 mL) and water (100 mL), and the solution was then added to the crude diacetates. The mixture was heated at reflux for 2 h, cooled to rt, and concentrated until precipitation commenced. Water was then added to precipitate additional product. The solid was collected by filtration and washed with water to yield the title compound (7.22 g, 46%). $^1$H NMR (CDCl$_3$, 400 MHz) δ 8.25 (bs, 1H), 7.99 (bs, 1H), 7.85 (m, 1H), 7.55 (s, 1H), 7.05 (m, 1H), 6.7 (m, 1H), 2.20 (s, 3H).

Step 2. 4-Fluoro-7-methylindoline-2,3-dione. A solution of (Z)-N-(5-Fluoro-2-methylphenyl)-2-(hydroxyimino)acetamide (7.22, 37 mmol) and conc. H$_2$SO$_4$ (50 mL) was heated at 60° C. for 1 h. The resulting solid was collected by filtration and washed with water to yield the title compound. $^1$H NMR (CDCl$_3$, 400 MHz) δ 8.35 (bs, 1H), 7.45 (m, 1H), 6.73 (m, 1H), 2.25 (s, 3H).

Step 3. 2-Amino-6-fluoro-3-methylbenzoic acid. A solution of 4-fluoro-7-methylindoline-2,3-dione (6.20 g, 34.6 mmol) in 1 M NaOH (114 mL) was treated dropwise with 30% aq. H$_2$O$_2$ (20 mL) and the resulting mixture was heated at 50° C. for 30 min, cooled to rt, and filtered. The filtrate was adjusted to pH 4 with conc. HCl, cooled to 4° C. and filtered. The filter cake was dried under vacuum to provide the desired product. $^1$H NMR (CDCl$_3$, 400 MHz) δ 7.15 (m, 1H), 6.40 (m, 1H), 2.15 (s, 3H).

Step 4. 6-Fluoro-2-iodo-3-methylbenzoic acid. A solution of 2-amino-6-fluoro-3-methylbenzoic acid in 7.5 mL of H$_2$SO$_4$ and 15 mL of H$_2$O was stirred for 30 min. The resultant suspension was cooled to 0° C., and treated dropwise with a solution of NaNO$_2$ (1.06 g, 11.8 mmol) in 2 mL of H$_2$O. After 1.5 h at 0° C., the mixture was treated slowly with a solution of KI (9.8 g, 59 mmol) in 10 mL of H$_2$O. The resulting mixture was stirred vigorously at rt overnight, diluted with water and extracted with EtOAc. The combined extracts were washed with brine, aq. Na$_2$S$_2$O$_3$, and water, dried over Na$_2$SO$_4$, and concentrated. The residue was subjected to silica-gel chromatography (0 to 20% EtOAc/hexanes). $^1$H NMR (CDCl$_3$, 400 MHz) δ 7.25 (m, 1H), 7.05 (m, 1H), 2.48 (s, 3H).

Step 5. A mixture of 6-fluoro-2-iodo-3-methylbenzoic acid (900 mg, 3.21 mmol), 1,2,3-triazole (208 μL, 4.82 mmol), (1S,2S)-N1,N2-dimethylcyclohexane-1,2-diamine (103 μl, 642 μmol), Cs$_2$CO$_3$ (1.57 g, 4.82 mmol), and CuI (61 mg, 321 μmol) in DMF (5 mL) was degassed and heated at 120° C. for 1 h in a microwave reactor. The reaction was cooled to rt, diluted with MeOH, acidified with AcOH to pH4-5, and concentrated. The residue was purified by silica gel chromatography (40% EtOAc in hexanes) to yield the title compound. MS (ESI) 222 (M+H).

Compounds (ab-ag): were prepared as described for Compound (aa).

Compound (ab): 4-Fluoro-3-methyl-2-(2H-1,2,3-triazol-2-yl)benzoic acid

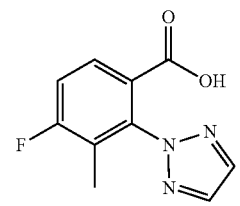 [SMILES: Cc1c(F)ccc(C(=O)O)c1-n1nccn1]

Step 1. 4-Fluoro-2-iodo-3-methylbenzoic acid. MS (ESI) 281 (M+H).
Step 2. MS (ESI) 222 (M+H).

Compound (ac): 5-Fluoro-4-methyl-2-(2H-1,2,3-triazol-2-yl)benzoic acid

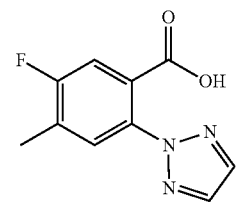 [SMILES: Cc1cc(-n2nccn2)c(C(=O)O)cc1F]

Step 1. 5-Fluoro-2-iodo-4-methylbenzoic acid. MS (ESI) 281 (M+H).
Step 2. MS (ESI) 222 (M+H).

Compound (ad): 4-Fluoro-5-methyl-2-(2H-1,2,3-triazol-2-yl)benzoic acid

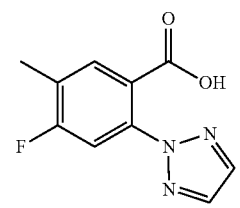 [SMILES: Cc1cc(C(=O)O)c(-n2nccn2)cc1F]

Step 1. 4-Fluoro-2-iodo-5-methylbenzoic acid. MS (ESI) 281 (M+H).
Step 2. MS (ESI) 222 (M+H).

Compound (ae): 3-Fluoro-5-methyl-2-(2H-1,2,3-triazol-2-yl)benzoic acid

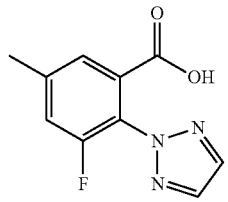 [SMILES: Cc1cc(F)c(-n2nccn2)c(C(=O)O)c1]

Step 1. 3-Fluoro-2-iodo-5-methylbenzoic acid. MS (ESI) 281 (M+H).
Step 2. MS (ESI) 222 (M+H).

Compound (af): 3-Fluoro-4-methyl-2-(2H-1,2,3-triazol-2-yl)benzoic acid

Step 1. 3-Fluoro-2-iodo-4-methylbenzoic acid. MS (ESI) 281 (M+H).
Step 2. MS (ESI) 222 (M+H).

Compound (ag): 3-Fluoro-2-methyl-6-(2H-1,2,3-triazol-2-yl)benzoic acid

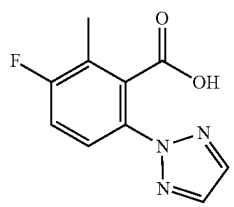

Step 1. 3-Fluoro-6-iodo-2-methylbenzoic acid. MS (ESI) 281 (M+H).
Step 2. MS (ESI) 222 (M+H).

Compound (ah): 2-Chloro-5-fluorobenzo[d]oxazole

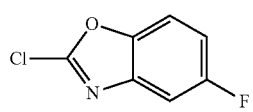

Step 1. 5-Fluorobenzo[d]oxazole-2-thiol. A mixture of 2-amino-4-fluorophenol (1 g, 7.9 mmol) and ethylxanthic acid potassium salt (1.3 g, 7.9 mmol) in EtOH (10 mL) was heated at reflux for 7 h. The mixture was cooled to rt and concentrated in vacuo. The crude was dissolved in water and adjusted to pH 5 with acetic acid. The product was filtered to obtain the title compound, which was used without further purification.
Step 2. A mixture of 5-fluorobenzo[d]oxazole-2-thiol (300 mg, 1.7 mmol) in thionyl chloride (6 mL) and 2 drops of DMF were heated at 70° C. for 3 h. The mixture was cooled to rt and concentrated in vacuo. The crude was dissolved in EtOAc and filtered through silica gel. The filtrate was concentrated to obtain the title compound, which was used without further purification. $^1$H NMR (CDCl$_3$, 400 MHz) δ 7.44 (dd, J=4.3, 8.6 Hz, 1H), 7.37 (dd, J=2.8, 8.08 Hz, 1H), 7.09 (dt, J=2.5, 9.09 Hz, 1H).

Compound (ai): 2-Chloro-5-(trifluoromethyl)benzo[d]oxazole

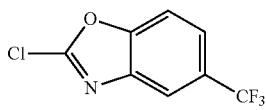

The title compound was prepared following the same general protocol as described for (Compound (ah)), using 2-amino-4-trifluoromethylphenol. ESI-MS (m/z): 222 [M+1]$^+$.

Compound (aj): 5-Fluoro-3-methyl-2-(2H-1,2,3-triazol-2-yl)benzoic acid

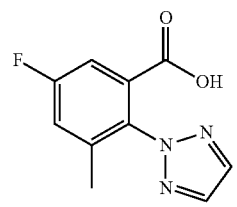 [SMILES: Cc1cc(F)cc(C(=O)O)c1-n1nccn1]

The title compound was prepared from 2-iodo-5-fluoro-3-methylbenzoic acid using methods analogous to those described herein. MS (ESI) 222 (M+H).

Synthesis of Compounds of Formula (I) and (II)
General Procedure 1:

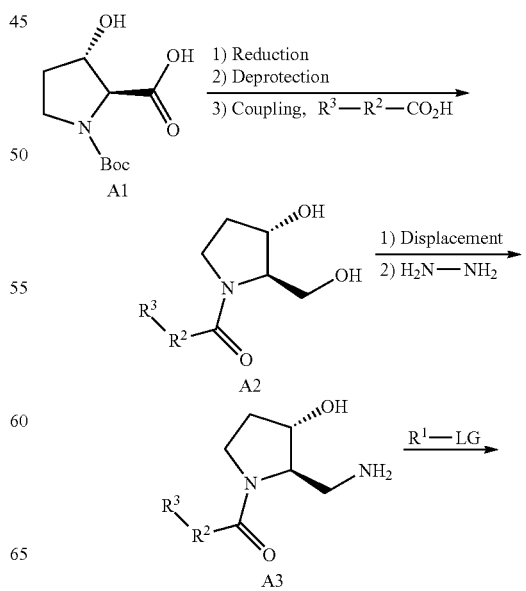

Scheme A

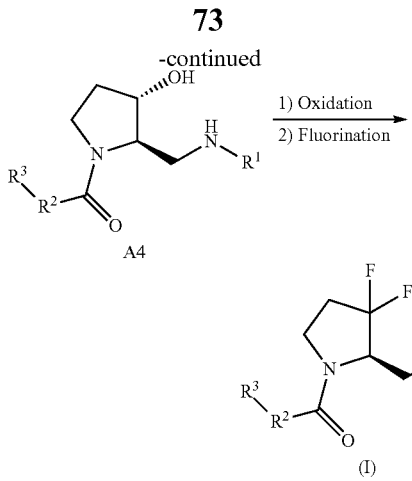

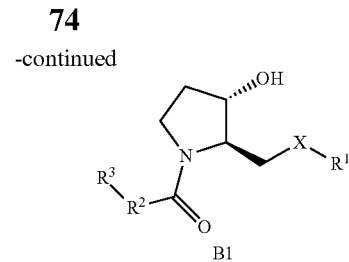

Compounds of Formula (I) may be prepared according to Scheme A. Commercially available acid A1 is globally reduced with a suitable reducing agent such as borane to provide the corresponding diol. The Boc protecting group is removed using standard procedures such as treatment with trifluoroacetic acid. The resulting secondary amine is coupled with a suitable $R^3$-$R^2$-containing reagent, such as a carboxylic acid (under standard amide coupling conditions) or acyl chloride (in the presence of a suitable tertiary amine base), to provide amides A2. For compounds where X is NH, the nitrogen is introduced by activation/displacement of the primary alcohol with a suitable masked amine group. Examples include treatment with phthalimide under Mitsunobu conditions and activation as the tosylate and displacement with an azido anion. Where a phthalimide or azide is introduced, such groups are then reduced or cleaved to the corresponding primary amine group using, for example, hydrazine or triphenylphosphine, to generate amines A3. The A3 amino group is then be reacted with $R^1$-LG, where $R^1$ is a heteroaryl group and LG is a suitably positioned leaving group such as chloro, in the presence of a suitable base such as $K_2CO_3$, to yield amino-alcohols A4. Where $R^1$ is phenyl or a heteroaryl without an activated leaving group, the primary amine is coupled with $R^1$ through metal-mediated procedures (e.g., Buchwald or Ulmann couplings) known to those skilled in the art. Oxidation of the secondary alcohol using a suitable reagent such as Dess-Martin periodinane, potassium dichromate, or Swern oxidation, yields a ketone, which is perfluorinated using a suitable fluorinating agent such as diethylaminosulfur trifluoride (DAST) or bis(2-methoxyethyl)aminosulfur trifluoride, to generate compounds of Formula (I) where X is $NR^4$, wherein $R^4$ is H. The NH may be alkylated using methods known to one of skill in the art to prepare compounds of Formula (I) where X is N $R^4$, and $R^4$ is ($C_{1-4}$alkyl).
General Procedure 2:

Scheme B

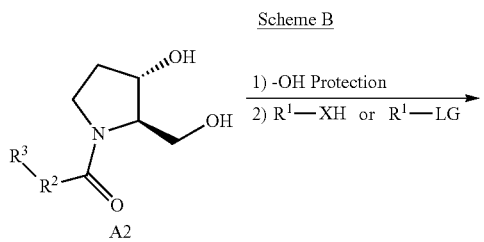

Compounds of Formula (I) may also be prepared according to Scheme B. Following an optional introduction of a protecting group on the secondary alcohol (which may require multiple protection/deprotection steps), the primary alcohol of diols A2 is reacted with a heteroaryl with an activated leaving group ($R^1$-LG) as described above for Scheme A to yield compounds B1 where X is O. Alternatively, the primary alcohol is activated and displaced with $R^1$—$NH_2$ or $R^1$—OH under, for example, Mitsunobu conditions, to give compounds B1 where X is NH or O. Oxidation and fluorination as in Scheme A yields compounds of Formula (I).
General Procedure 3:

Alternatively, compounds of Formula (I) or (II) may be prepared according to Scheme C.
General Method A To a mixture of (R)-Benzyl 2-(aminomethyl)-3,3-difluoropyrrolidine-1-carboxylate ((compound (m)) (0.52 mmol, 1 equiv.) and $K_2CO_3$ (2 eq) in DMF (5 mL) was added the electrophile (1.5 eq,). The mixture was stirred for 2.5 h at 100° C. After cooling to room temperature, the reaction mixture was diluted with water (10 mL) and extracted with ethyl acetate (10 mL×2). The combined organic layers were washed with brine (10 mL) and dried over $Na_2SO_4$. After removal of solvent under reduced pressure, the residue was purified by column chromatography (silica gel, petroleum ether/ethyl acetate: 10/1) to give product (compound (n), (o), (p)).

Scheme C

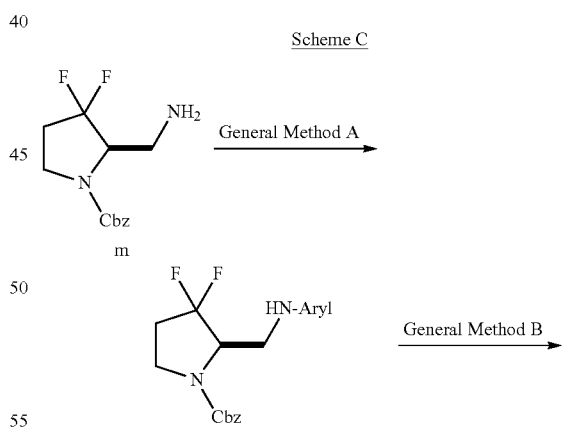

n: Aryl = 5-trifluoromethyl-pyrimidine
o: Aryl = 5-chloropyrimidine
p: Aryl = 5-(trifluoromethyl)-pyrazine

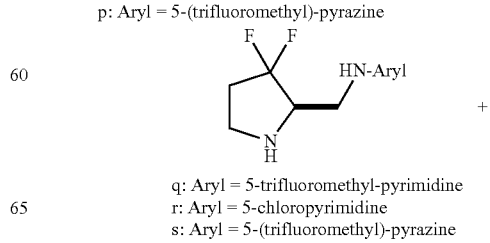

q: Aryl = 5-trifluoromethyl-pyrimidine
r: Aryl = 5-chloropyrimidine
s: Aryl = 5-(trifluoromethyl)-pyrazine -continued

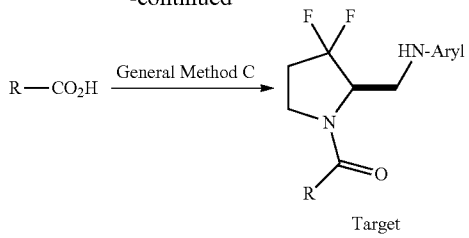

General Method B

A solution of starting material (compound (n), (o), (p)) in 33% HBr in HOAc was stirred at room temperature until the starting material was consumed as judged by reverse-phase analytical HPLC. The reaction mixture was concentrated under reduced pressure, and the residue was dissolved in ethyl acetate (10 mL). The organic solution was washed with saturated NaHCO$_3$ (10 mL) and brine (10 mL), dried over Na$_2$SO$_4$. Removal of solvent under reduced pressure afforded the -Cbz deprotected product (compound (q), (r), (s)), which was used for next step without further purification.

General Method C

To the stirred solution of starting material (0.10 mmol, 1 equiv.) in DMF (8 mL) were added the acid (0.11 mmol, 1.1 equiv.), HATU (0.12 mmol, 1.2 equiv.) and DIPEA (0.40 mmol, 4 equiv.) at 0° C. After stirring for 30 min at room temperature, the reaction mixture was diluted with water (10 mL) and then extracted with ethyl acetate (10 mL×2). The combined organic layers were washed with brine (10 mL) and dried over Na$_2$SO$_4$. After removal of solvent under reduced pressure, the residue was purified by either column chromatography (silica gel, petroleum ether/ethyl acetate: 5/1) or prep-HPLC to afford the target.

Compound 1: (R)-(3,3-Difluoro-2-(((5-(trifluoromethyl)pyrimidin-2-yl)amino)methyl)pyrrolidin-1-yl) (5-(4-fluorophenyl)-2-methylthiazol-4-yl)methanone

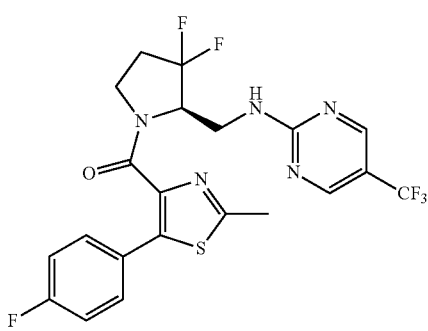 [SMILES: Cc1nc(C(=O)N2CCC(F)(F)[C@H]2CNc2ncc(C(F)(F)F)cn2)c(-c2ccc(F)cc2)s1]

Step 1: (2S,3S)-1-(tert-Butoxycarbonyl)-3-hydroxypyrrolidine-2-carboxylic acid. To a solution of (2S,3S)-3-hydroxypyrrolidine-2-carboxylic acid (3.0 g, 23 mmol) in dioxane/H$_2$O (40 mL/20 mL) was added sodium hydroxide (1.83 g, 46 mmol), followed by the dropwise addition of di-tert-butyl dicarbonate (9.49 g, 43 mmol) in dioxane (15 mL). The reaction mixture was stirred at room temperature (rt) for 2 h. The reaction mixture was extracted with EtOAc (50 mL) and the organic layer was washed with 10% aq. NaOH (30 mL). The combined aqueous layers were acidified with conc. HCl to pH 2 and extracted with CH$_2$Cl$_2$. The organic phases were dried (Na$_2$SO$_4$) and concentrated to give the crude product, which was used without further purification (5.01 g, 95%). $^1$H NMR (CD$_3$OD, 400 MHz) δ 4.40-4.30 (m, 1H), 4.15-4.00 (m, 1H), 3.50-3.40 (m, 2H), 2.00-1.95 (m, 1H), 1.85 (m, 1H), 1.45-1.35 (m, 9H).

Step 2. tert-Butyl (2R,3S)-3-hydroxy-2-(hydroxymethyl) pyrrolidine-1-carboxylate. To a 0° C. solution of (2S,3S)-1-(tert-butoxycarbonyl)-3-hydroxypyrrolidine-2-carboxylic acid (1.00 g, 4.32 mmol) in THF (8 mL) was added borane-dimethyl sulfide (10 M, 2.16 mL, 21 mmol) and the resulting mixture was allowed to warm to RT and stir overnight. The reaction was quenched with MeOH until bubbling subsided. The mixture was concentrated, and the residue was dissolved in EtOAc and washed with satd. aq. NaHCO$_3$, brine, and dried (MgSO$_4$). The solvent was removed and the crude material was used without further purification. ESI-MS (m/z): 218 (M+H).

Step 3. (5-(4-Fluorophenyl)-2-methylthiazol-4-yl)((2R,3S)-3-hydroxy-2-(hydroxymethyl)pyrrolidin-1-yl)methanone. A solution of tert-butyl (2R,3S)-3-hydroxy-2-(hydroxymethyl)pyrrolidine-1-carboxylate (750 mg, 3.45 mmol) in CH$_2$Cl$_2$/trifluoroacetic acid (1:1, 6 mL) and stirred for 30 min. The mixture was concentrated in vacuo and remaining trifluoroacetic acid was removed by azeotrope with 5 M methanolic HCl (20 mL×3), followed by toluene (20 mL) to yield (2R,3S)-2-(hydroxymethyl)pyrrolidin-3-ol HCl salt as a white solid (519 mg, 95%). To a suspension of this intermediate in CH$_2$Cl$_2$ (20 mL) was added 5-(4-fluorophenyl)-2-methylthiazole-4-carboxylic acid (prepared as described in WO2010/038200; 891 mg, 3.76 mmol), diisopropylethyl amine (1.78 mL, 10 mmol) and 1-[bis(dimethylamino)methylene]-1H-1,2,3-triazolo[4,5-b]pyridinium 3-oxide hexafluorophosphate (1.56 g, 4.10 mmol) and the resulting mixture was stirred at rt overnight. The reaction mixture was diluted with CH$_2$Cl$_2$, washed with satd. aq. NaHCO$_3$ and brine, dried (MgSO$_4$), and concentrated in vacuo. The crude product was purified by chromatography on silica gel (EtOAc/hexanes) to afford the title compound (629 mg, 55%). ESI-MS (m/z): 337(M+H).

Step 4. 2-(((2R,3S)-1-(5-(4-Fluorophenyl)-2-methylthiazole-4-carbonyl)-3-hydroxypyrrolidin-2-yl)methyl)isoindoline-1,3-dione. To a 0° C. solution of triphenylphosphine (1.08 g, 4.11 mmol) in THF (10 mL) was added diisopropyl azodicarboxylate (810 µL, 4.11 mmol). After stirring for 20 min, the mixture was treated with a solution of 5-(4-fluorophenyl)-2-methylthiazol-4-yl)((2R,3S)-3-hydroxy-2-(hydroxymethyl)pyrrolidin-1-yl)methanone (629 mg, 1.87 mmol) in THF (5 mL). After a further 30 min at 0° C., the mixture was treated with phthalimide (330 mg, 2.24 mmol) and was warmed to rt and stirred overnight. The resulting suspension was concentrated in vacuo, diluted with EtOAc, washed with water and brine, dried (MgSO$_4$), and concentrated. The crude residue was purified by chromatography on silica gel (EtOAc/hexanes) to give the title compound (250 mg, 29%). ESI-MS (m/z): 466 (M+H).

Step 5. ((2R,3S)-2-(Aminomethyl)-3-hydroxypyrrolidin-1-yl)(5-(4-fluorophenyl)-2-methylthiazol-4-yl)methanone. A mixture of 2-(((2R,3S)-1-(5-(4-fluorophenyl)-2-methylthiazole-4-carbonyl)-3-hydroxypyrrolidin-2-yl)methyl)isoindoline-1,3-dione (200 mg, 430 µmol) and hydrazine hydrate (105 µL, 2.15 mmol) in methanole (10 mL) was heated at 60° C. for 2 h. The mixture was cooled to rt and concentrated. The residue was dissolved in EtOAc and washed with 2 N NaOH (2×) and brine, dried (Na$_2$SO$_4$), and concentrated to obtain the title compound, which was used without further purification. ESI-MS (m/z): 336 (M+H).

Step 6. (5-(4-Fluorophenyl)-2-methylthiazol-4-yl)((2R,3S)-3-hydroxy-2-(((5-(trifluoromethyl)pyrimidin-2-yl)amino)methyl)pyrrolidin-1-yl)methanone. A mixture of ((2R,3S)-2-(aminomethyl)-3-hydroxypyrrolidin-1-yl)(5-(4-fluorophenyl)-2-methylthiazol-4-yl)methanone (45 mg, 134 µmol), 2-chloro-5-(trifluoromethyl)pyrimidine (29 mg, 161 µmol), and anhydrous K$_2$CO$_3$ (56 mg, 403 µmol) in acetonitrile (3 mL) was heated at 80° C. overnight. The mixture was cooled to rt and concentrated. The residue was dissolved in EtOAc, washed with satd. aq. NaHCO$_3$ and brine, dried (MgSO$_4$), and concentrated. The crude product was purified by chromatography on silica gel (EtOAc/hexanes) to afford the title compound. ESI-MS (m/z): 482 (M+H).

Step 7. (R)-1-(5-(4-Fluorophenyl)-2-methylthiazole-4-carbonyl)-2-(((5-(trifluoromethyl)pyrimidin-2-yl)amino)methyl)pyrrolidin-3-one. A solution of (5-(4-fluorophenyl)-2-methylthiazol-4-yl)((2R,3S)-3-hydroxy-2-(((5-(trifluoromethyl)pyrimidin-2-yl)amino)methyl)pyrrolidin-1-yl)methanone (30 mg, 62 µmol) and Dess-Martin periodinane (40 mg, 93 µmol) in CH$_2$Cl$_2$ (1 mL) was stirred at rt for 4 h. The resulting mixture was diluted with CH$_2$Cl$_2$ and water and the layers were separated. The organic layer was washed with brine, dried (MgSO$_4$), and concentrated in vacuo to give a crude residue, which was purified by chromatography on silica gel (EtOAc/hexanes) to afford the title compound. ESI-MS (m/z): 480 (M+H).

Step 8. To a 0° C. solution of (R)-1-(5-(4-fluorophenyl)-2-methylthiazole-4-carbonyl)-2-(((5-(trifluoromethyl)pyrimidin-2-yl)amino)methyl)pyrrolidin-3-one (20 mg, 42 µmol) in CH$_2$Cl$_2$ (1 mL) was added bis(2-methoxyethyl)aminosulfur trifluoride (15 µL, 83 µmol), and the resulting mixture was stirred at rt for 2 d. The mixture was cooled to 0° C., treated with with 1 mL of satd. aq. NaHCO$_3$, diluted with CH$_2$Cl$_2$, washed with water and brine, dried (MgSO$_4$), and concentrated. The crude residue was purified by chromatography on silica gel (EtOAc/hexanes) to give the title compound (5 mg, 24%). MS (ESI) 502 (M+H).

Compound 2: (R)-(3,3-Difluoro-2-(((5-(trifluoromethyl)pyrimidin-2-yl)amino)methyl)pyrrolidin-1-yl)(5-methyl-2-(2H-1,2,3-triazol-2-yl)phenyl)methanone

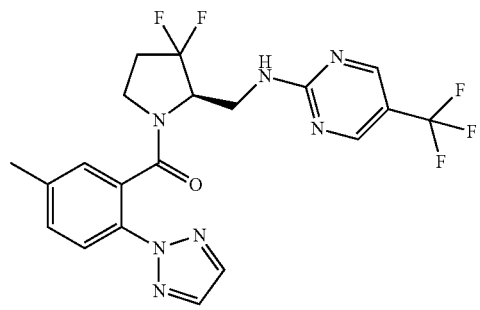 [SMILES: Cc1ccc(-n2nccn2)c(C(=O)N2CCC(F)(F)[C@H]2CNc2ncc(C(F)(F)F)cn2)c1]

$^1$H NMR (500 MHz, DMSO-d$_6$) δ 8.73-7.19 (m, 8H), 4.66-3.28 (m, 5H), 2.44-2.25 (m, 5H); ESI MS (M+H) 468.

Compound 3: (R)-(3,3-Difluoro-2-(((5-(trifluoromethyl)pyrimidin-2-yl)amino)methyl)pyrrolidin-1-yl)(3-fluoro-2-(2H-1,2,3-triazol-2-yl)phenyl)methanone

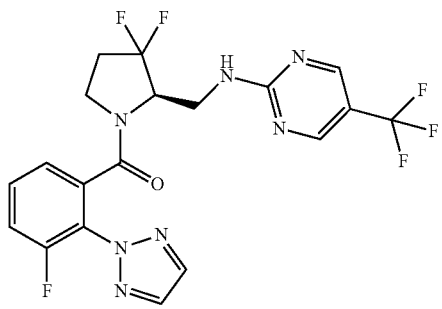 [SMILES: O=C(c1cccc(F)c1-n1nccn1)N1CCC(F)(F)[C@H]1CNc1ncc(C(F)(F)F)cn1]

$^1$H NMR (500 MHz, DMSO-d$_6$) δ 8.70-7.35 (m, 8H), 4.53-3.35 (m, 5H), 2.48-2.35 (m, 2H); ESI MS (M+H) 472.

Compound 5: (R)-(3,3-Difluoro-2-(((5-(trifluoromethyl)pyrimidin-2-yl)amino)methyl)pyrrolidin-1-yl)(5-fluoro-2-(2H-1,2,3-triazol-2-yl)phenyl)methanone

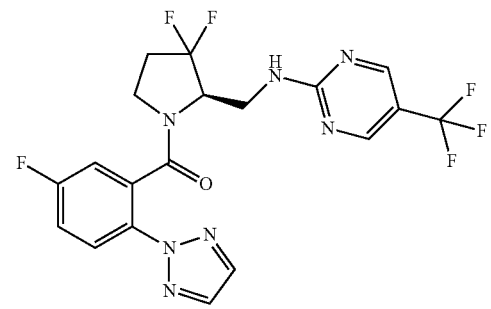 [SMILES: O=C(c1cc(F)ccc1-n1nccn1)N1CCC(F)(F)[C@H]1CNc1ncc(C(F)(F)F)cn1]

$^1$H NMR (500 MHz, DMSO-d$_6$) δ 8.72-7.24 (m, 8H), 4.65-3.28 (m, 5H), 2.55-2.36 (m, 2H); ESI MS (M+H) 472.

Compound 7: (R)-(3,3-difluoro-2-((5-(trifluoromethyl)pyrimidin-2-ylamino)methyl)pyrrolidin-1-yl)(4-fluoro-3-methyl-2-(2H-1,2,3-triazol-2-yl)phenyl)methanone

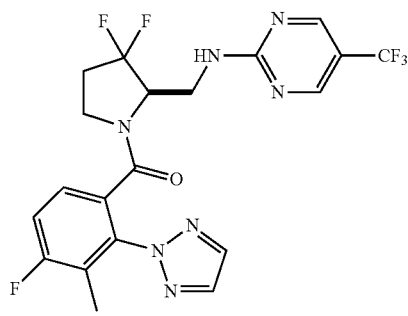 [SMILES: Cc1c(F)ccc(C(=O)N2CCC(F)(F)[C@H]2CNc2ncc(C(F)(F)F)cn2)c1-n1nccn1]

$^1$H NMR (400 MHz, MeOH-d$_4$) δ 2.04-2.18 (2×d, 3H), 2.31-2.55 (m, 2H), 3.36-3.94 (m, 4H), 4.40-4.54 (m, 1H), 7.07-7.43 (m, 2H), 7.91-8.00 (2×s, 2H), 8.32-8.64 (m, 2H); ESI(+ve) UPLC-MS (M+H)+ 486.4, mass=485.1.

Compound 8: (R)-(3,3-difluoro-2-((5-(trifluoromethyl)pyrimidin-2-ylamino)methyl)pyrrolidin-1-yl)(3-fluoro-4-methyl-2-(2H-1,2,3-triazol-2-yl)phenyl)methanone

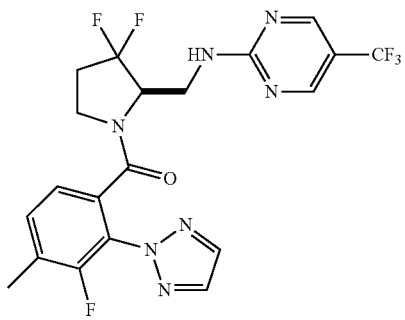 [SMILES: Cc1ccc(C(=O)N2CCC(F)(F)[C@H]2CNc2ncc(C(F)(F)F)cn2)c(-n2nccn2)c1F]

¹H NMR (400 MHz, MeOH-d₄) δ 2.25-2.60 (m, 5H), 3.37-3.94 (m, 4H), 4.46-4.59 (m, 1H), 7.05-7.53 (m, 2H), 7.93-8.03 (2×s, 2H), 8.34-8.66 (m, 2H); ESI(+ve) UPLC-MS (M+H)+ 486.4, mass=485.1.

Compound 10: (R)-(3,3-difluoro-2-(((5-(trifluoromethyl)pyrimidin-2-yl)amino)methyl)pyrrolidin-1-yl)(5-fluoro-2-(pyrimidin-2-yl)phenyl)methanone

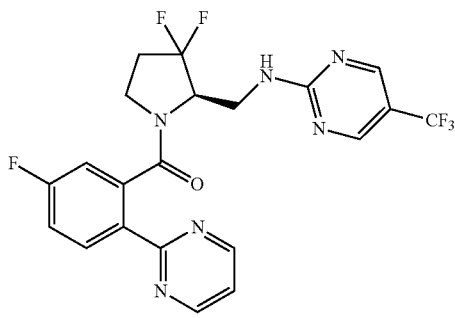 [SMILES: O=C(c1cc(F)ccc1-c1ncccn1)N1CCC(F)(F)[C@H]1CNc1ncc(C(F)(F)F)cn1]

Step 1: (R)-(3,3-difluoro-2-(((5-(trifluoromethyl)pyrimidin-2-yl)amino)methyl)pyrrolidin-1-yl)(5-fluoro-2-iodophenyl)methanone

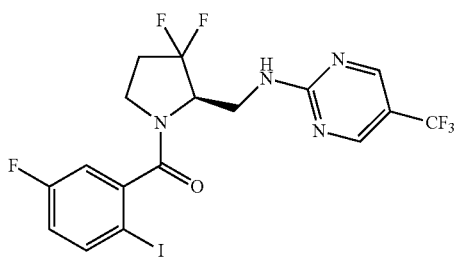 [SMILES: O=C(c1cc(F)ccc1I)N1CCC(F)(F)[C@H]1CNc1ncc(C(F)(F)F)cn1]

The title compound was synthesized following General Procedure C to give the title compound as a colorless solid. LC-MS (M+H)+ 531.1

Step 2: (R)-(3,3-difluoro-2-(((5-(trifluoromethyl)pyrimidin-2-yl)amino)methyl)pyrrolidin-1-yl)(5-fluoro-2-(pyrimidin-2-yl)phenyl)methanone. To a mixture of (R)-(3,3-difluoro-2-(((5-(trifluoromethyl)pyrimidin-2-yl)amino)methyl)pyrrolidin-1-yl)(5-fluoro-2-iodophenyl)methanone (0.077 g, 0.145 mmol), 2-(tributylstannyl)pyrimidine (0.06 mL, 0.174 mmol) and CsF (0.044 g, 0.29 mmol) in DMF (3 mL) was added copper (I) iodide (0.003 g, 0.0145 mmol) and Pd(PPh₃)₄ (0.017 g, 0.0145 mmol). The mixture was degassed and the reaction was heated in a Biotage microwave reactor for 30 min at 120° C. The solvent was removed in vacuo and the crude was dissolved with EtOAc, washed with sat's NaHCO₃, brine, dried (MgSO₄) and concentrated. The crude residue was purified by chromatography on silica gel to obtain the desired product. ¹H NMR (500 MHz, DMSO-d₆) δ 8.90-7.05 (m, 9H), 4.80-3.30 (m, 7H); ESI MS (M+H) 483.

Compound 25: (R)-(3,3-difluoro-2-((5-(trifluoromethyl)pyridin-2-yloxy)methyl)pyrrolidin-1-yl)(5-methyl-2-(2H-1,2,3-triazol-2-yl)phenyl)methanone

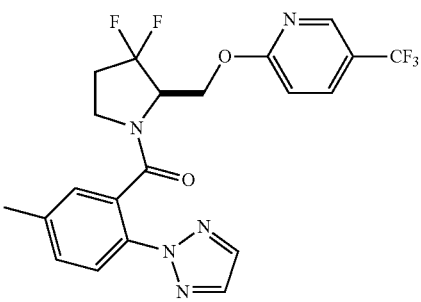 [SMILES: Cc1ccc(-n2nccn2)c(C(=O)N2CCC(F)(F)[C@H]2COc2ccc(C(F)(F)F)cn2)c1]

Step 1: (R)-(3,3-difluoropyrrolidin-2-yl)methanol

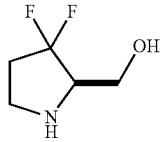

To the solution of (R)-benzyl 3,3-difluoro-2-(hydroxymethyl)pyrrolidine-1-carboxylate (Compound (k)) (200 mg) in EtOAc (3 mL) was added 10% Pd on carbon. The flask was evacuated/H₂ purged (2×), and then stirred under a balloon of H₂ for 16 h. Filtration of the reaction through celite and concentration in vacuo afforded the title compound as a colorless oil which was used without further purification.

Step 2: (R)-(3,3-difluoro-2-(hydroxymethyl)pyrrolidin-1-yl)(5-methyl-2-(2H-1,2,3-triazol-2-yl)phenyl)methanone

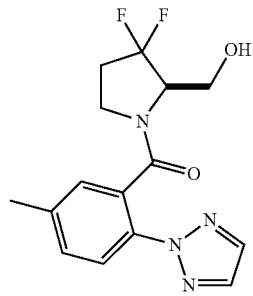 [SMILES: Cc1ccc(-n2nccn2)c(C(=O)N2CCC(F)(F)[C@H]2CO)c1]

The title compound was synthesized following General Procedure C to give the title compound as a colorless solid. ESI(+ve) UPLC-MS (M+H)⁺ 323.3, mass=322.1.

Step 3: (R)-(3,3-difluoro-2-((5-(trifluoromethyl)pyridin-2-yloxy)methyl)pyrrolidin-1-yl)(5-methyl-2-(2H-1,2,3-triazol-2-yl)phenyl)methanone. The alcohol (1.0 eq) obtained from Step 2 was dissolved in anhydrous DMF and cooled at ice-bath. NaH (60%, 3.0eq) was added. The mixture was stirred for 1 h at RT and then 2-fluoro-5-(trifluoromethyl)pyridine (1.5 eq) was added. The mixture was stirred overnight at RT. The mixture was acidified with TFA and purified with prep-HPLC to obtain the desired product as TFA salt. ¹H NMR (400 MHz, MeOH-d₄) δ 2.32-2.50 (m, 5H), 2.54-2.71 (m, 1H), 3.35-3.52 (m, 2H), 3.70-3.92 (broad, 1H), 4.62-4.72 (m, 2H), 6.91-7.20 (m, 2H), 7.45 (d, 1H), 7.60-8.02 (m, 4H), 8.55 (s, 1H); ESI(+ve) UPLC-MS (M+H)⁺ 468.5, mass=467.1.

Compound 51: (R)-(3,3-Difluoro-2-(((5-(trifluoromethyl)pyrimidin-2-yl)amino)methyl)pyrrolidin-1-yl)(4,5-difluoro-2-(2H-1,2,3-triazol-2-yl)phenyl)methanone

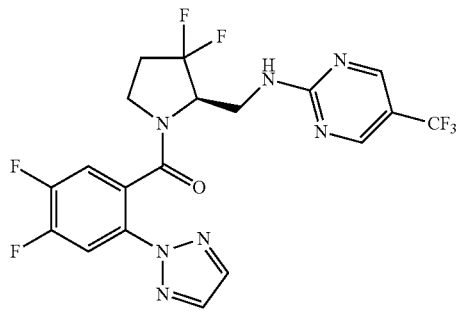 [SMILES: O=C(c1cc(F)c(F)cc1-n1nccn1)N1CCC(F)(F)[C@H]1CNc1ncc(C(F)(F)F)cn1]

¹H NMR (500 MHz, CDCl₃) δ 8.72-7.46 (m, 7H), 4.66-2.72 (m, 7H); ESI MS (M+H) 490.

Compound 52: (R)-(3,3-Difluoro-2-(((5-(trifluoromethyl)pyrimidin-2-yl)amino)methyl)pyrrolidin-1-yl)(2,3-difluoro-6-(2H-1,2,3-triazol-2-yl)phenyl)methanone

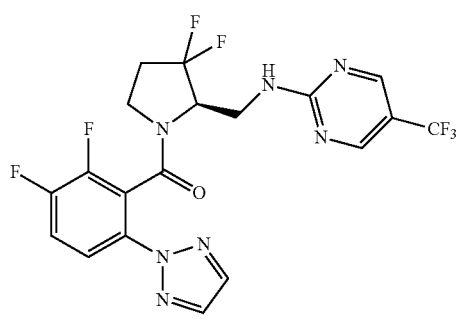 [SMILES: O=C(c1c(-n2nccn2)ccc(F)c1F)N1CCC(F)(F)[C@H]1CNc1ncc(C(F)(F)F)cn1]

¹H NMR (500 MHz, CDCl₃) δ 8.68-7.43 (m, 7H), 4.64-2.64 (m, 7H); ESI MS (M+H) 490.

Compound 53: (R)-(3,3-Difluoro-2-(((5-(trifluoromethyl)pyrimidin-2-yl)amino)methyl)pyrrolidin-1-yl)(4-fluoro-2-(2H-1,2,3-triazol-2-yl)phenyl)methanone

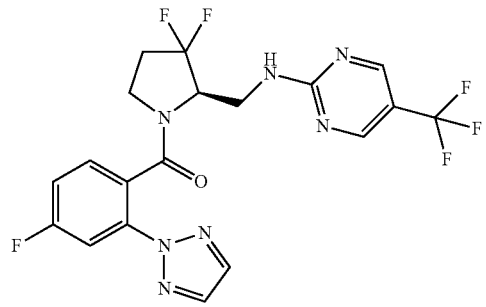 [SMILES: O=C(c1ccc(F)cc1-n1nccn1)N1CCC(F)(F)[C@H]1CNc1ncc(C(F)(F)F)cn1]

¹H NMR (500 MHz, DMSO-d₆) δ 8.72-7.42 (m, 8H), 4.67-3.27 (m, 5H), 2.47-2.35 (m, 2H); ESI MS (M+H) 472.

Compound 54: (R)-(5-Chloro-2-(2H-1,2,3-triazol-2-yl)phenyl)(3,3-difluoro-2-(((5-(trifluoromethyl)pyrimidin-2-yl)amino)methyl)pyrrolidin-1-yl)methanone

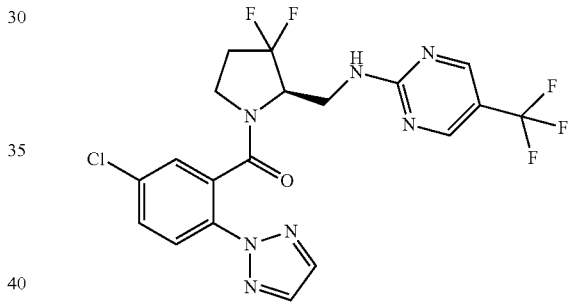

¹H NMR (500 MHz, DMSO-d₆) δ 8.72-7.45 (m, 8H), 4.67-3.21 (m, 5H), 2.63-2.36 (m, 2H); ESI MS (M+H) 488.

Compound 55: (R)-(3,3-difluoro-2-((5-(trifluoromethyl)pyrimidin-2-ylamino)methyl)pyrrolidin-1-yl)(3-methyl-2-(2H-1,2,3-triazol-2-yl)phenyl)methanone

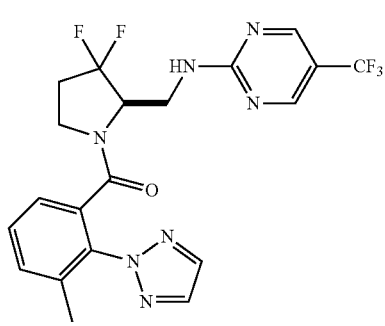 [SMILES: Cc1cccc(C(=O)N2CCC(F)(F)[C@H]2CNc2ncc(C(F)(F)F)cn2)c1-n1nccn1]

¹H NMR (400 MHz, MeOH-d₄) δ 2.14-2.24 (m, 3H), 2.36-2.53 (m, 2H), 3.38-3.89 (m, 4H), 4.30-4.51 (m, 1H), 7.14-7.57 (m, 3H), 7.88-7.98 (m, 2H), 8.31-8.65 (m, 2H); ESI(+ve) UPLC-MS (M+H)⁺ 468.5, mass=467.2.

Compound 56: (R)-3-(3,3-Difluoro-2-(((5-(trifluoromethyl)pyrimidin-2-yl)amino)methyl)pyrrolidine-1-carbonyl)-4-(2H-1,2,3-triazol-2-yl)benzonitrile

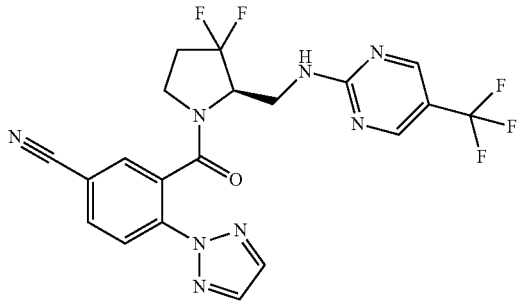 [SMILES: N#Cc1ccc(-n2nccn2)c(C(=O)N2CCC(F)(F)[C@H]2CNc2ncc(C(F)(F)F)cn2)c1]

¹H NMR (300 MHz, DMSO-d₆) δ 8.73-7.85 (m, 8H), 4.73-3.27 (m, 5H), 2.55-2.43 (m, 2H); ESI MS (M+H) 479.

Compound 57: (R)-(3,3-Difluoro-2-(((5-(trifluoromethyl)pyrimidin-2-yl)amino)methyl)pyrrolidin-1-yl)(2-fluoro-6-(2H-1,2,3-triazol-2-yl)phenyl)methanone

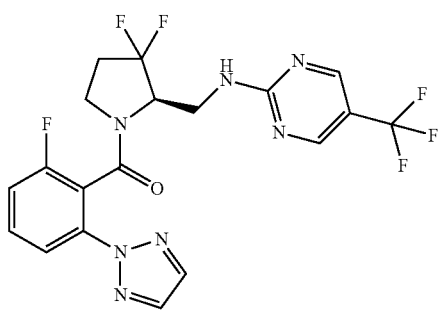

¹H NMR (500 MHz, DMSO-d₆) δ 8.68-7.16 (m, 8H), 3.86-3.58 (m, 5H), 2.58-2.39 (m, 2H); ESI MS (M+H) 472.

Compound 58: (R)-(3,3-Difluoro-2-(((5-(trifluoromethyl)pyrimidin-2-yl)amino)methyl)pyrrolidin-1-yl)(2-methyl-6-(2H-1,2,3-triazol-2-yl)phenyl)methanone

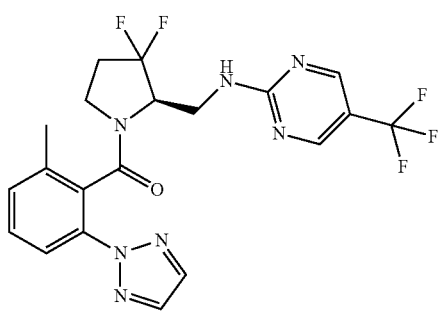 [SMILES: Cc1cccc(-n2nccn2)c1C(=O)N1CCC(F)(F)[C@H]1CNc1ncc(C(F)(F)F)cn1]

¹H NMR (500 MHz, DMSO-d₆) δ 8.70-7.25 (m, 8H), 4.66-3.20 (m, 5H), 2.64-2.17 (m, 5H); ESI MS (M+H) 468.

Compound 59: (R)-(3,3-difluoro-2-((5-(trifluoromethyl)pyrimidin-2-ylamino)methyl)pyrrolidin-1-yl)(3,4-difluoro-2-(2H-1,2,3-triazol-2-yl)phenyl)methanone

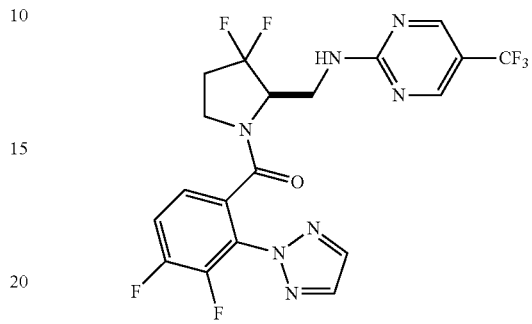

¹H NMR (400 MHz, MeOH-d₄) δ 2.28-2.63 (m, 2H), 3.39-4.12 (m, 4H), 4.61-4.76 (m, 1H), 7.26-8.09 (m, 4H), 8.34-8.70 (m, 2H); ESI(+ve) UPLC-MS (M+H)⁺ 490.5, mass=489.1.

Compound 60: (R)-(3,3-Difluoro-2-(((5-(trifluoromethyl)pyrimidin-2-yl)amino)methyl)pyrrolidin-1-yl)(3,5-dimethyl-2-(2H-1,2,3-triazol-2-yl)phenyl)methanone

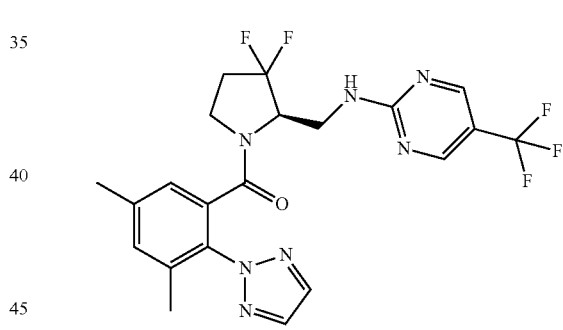

¹H NMR (500 MHz, DMSO-d₆) δ 8.71-7.04 (m, 7H), 4.43-3.42 (m, 5H), 2.46-1.97 (m, 8H); ESI MS (M+H) 482.

Compound 61: (R)-(3,3-difluoro-2-(((5-(trifluoromethyl)pyrimidin-2-yl)amino)methyl)pyrrolidin-1-yl)(3,5-difluoro-2-(2H-1,2,3-triazol-2-yl)phenyl)methanone

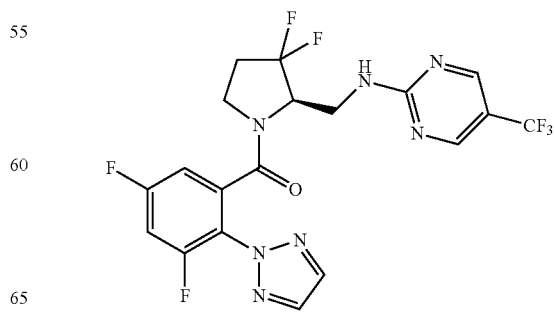

The title compound was prepared following the same general procedures as described for Example Compound 60. ESI(+ve) UPLC-MS (M+H)+ 490.4, mass=489.1.

Compound 63: (R)-(2-((5-chloropyrimidin-2-ylamino)methyl)-3,3-difluoropyrrolidin-1-yl)(3-methyl-2-(2H-1,2,3-triazol-2-yl)phenyl)methanone

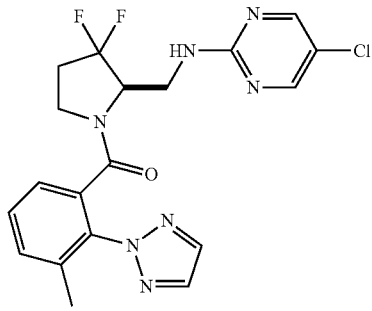 [SMILES: Cc1cccc(C(=O)N2CCC(F)(F)[C@H]2CNc2ncc(Cl)cn2)c1-n1nccn1]

$^1$H NMR (300 MHz, MeOH-d$_4$) δ 2.04-2.13 (m, 3H), 2.21-2.43 (m, 2H), 3.22-3.72 (m, 4H), 4.22-4.36 (m, 1H), 7.03-7.45 (m, 3H), 7.75-7.84 (m, 2H), 7.92-8.20 (m, 2H); ESI(+ve) UPLC-MS (M+H)+ 434.5, mass=433.1.

Compound 64: (R)-(2-((5-chloropyrimidin-2-ylamino)methyl)-3,3-difluoropyrrolidin-1-yl)(5-fluoro-2-(2H-1,2,3-triazol-2-yl)phenyl)methanone

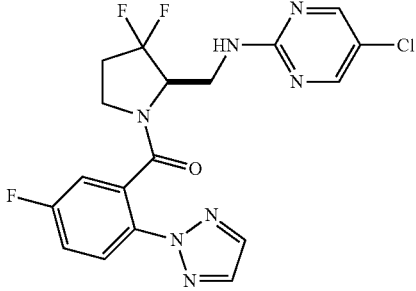 [SMILES: O=C(c1cc(F)ccc1-n1nccn1)N1CCC(F)(F)[C@H]1CNc1ncc(Cl)cn1]

The compound was prepared by General Method C using compound Compound (r) (25 mg, 0.10 mmol) and acid 5-Fluoro-2-(2H-1,2,3-triazol-2-yl)benzoic acid (23 mg, 0.11 mmol). The crude was purified by column chromatography (silica gel, petroleum ether/ethyl acetate: 5/1) to afford the target Compound 64 (25 mg, 0.057 mmol, 56%) as a yellow oil. $^1$H NMR (400 MHz, CDCl$_3$): δ=2.30 (m, 2H), 3.26-3.40 (m, 2H), 3.95-4.01 (m, 2H), 4.40-4.60 (m, 1H), 6.23 (br, 1H), 7.72-7.84 (m, 3H), 7.94-8.01 (m, 2H), 8.20 (s, 2H); ESI(+ve) UPLC-MS (M+H)+ 438.5, mass=437.1.

Compound 65: (R)-(2-((5-chloropyrimidin-2-ylamino)methyl)-3,3-difluoropyrrolidin-1-yl)(5-methyl-2-(2H-1,2,3-triazol-2-yl)phenyl)methanone

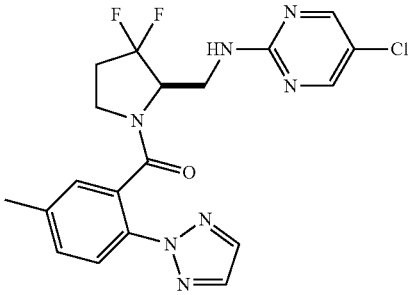 [SMILES: Cc1ccc(-n2nccn2)c(C(=O)N2CCC(F)(F)[C@H]2CNc2ncc(Cl)cn2)c1]

$^1$H NMR (400 MHz, MeOH-d$_4$) δ 2.30-2.66 (m, 5H), 3.38-4.06 (m, 4H), 4.56-4.72 (m, 1H), 7.26-7.53 (m, 2H), 7.67-8.01 (m, 3H), 8.03-8.40 (m, 2H); ESI(+ve) UPLC-MS (M+H)+ 434.9, mass=433.1.

Compound 66: (R)-3-(2-((5-chloropyrimidin-2-ylamino)methyl)-3,3-difluoropyrrolidine-1-carbonyl)-4-(2H-1,2,3-triazol-2-yl)benzonitrile

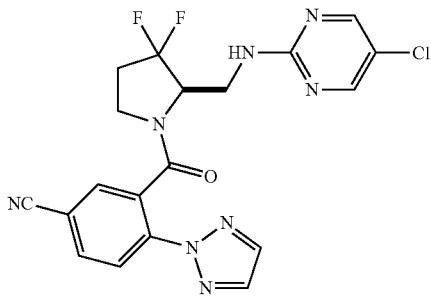 [SMILES: N#Cc1ccc(-n2nccn2)c(C(=O)N2CCC(F)(F)[C@H]2CNc2ncc(Cl)cn2)c1]

$^1$H NMR (400 MHz, MeOH-d$_4$) δ 2.30-2.65 (m, 2H), 3.36-4.11 (m, 4H), 4.55-4.81 (m, 1H), 7.70-8.04 (m, 3H), 8.06-8.21 (m, 2H), 8.22-8.40 (m, 2H); ESI(+ve) UPLC-MS (M+H)+ 445.4, mass=444.1.

Compound 67: (R)-(2-((5-chloropyrimidin-2-ylamino)methyl)-3,3-difluoropyrrolidin-1-yl)(3,4-difluoro-2-(2H-1,2,3-triazol-2-yl)phenyl)methanone

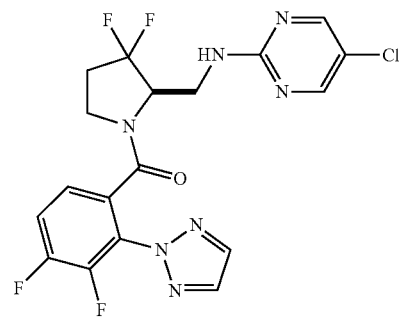 [SMILES: O=C(c1ccc(F)c(F)c1-n1nccn1)N1CCC(F)(F)[C@H]1CNc1ncc(Cl)cn1]

¹H NMR (400 MHz, MeOH-d₄) δ 2.28-2.59 (m, 2H), 3.39-4.04 (m, 4H), 4.56-4.70 (m, 1H), 7.28-8.05 (m, 4H), 8.07-8.32 (m, 2H); ESI(+ve) UPLC-MS (M+H)⁺ 456.6, mass=455.1.

Compound 68: (R)-(2-((5-chloropyrimidin-2-ylamino)methyl)-3,3-difluoropyrrolidin-1-yl)(3-fluoro-4-methyl-2-(2H-1,2,3-triazol-2-yl)phenyl)methanone

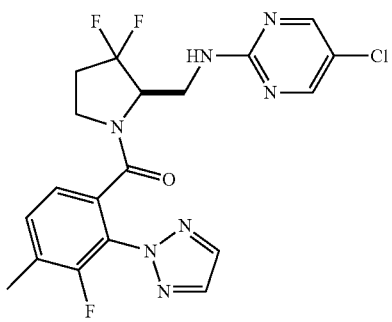

¹H NMR (300 MHz, MeOH-d₄) δ 2.14-2.48 (m, 5H), 3.31-3.76 (m, 4H), 4.13-4.43 (m, 1H), 6.94-7.42 (m, 2H), 7.79-7.86 (2×s, 2H), 7.93-8.19 (2×s, 2H); ESI(+ve) UPLC-MS (M+H)⁺ 452.4, mass=451.1.

Compound 69: (R)-(2-((5-chloropyrimidin-2-ylamino)methyl)-3,3-difluoropyrrolidin-1-yl)(4-fluoro-3-methyl-2-(2H-1,2,3-triazol-2-yl)phenyl)methanone

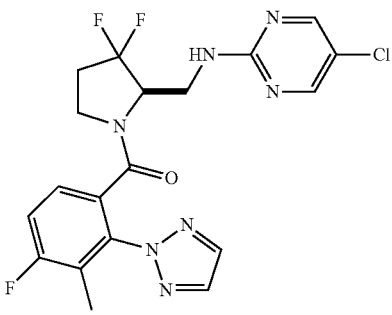

¹H NMR (400 MHz, MeOH-d₄) δ 2.07-2.15 (2×d, 3H), 2.34-2.55 (m, 2H), 3.32-3.84 (m, 4H), 4.36-4.49 (m, 1H), 7.10-7.44 (m, 2H), 7.90-8.00 (2×s, 2H), 8.08-8.29 (2×s, 2H); ESI(+ve) UPLC-MS (M+H)⁺ 452.7, mass=451.1.

Compound 70: (R)-(3-(2H-1,2,3-triazol-2-yl)pyridin-2-yl)(2-((5-chloropyrimidin-2-ylamino)methyl)-3,3-difluoropyrrolidin-1-yl)methanone

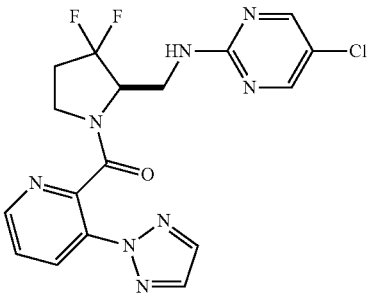

¹H NMR (400 MHz, MeOH-d₄) δ 2.31-2.69 (m, 2H), 3.51-3.65 (m, 2H), 3.74-4.05 (m, 2H), 4.48-4.74 (m, 1H); ESI(+ve) UPLC-MS (M+H)⁺ 421.2, mass=420.1.

Compound 71: (R)-(2-((5-chloropyrimidin-2-ylamino)methyl)-3,3-difluoropyrrolidin-1-yl)(3-methyl-2-(pyrimidin-2-yl)phenyl)methanone

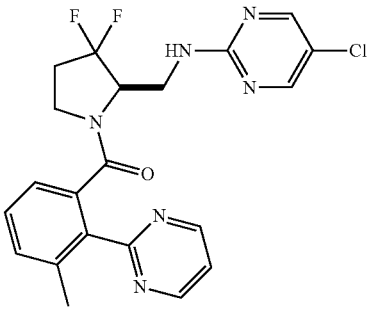

¹H NMR (400 MHz, CDCl₃) δ 2.16-2.49 (m, 5H), 3.36-3.89 (m, 4H), 4.37-4.63 (m, 1H), 7.06-7.72 (m, 4H), 7.95-8.39 (broad, 2H), 8.72-8.96 (broad, 2H); ESI(+ve) UPLC-MS (M+H)⁺ 445.4, mass=444.1.

Compound 74: (R)-(3,3-difluoro-2-((5-(trifluoromethyl)pyridin-2-yloxy)methyl)pyrrolidin-1-yl)(5-fluoro-2-(2H-1,2,3-triazol-2-yl)phenyl)methanone

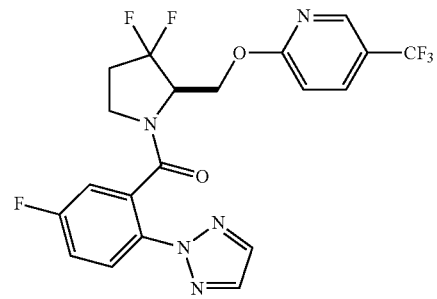

The title compound was prepared following the same general procedures as described for Example Compound 25. ¹H NMR (400 MHz, MeOH-d₄) δ 2.35-2.51 (m, 1H), 2.51-2.71 (m, 1H), 3.39-3.58 (m, 2H), 3.58-3.99 (broad, 1H), 4.60-4.77 (m, 2H), 6.90-7.25 (m, 2H), 7.31-7.49 (m, 1H), 7.59-7.91 (broad, 2H), 7.93-8.07 (m, 2H), 8.54 (s, 1H); ESI(+ve) UPLC-MS (M+H)⁺ 472.4, mass=471.1.

Compound 76: (R)-(2-cyclopropyl-5-(4-fluorophenyl)thiazol-4-yl)(3,3-difluoro-2-((5-(trifluoromethyl)pyrimidin-2-ylamino)methyl)pyrrolidin-1-yl)methanone

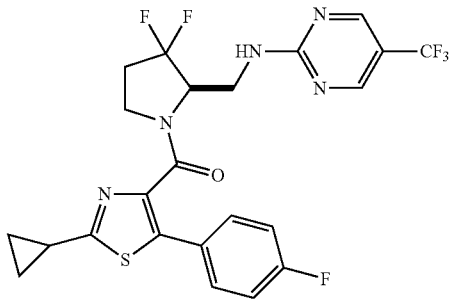

¹H NMR (400 MHz, MeOH-d₄) δ 1.00-1.07 (m, 2H), 1.13-1.23 (m, 2H), 2.15-2.25 (m, 1H), 2.31-2.60 (m, 2H), 3.22-4.05 (m, 4H), 4.60-4.89 (m, 1H), 7.13 (t, 2H), 7.42-7.50 (m, 2H), 8.35-8.60 (m, 2H); ESI(+ve) UPLC-MS (M+H)⁺ 528.4, mass=527.1.

Compound 77: (R)-(3,3-difluoro-2-((5-(trifluoromethyl)pyrazin-2-ylamino)methyl)pyrrolidin-1-yl)(5-fluoro-2-(2H-1,2,3-triazol-2-yl)phenyl)methanone

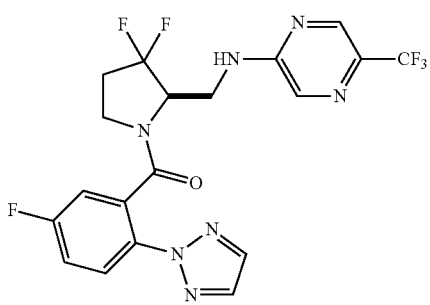

¹H NMR (400 MHz, MeOH-d₄) δ 2.21-2.51 (m, 2H), 3.29-3.96 (m, 4H), 4.48-4.60 (m, 1H), 7.27-7.36 (m, 1H), 7.76-7.83 (m, 3H), 7.91 (s, 1H), 7.95 (2×d, 1H), 8.28 (s, 1H); ESI(+ve) UPLC-MS (M+H)⁺ 472.4, mass=471.1.

Compound 78: (R)-(3,3-difluoro-2-(((5-(trifluoromethyl)pyrimidin-2-yl)amino)methyl)pyrrolidin-1-yl)(3-methyl-2-(pyrimidin-2-yl)phenyl)methanone

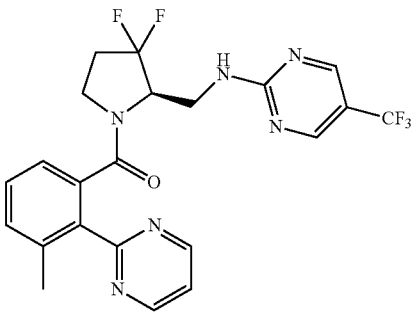 [SMILES: Cc1cccc(C(=O)N2CCC(F)(F)[C@H]2CNc2ncc(C(F)(F)F)cn2)c1-c1ncccn1]

The title compound was prepared following the same general procedures as described for Example Compound 10. ESI(+ve) UPLC-MS (M+H)⁺ 479.4, mass=478.2.

Compound 79: (R)-(3,3-difluoro-2-(((5-(trifluoromethyl)pyrimidin-2-yl)amino)methyl)pyrrolidin-1-yl)(3-fluoro-2-(pyrimidin-2-yl)phenyl)methanone

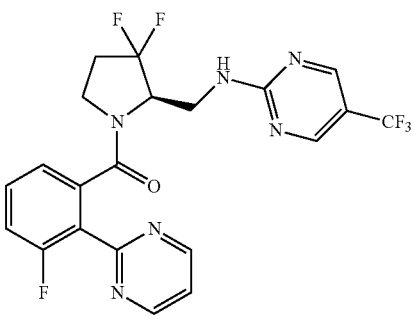

The title compound was prepared following the same general procedures as described for Example Compound 10. ESI(+ve) UPLC-MS (M+H)⁺ 483.4, mass=482.1.

Compound 80: (R)-(3-(1H-pyrazol-1-yl)pyridin-2-yl)(3,3-difluoro-2-((5-(trifluoromethyl)pyrimidin-2-ylamino)methyl)pyrrolidin-1-yl)methanone

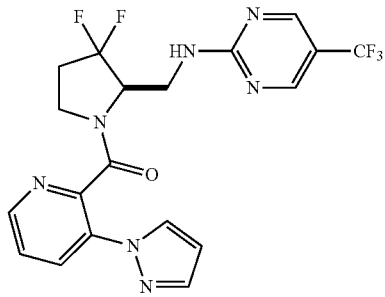

¹H NMR (400 MHz, MeOH-d₄) δ 2.37-2.64 (m, 2H), 3.52-4.06 (m, 4H), 4.58-4.75 (m, 1H), 6.51-6.61 (m, 1H), 7.43-7.79 (m, 2H), 7.99-8.20 (m, 2H), 8.24-8.67 (m, 3H); ESI(+ve) UPLC-MS (M+H)+ 454.5, mass=453.1.

Additional examples are prepared using methods analogous to those described above.

Example 2

Orexin Receptor Cell-Based Functional Assay

Measurement of $[Ca^{2+}]i$ using a FLIPR: CHO-OX$_1$ or CHO-OX$_2$ cells were seeded into black-walled clear-base 384-well plates (Corning, catalog #3712) at a density of 20,000 cells per well in F12-K medium supplemented with 10% FBS and then incubated in a 5% CO2, 37 C incubator overnight to reach 90% confluency. The cells were incubated with equal volume of calcium6 loading buffer (Molecular Devices, Inc.) containing 2.5 mM probenecid at 37° C. for 2 h, followed by test compounds (dose-range 0.1 nM-10 µM) for another 30 min. The plates were then placed into a FLIPR (Molecular Devices, Inc.) to monitor fluorescence (λ excitation 488 nm, λ emission 540 nm) before and after the addition of EC$_{90}$ of [OXA]. Results for exemplary compounds of Formulae I and II are shown in Table 2.

TABLE 2

IC$_{50}$ Bioactivity of Exemplary Compounds of the Application with Respect to OX$_1$ and OX$_2$

| Example | OX$_1$(µM) | OX$_2$(µM) |
| --- | --- | --- |
| 1 | 0.001 | >5.0 |
| 2 | 0.004 | >5.0 |
| 3 | 0.004 | >5.0 |
| 5 | 0.004 | >5.0 |
| 7 | 0.015 | >5.0 |
| 8 | 0.011 | >5.0 |
| 10 | 0.002 | >5.0 |
| 25 | 0.230 | >5.0 |
| 51 | 0.024 | 0.84 |
| 52 | 0.006 | >5.0 |
| 53 | 0.015 | 0.83 |
| 54 | 0.003 | >5.0 |
| 55 | 0.007 | >5.0 |
| 56 | 0.014 | >5.0 |
| 57 | 0.003 | >5.0 |
| 58 | 0.014 | >5.0 |
| 59 | 0.757 | >5.0 |
| 60 | 0.016 | >5.0 |
| 63 | 0.003 | >5.0 |
| 64 | 0.022 | >5.0 |
| 65 | 0.006 | >5.0 |
| 66 | 0.006 | >5.0 |
| 67 | 1.0 | >5.0 |
| 68 | 0.105 | >5.0 |
| 69 | 0.021 | >5.0 |
| 70 | 0.020 | >5.0 |
| 74 | 0.660 | >5.0 |
| 77 | 0.003 | 0.720 |

Example 3

Nicotine Self-Administration Assay

For all experiments, rats weighing 250-300 g are housed in groups of 1-23 per cage, in a temperature-controlled vivarium under a reversed 12-h light/dark cycle (lights off at 8 am). Food and water are provided ad libitum until behavioral training commences. During training, rats are food-restricted to maintain ~85-90% of their free-feeding body weight. Behavioral testing occurs during the dark portion of the light/dark cycle between the hours of 9 am-1 pm, during the early portion of the dark phase of the cycle. All procedures are conducted in strict adherence with the National Institutes of Health Guide for the Care and Use of Laboratory Animals and are approved by the Institutional Animal Care and Use Committee of The Scripps Research Institute. Rats are anesthetized by inhalation of 1-3% isoflurane in oxygen and silastic catheters are inserted into the jugular veins. Briefly, the catheters consist of a 14 cm length of silastic tubing fitted to a guide cannula (Plastics One, Wallingford, Conn.), bent at a curved right angle and encased in dental acrylic. The catheter tubing is passed subcutaneously from each animal's back to the right jugular vein, and 1 cm length of the catheter tip is inserted into the vein. After surgery, catheters are flushed daily with 0.1 mL of a heparinized (30 USP units/ml) sterile saline solution. Following 7 d of surgical recovery, rats are mildly food restricted to 85-90% of their free-feeding body weight and trained to press a lever in an operant chamber (Med Associates, St. Albans, Vt.) for food pellets (20 mg; TestDiet, Richmond, Ind.) under a fixed-ratio 5, time out 20 s (FR5TO20 s) schedule of reinforcement prior to catheter implantation. Once stable responding is achieved (>25 pellets per session), rats are permitted to acquire IV nicotine self-administration by autoshaping during 1-h daily sessions, 7 days per week. Nicotine is delivered through the tubing into the IV catheter by a Razel syringe pump (Med Associates). Each nicotine self-administration session is performed using two retractable levers (1 active; 1 inactive). Completion of the response criteria on the active lever results in the delivery of an IV nicotine infusion (0.03 mg/kg/infusion). After 1 week, the nicotine dose is increased to 0.1 mg/kg/inf for the remainder of the experiment, including subsequent training and test sessions. Delivery of all nicotine infusions coincides with the initiation of a 20-s time-out (TO) period, signaled by a light cue located above the lever. During the TO period, responding on the lever is recorded but without scheduled consequence. Catheter integrity is tested with the ultrashort-acting barbiturate Brevital (methohexital sodium; Eli Lilly) at the end of the experiment.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:
1. A compound of Formula (I):

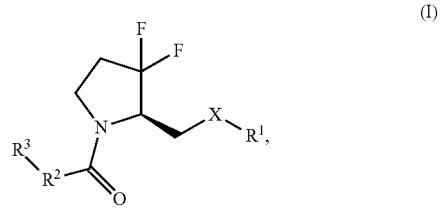

wherein
X is NR$^4$ or O;
R$^1$ is a monocyclic or bicyclic heteroaryl group, wherein R$^1$ is unsubstituted or substituted with one or more substituents independently selected from the group consisting of alkyl, haloalkyl, halo, —OH, —O-alkyl, —CN, —NR$^a$R$^b$, —N(R$^a$)C(O) alkyl, —N(R$^a$)CO$_2$alkyl, —N(R$^a$)SO$_2$alkyl, —C(O)alkyl, —CO$_2$H, —CO$_2$alkyl, —CONR$^a$R$^b$, —SO$_2$alkyl, and —SO$_2$NR$^a$R$^b$;

where R$^a$ and R$^b$ are each independently H or alkyl;

R$^2$ is phenyl or a monocyclic heteroaryl, wherein R$^2$ is unsubstituted or substituted with one or more substituents independently selected from the group consisting of alkyl, haloalkyl, cycloalkyl, halo, —OH, —O-alkyl, —CN, —NR$^c$R$^d$, —N(R$^a$)C(O) alkyl, —N(R$^c$)CO$_2$alkyl, —N(R$^c$)SO$_2$alkyl, —C(O)alkyl, —CO$_2$H, —CO$_2$alkyl, —CONR$^c$R$^d$, —SO$_2$alkyl, and —SO$_2$NR$^c$R$^d$;

where R$^c$ and R$^d$ are each independently H or alkyl;

R$^3$ is phenyl or a monocyclic heteroaryl, wherein R$^3$ is unsubstituted or substituted with one or more substituents independently selected from the group consisting of alkyl, haloalkyl, halo, —OH, —O-alkyl, —CN, —NR$^e$R$^f$, —N(R$^e$)C(O) alkyl, —N(R$^e$)CO$_2$alkyl, —N(R$^e$)SO$_2$alkyl, —C(O)alkyl, —CO$_2$H, —CO$_2$alkyl, —CONR$^e$R$^f$, —SO$_2$alkyl, and —SO$_2$NR$^e$R$^f$;

where R$^e$ and R$^f$ are each independently H or alkyl; and R$^4$ is H or alkyl;

or a pharmaceutically acceptable salt thereof.

2. The compound of claim 1, wherein X is NR$^4$.

3. The compound of claim 1, wherein R$^4$ is H.

4. The compound of claim 1, wherein R$^1$ is a monocyclic heteroaryl.

5. The compound of claim 1, wherein R$^1$ is selected from the list consisting of pyrimidinyl, pyridinyl, pyrazinyl, thiadiazolyl, and benzoxazolyl.

6. The compound of claim 5, wherein R$^1$ is pyrimidinyl or pyridinyl.

7. The compound of claim 1, wherein R$^1$ is unsubstituted.

8. The compound of claim 1, wherein R$^1$ is substituted with one or more substituents independently selected from the group consisting of alkyl, haloalkyl, and halo.

9. The compound of claim 8, wherein R$^1$ is substituted with one or more substituents independently selected from the group consisting of methyl, —CF$_3$, —F, or —Cl.

10. The compound of claim 1, wherein R$^1$ is pyrimidinyl substituted with —CF$_3$.

11. The compound of claim 1, wherein R$^1$ is pyridinyl substituted with —CF$_3$.

12. The compound of claim 1, wherein R$^1$ is pyrimidinyl substituted with —Cl.

13. The compound of claim 1, wherein R$^2$ is phenyl.

14. The compound of claim 1, wherein R$^2$ is a monocyclic heteroaryl.

15. The compound of claim 1, wherein R$^2$ is phenyl or a monocyclic heteroaryl, wherein R$^2$ is unsubstituted or substituted with one or more substituents independently selected from the group consisting of alkyl, haloalkyl, halo, —OH, —O-alkyl, —CN, —NR$^c$R$^d$, —N(R$^a$)C(O) alkyl, —N(R$^c$)CO$_2$alkyl, —N(R$^c$)SO$_2$alkyl, —C(O)alkyl, —CO$_2$H, —CO$^2$alkyl, —CONR$^c$R$^d$, —SO$_2$alkyl, and —SO$_2$NR$^c$R$^d$.

16. The compound of claim 15, wherein R$^2$ is substituted with one or more substituents independently selected from the group consisting of alkyl, haloalkyl, halo, and —CN.

17. The compound of claim 15, wherein R$^2$ is substituted with one or more substituents independently selected from the group consisting of methyl, —CF$_3$, —F, —Cl, and —CN.

18. The compound of claim 1, wherein R$^2$ is substituted with one or two methyl or fluoro groups.

19. The compound of claim 1, wherein R$^3$ is phenyl.

20. The compound of claim 1, wherein R$^3$ is a monocyclic heteroaryl.

21. The compound of claim 20, wherein R$^3$ is triazolyl, pyrimidinyl, or pyrazolyl.

22. The compound of claim 1, wherein R$^3$ is unsubstituted.

23. The compound of claim 1, wherein R$^3$ is substituted with one or more substituents independently selected from the group consisting of -alkyl, haloalkyl, and halo.

24. The compound of claim 23, wherein R$^3$ is substituted with fluoro.

25. The compound of claim 1, wherein when one of R$^2$ and R$^3$ is phenyl, the other is not phenyl.

26. The compound of claim 1, wherein when one of R$^2$ and R$^3$ is heteroaryl, the other is not heteroaryl.

27. The compound of claim 1, selected from a group consisting of compounds 1-91:

| Ex. | Structure |
|---|---|
| 1 | (structure) |
| 2 | (structure) |
| 3 | (structure) |

| Ex. | Structure |
|---|---|
| 4 | 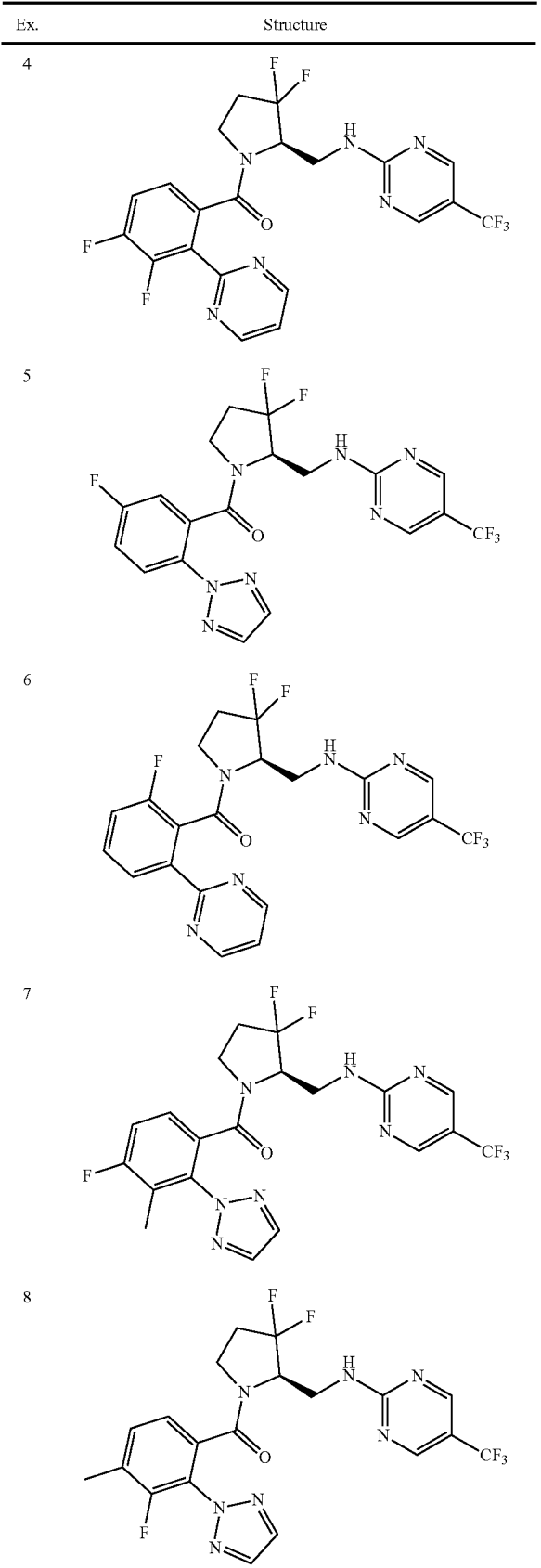 |
| 5 | |
| 6 | |
| 7 | |
| 8 | |
| Ex. | Structure |
|---|---|
| 9 | 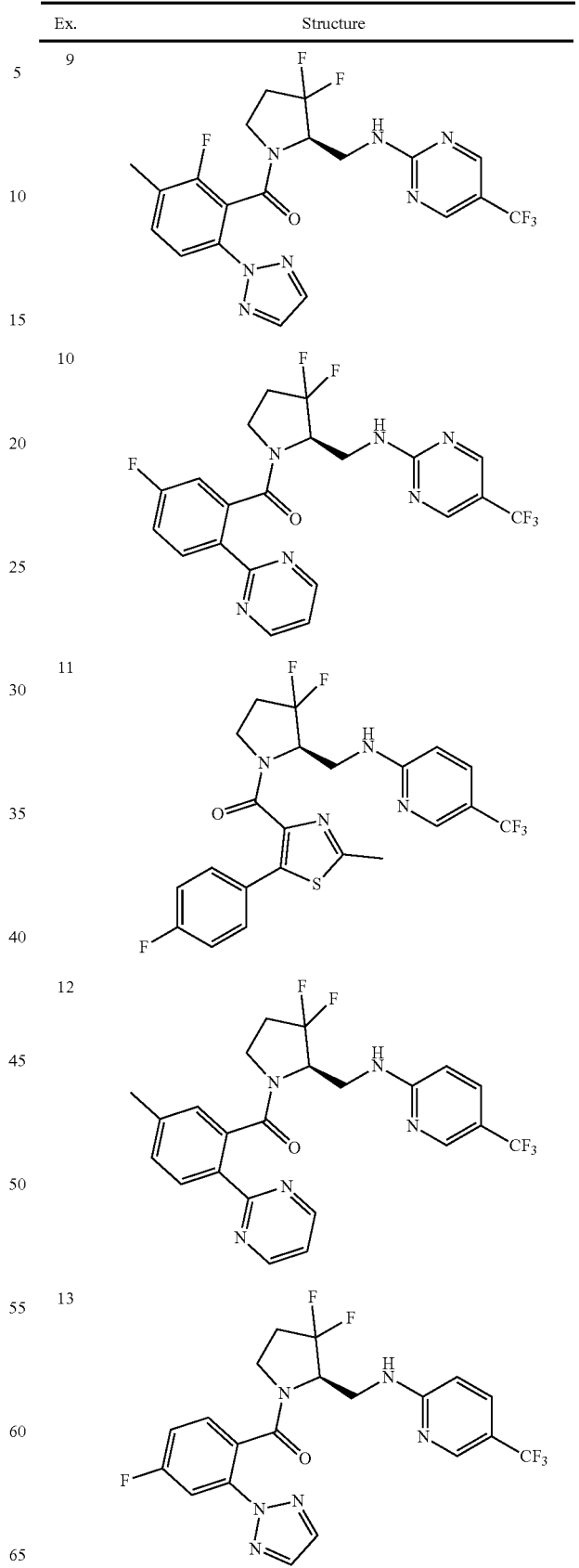 |
| 10 | |
| 11 | |
| 12 | |
| 13 | |

| Ex. | Structure |
|---|---|
| 14 | 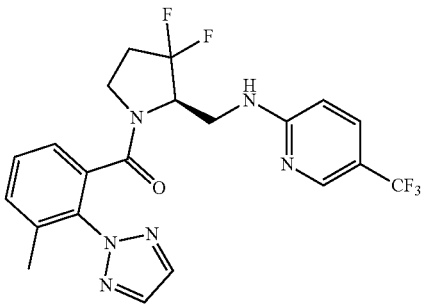 [SMILES: Cc1cccc(C(=O)N2CCC(F)(F)[C@H]2CNc2ccc(C(F)(F)F)cn2)c1-n1nccn1] |
| 15 | 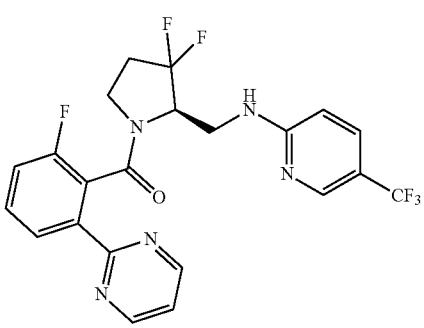 [SMILES: O=C(c1c(F)cccc1-c1ncccn1)N1CCC(F)(F)[C@H]1CNc1ccc(C(F)(F)F)cn1] |
| 16 | 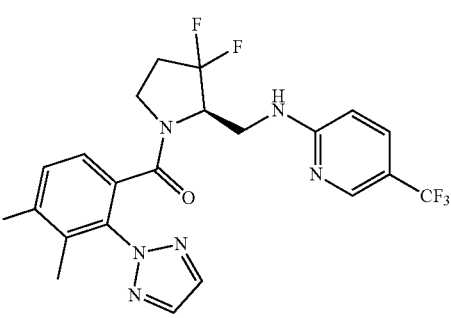 |
| 17 | 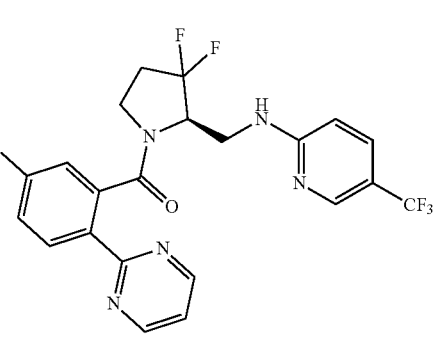 |
| 18 | 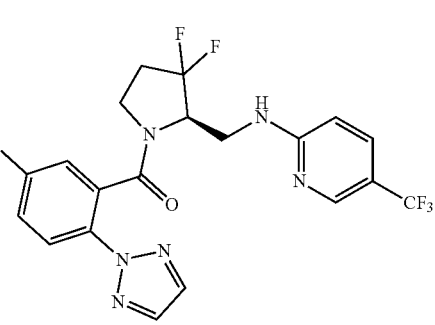 |
| Ex. | Structure |
|---|---|
| 19 | 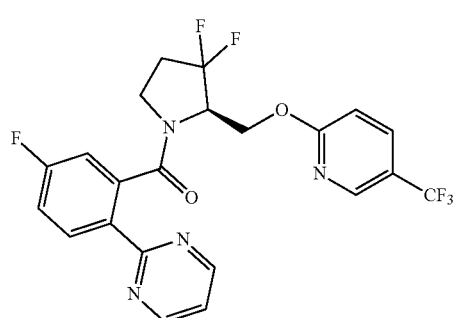 |
| 20 | 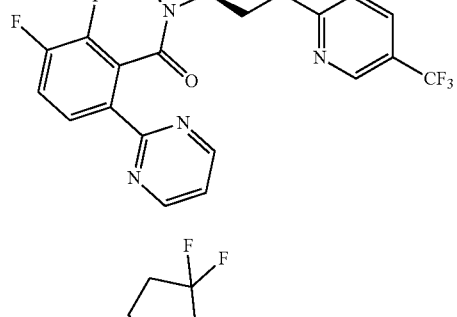 |
| 21 | 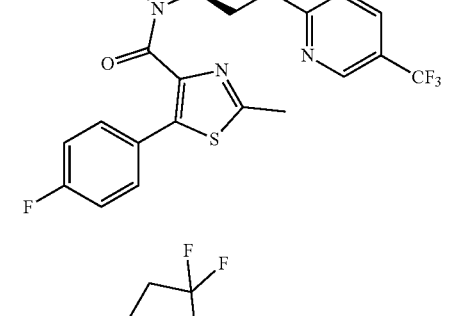 |
| 22 | 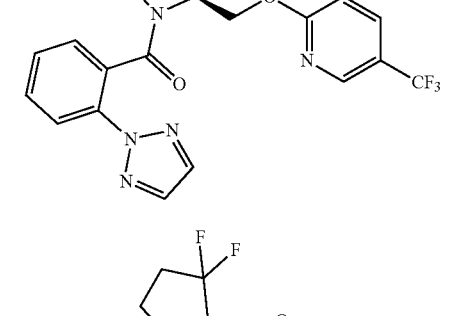 |
| 23 | 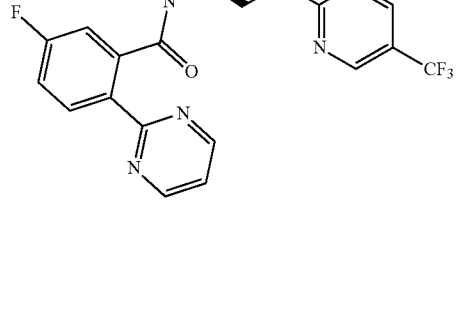 |

| Ex. | Structure |
|---|---|
| 24 | *(structure)* |
| 25 | *(structure)* |
| 26 | *(structure)* |
| 27 | *(structure)* |
| 28 | *(structure)* |
| 29 | *(structure)* |
| 30 | *(structure)* |
| 31 | *(structure)* |
| 32 | *(structure)* |
| 33 | *(structure)* |

| Ex. | Structure |
|---|---|
| 34 | 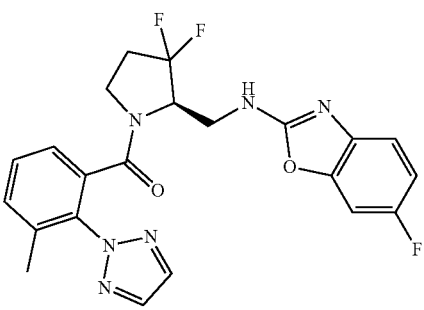 [SMILES: Cc1cccc(C(=O)N2CCC(F)(F)[C@H]2CNc2nc3ccc(F)cc3o2)c1-n1nccn1] |
| 35 | 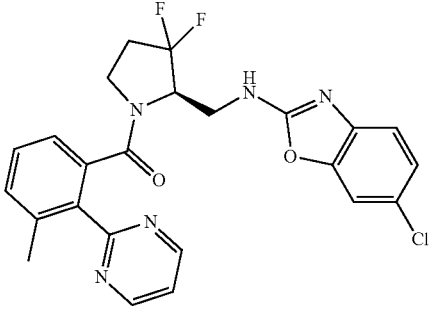 [SMILES: Cc1cccc(C(=O)N2CCC(F)(F)[C@H]2CNc2nc3ccc(Cl)cc3o2)c1-c1ncccn1] |
| 36 | 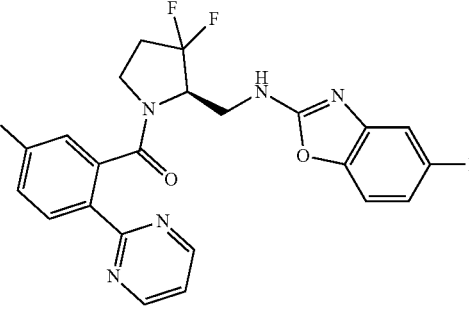 |
| 37 | 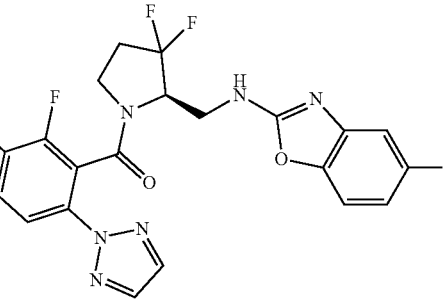 |
| 38 | 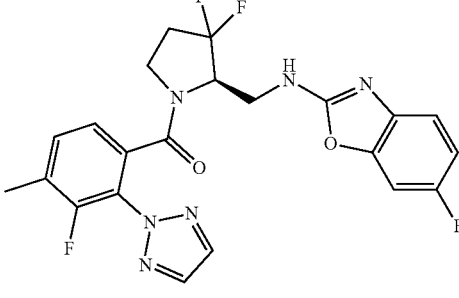 |
| Ex. | Structure |
|---|---|
| 39 | 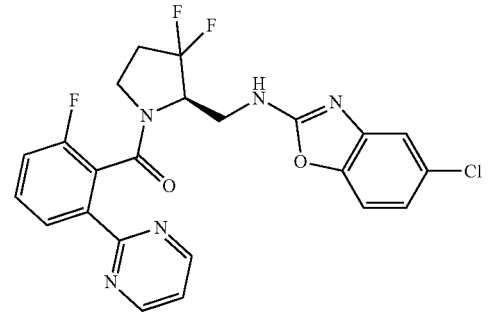 [SMILES: O=C(c1c(F)cccc1-c1ncccn1)N1CCC(F)(F)[C@H]1CNc1nc2cc(Cl)ccc2o1] |
| 40 | 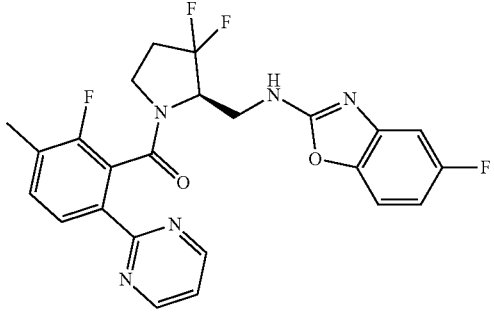 [SMILES: Cc1ccc(-c2ncccn2)c(C(=O)N2CCC(F)(F)[C@H]2CNc2nc3cc(F)ccc3o2)c1F] |
| 41 | 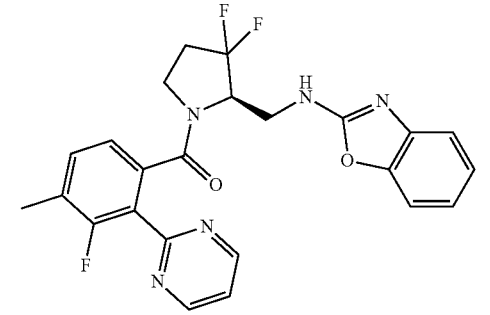 [SMILES: Cc1ccc(C(=O)N2CCC(F)(F)[C@H]2CNc2nc3ccccc3o2)c(-c2ncccn2)c1F] |
| 42 | 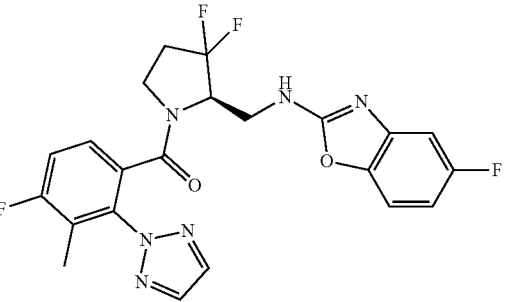 |
| 43 | 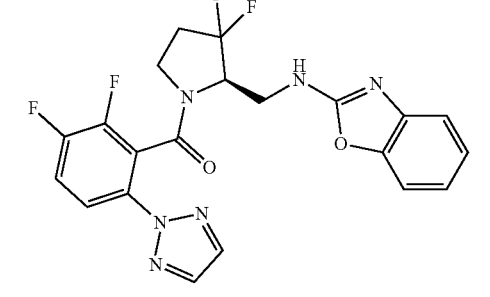 |

| Ex. | Structure |
|---|---|
| 44 | 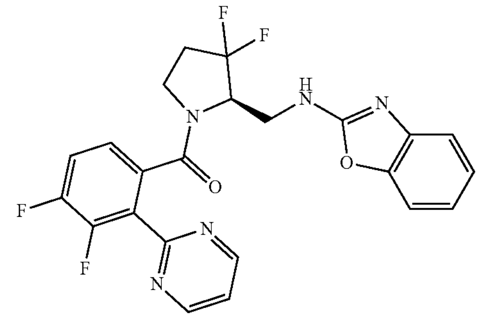 [SMILES: O=C(c1ccc(F)c(F)c1-c1ncccn1)N1CCC(F)(F)[C@H]1CNc1nc2ccccc2o1] |
| 45 | 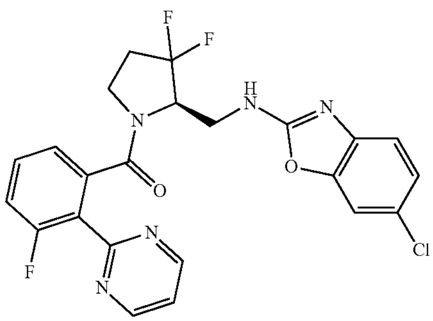 [SMILES: O=C(c1cccc(F)c1-c1ncccn1)N1CCC(F)(F)[C@H]1CNc1nc2ccc(Cl)cc2o1] |
| 46 | 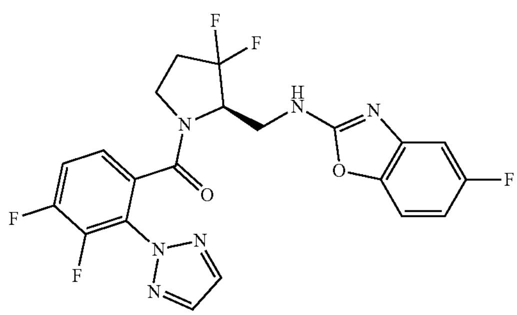 [SMILES: O=C(c1ccc(F)c(F)c1-n1nccn1)N1CCC(F)(F)[C@H]1CNc1nc2cc(F)ccc2o1] |
| 47 | 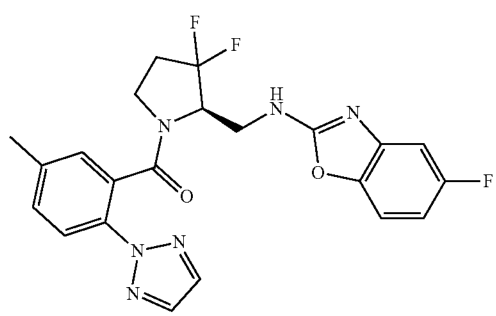 [SMILES: Cc1ccc(-n2nccn2)c(C(=O)N2CCC(F)(F)[C@H]2CNc2nc3cc(F)ccc3o2)c1] |
| 48 | 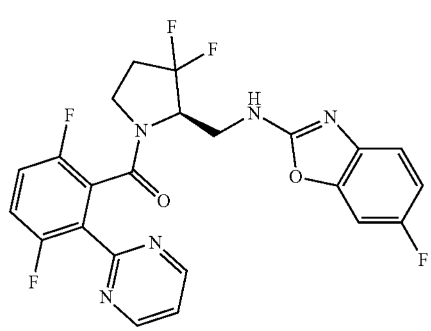 [SMILES: O=C(c1c(F)ccc(F)c1-c1ncccn1)N1CCC(F)(F)[C@H]1CNc1nc2ccc(F)cc2o1] |

| Ex. | Structure |
|---|---|
| 49 | 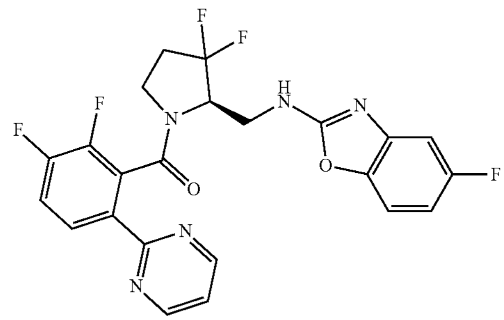 [SMILES: O=C(c1c(-c2ncccn2)ccc(F)c1F)N1CCC(F)(F)[C@H]1CNc1nc2cc(F)ccc2o1] |
| 50 | 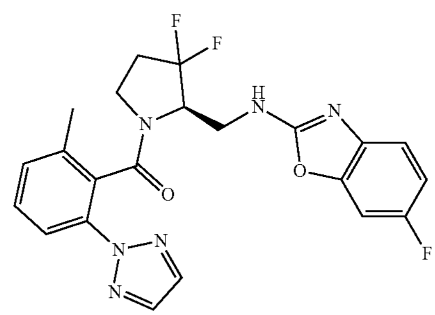 [SMILES: Cc1cccc(-n2nccn2)c1C(=O)N1CCC(F)(F)[C@H]1CNc1nc2ccc(F)cc2o1] |
| 51 | 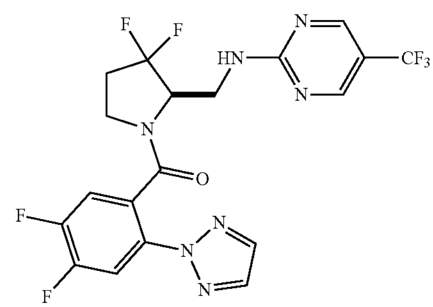 |
| 52 | 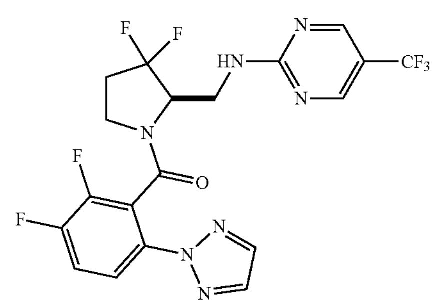 |
| 53 | 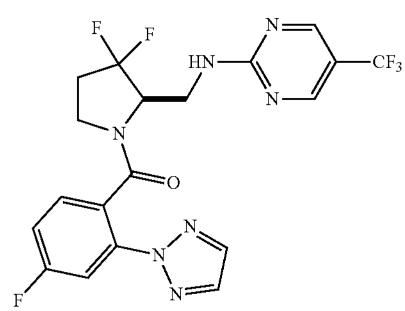 |

-continued

| Ex. | Structure |
|---|---|
| 54 | (structure) |
| 55 | (structure) |
| 56 | (structure) |
| 57 | (structure) |
| 58 | (structure) |
| 59 | (structure) |
| 60 | (structure) |
| 61 | (structure) |
| 62 | (structure) |
| 63 | (structure) |

| Ex. | Structure | | Ex. | Structure |
|---|---|---|---|---|
| 64 | 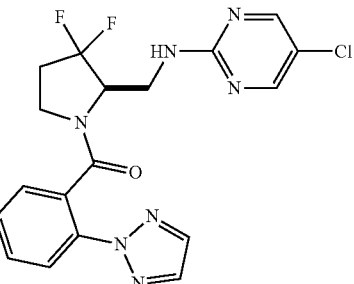 | | 69 | 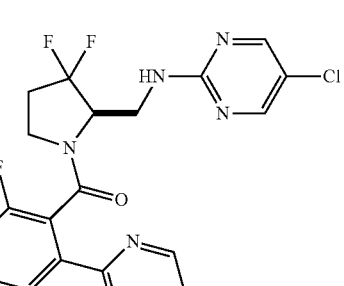 |
| 65 | 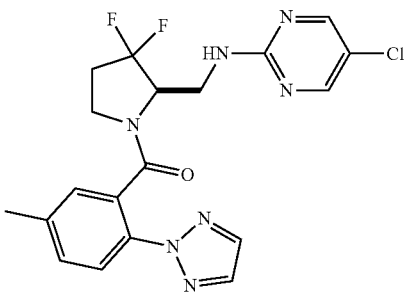 | | 70 | 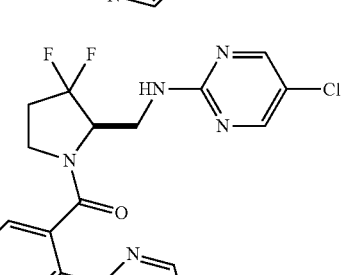 |
| 66 | 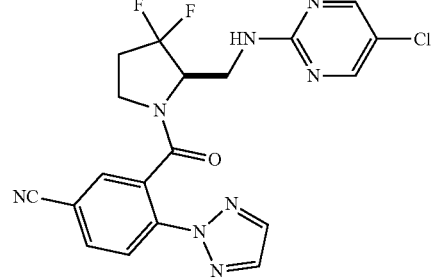 | | 71 | 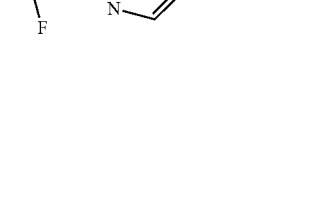 |
| 67 | 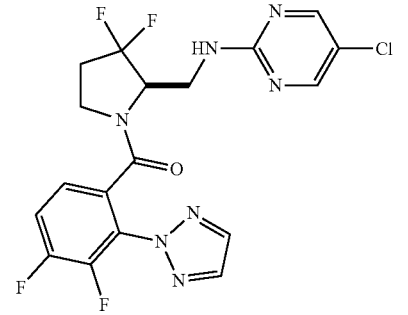 | | 72 | 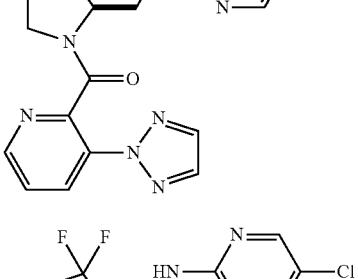 |
| 68 | 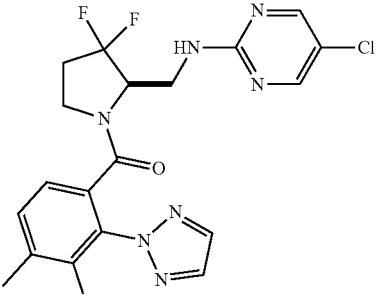 | | 73 | 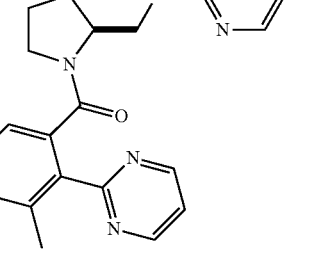 |

| Ex. | Structure |
|---|---|
| 74 | (structure) |
| 75 | (structure) |
| 76 | (structure) |
| 77 | (structure) |
| 78 | (structure) |
| 79 | (structure) |
| 80 | (structure) |
| 81 | (structure) |
| 82 | (structure) |
| 83 | (structure) |

-continued

| Ex. | Structure |
|---|---|
| 84 | (structure) |
| 85 | (structure) |
| 86 | (structure) |
| 87 | (structure) |

-continued

| Ex. | Structure |
|---|---|
| 88 | (structure) |
| 89 | (structure) |
| 90 | (structure) |
| 91 | (structure) | and pharmaceutically acceptable salts thereof.

28. A pharmaceutical composition comprising (a) a compound of claim 1, and (b) a pharmaceutically acceptable excipient.

* * * * *